US006444656B1

(12) United States Patent
Nguyen-Ba et al.

(10) Patent No.: US 6,444,656 B1
(45) Date of Patent: Sep. 3, 2002

(54) ANTIVIRAL PHOSPHONATE NUCLEOTIDES

(75) Inventors: Nghe Nguyen-Ba, La Prairie; Rabindra Rej, Montreal, both of (CA)

(73) Assignee: BioChem Pharma, Inc., Quebec (CA)

( * ) Notice: Subject to any disclaimer, the term of this patent is extended or adjusted under 35 U.S.C. 154(b) by 0 days.

(21) Appl. No.: 09/534,490

(22) Filed: Mar. 24, 2000

Related U.S. Application Data

(63) Continuation-in-part of application No. 09/411,979, filed on Oct. 4, 1999, which is a division of application No. 08/868,782, filed on Jun. 4, 1997, now Pat. No. 6,005,107, which is a continuation of application No. 08/868,706, filed on Jun. 4, 1997, now Pat. No. 5,955,610, which is a continuation of application No. 08/465,921, filed on Jun. 6, 1995, now abandoned, which is a continuation of application No. 08/171,527, filed on Dec. 22, 1993, now abandoned.

(30) Foreign Application Priority Data

Dec. 23, 1992 (GB) .............................. 9226879

(51) Int. Cl.$^7$ ...................... A61K 31/525; A61K 31/52; C07H 9/38
(52) U.S. Cl. ............................ 514/81; 514/86; 514/88; 544/243; 544/244
(58) Field of Search ................ 544/243, 244; 514/81, 86, 88

(56) References Cited

U.S. PATENT DOCUMENTS

| | | | |
|---|---|---|---|
| 4,950,758 A | 8/1990 | Vince et al. | 544/276 |
| 5,118,672 A | 6/1992 | Schinazi et al. | 514/47 |
| 5,159,067 A | 10/1992 | Schinazi et al. | 536/27 |
| 5,789,394 A | 8/1998 | Nguyen-Ba et al. | 514/81 |

FOREIGN PATENT DOCUMENTS

| | | |
|---|---|---|
| EP | 0 337 713 | 10/1989 |
| EP | 0 382 526 | 8/1990 |
| EP | 0 452 935 | 10/1991 |
| EP | 0 468 866 | 1/1992 |
| EP | 0 515 156 | 11/1992 |
| GB | 2230266 | * 10/1990 |
| GB | 2 230 266 | 10/1990 |
| WO | WO 92/08717 | 5/1992 |
| WO | 92/11269 | 7/1992 |

OTHER PUBLICATIONS

Otmar et al., Collect. Czech. ChemForum vol 58, pp. 2159, 1993.*

Efimtseva, Ekaterina V.; Mikhailov, Sergey N.; Meshkov, Sergey; Hankamaeki, Teemu; Oivanen, Mikko; Loennberg, Harri, J. Chem. Soc., Perkin Trans. 1 (11), 1409–15 (English) 1995.

Otmar, Miroslav; Rosenberg, Ivan; Masojidkova, Milena; Holy, Antonin, Collect. Czech. Chem. Commun., 58(9), 2180–96 (English) 1993.

Otmar, Miroslav; Rosenberg, Ivan; Masojidkova, Milena; Holy, Antonin, Collect. Czech. Chem. Commun., 58(9), 2159–79 (English) 1993.

Kim et al., Bioorg. Med. Chem. Letters, vol. 2, pp. 367–370 (1992).

J. Kraus, Nucleosides & Nucleotides, vol. 12, pp. 157–162 (1993).

Miyasaka et al., Chem. Abstracts, vol. 114, No. 122988w, p. 861 (1991).

Secrist III et al., Nucleosides & Nucleotides, vol. 11, pp. 947–956 (1992).

Starrett, Jr. et al. Antiviral Res., vol. 19, pp. 267–273 (1992).

Tanaka et al., Tetrahedron Letters, vol. 30, pp. 2567–2570 (1989).

Kurbanov et al., Russian Journal of Organic Chemistry, pp. 937–939 (1992).

Otmar et al., Collect. Czech Chem. Commun., vol. 58, pp. 2159–2179 (1993).

Otmar et al., Collect. Czech Chem. Commun., vol. 58, pp. 2180–2196 (1993).

Bedard et al. Antimicrob Agents Chemother., vol. 43 (3), pp.557–567 (1999).

Nguyen–Ba P., Bioorg Med Chem Lett., vol. 8 (24), pp.3555–3560 (1998).

Nguyen–Ba P., Bioorg Med Chem Lett., vol. 8 (24), pp.3561–3566 (1998).

Nguyen–Ba N., Nucleosides Nucleotides, vol. 18 (4–5), pp.821–827 (1999).

(List continued on next page.)

Primary Examiner—John M. Ford
(74) Attorney, Agent, or Firm—Millen, White, Zelano, Branigan, P.C.

(57) ABSTRACT

The present invention relates to a novel nucleotide analogue having the general formula (I) and pharmaceutically acceptable salts, esters, or salt of such esters:

Formula (I)

$$\begin{array}{c} R1'-O \\ | \\ R1-O-P=O \\ | \\ (CH_2)_n \end{array} \quad \begin{array}{c} R_2 \\ | \\ X \quad Z \\ * \quad * \\ Q-U \end{array}$$

wherein n, X, Q U R1', R1, Z and $R_2$ are defined here within. The compounds object of the present invention may be a single enantiomers or as mixtures of said enantiomers, the compounds may have a αD, α-L, β-D, β-L, R or S configuration at each chiral center or mixtures thereof. This invention also relates to pharmaceutical compositions containing them, alone or in combination with other therapeutic agents, and their use as antiviral agents, particularly against HIV and/or HBV infections in mammals.

49 Claims, No Drawings

OTHER PUBLICATIONS

Bednarski et al., *Biorganic & Medicinal Chemistry Letters*, vol. 5, pp. 1741–1744 (1995).
Cabasso et al., *Journal of Applied Polymer Science*, vol. 41, pp. 3025–3042 (1990).
Aly et al., *Liebigs Ann. Chem.*, pp. 127–129 (1992).
Bronson et al., *Bioorg. Med. Chem. Lett.*, pp. 685–690 (1992).
Charvet et al., *J. Med. Chem.*, vol. 37, pp. 2216–2223 (1994).
Duke et al., *Antiviral Res.*, vol. 6, pp. 299–308 (1986).

* cited by examiner

ANTIVIRAL PHOSPHONATE NUCLEOTIDES

This patent application is a continuation-in-part of U.S. patent application Ser. No. 09/411,979, filed Oct. 4, 1999, which is a divisional of Ser. No. 08/868,782, filed Jun. 4, 1997, now U.S. Pat. No. 6,005,107, which is a continuation of Ser. No. 08/868,706, filed Jun. 4, 1997, now U.S. Pat. No. 5,955,610, which is a continuation of Ser. No. 08/465,921, filed Jun. 6, 1995 (abandoned), which is a continuation of Ser. No. 08/171,527, filed Dec. 22, 1993 (abandoned). These applications are hereby incorporated by reference in their entirey.

FIELD OF THE INVENTION

The present invention relates to new nucleotide analogues. Particularly, it is concerned with the novel substituted nucleotide compounds having pharmacological activity in the treatment of viral infections in mammals.

BACKGROUND OF THE INVENTION

Infections from retroviruses and related viruses are a serious cause of disease, most notably, the acquired immunodeficiency syndrome (AIDS) and Hepatitis B virus infections. The human immunodeficiency virus (HIV) has been recognized as the etiologic agent of AIDS. Compounds having an inhibitory effect on viral multiplication or are otherwise effective in the therapy of retroviral infections are being actively sought.

HBV, while classified as a hepadnavirus rather than a retrovirus, is related to retroviruses. HBV uses a reverse transcriptase enzyme for replication, like retroviruses.

Nucleoside analogues and derivatives are an important class of therapeutic agents. For example, a number of nucleoside analogues have shown antiviral activity against retroviruses (and related viruses) such as human immunodeficiency virus (HIV), hepatitis B virus (HBV) and human T-lymphotropic virus (HTLV) (PCT publication WO 89/04662 and European Patent publication 0349242 A2). Among the nucleoside analogues shown to have antiviral activity are 3'-azido-3'-deoxythymidine (AZT), 2',3'-dideoxy-cytidine (ddC) and 2'-deoxy-3'-thiacytidine [(−)2-hydroxymethyl-5-(cytosin-1'-yl)-1,3-oxathiolane (3TC)], (European Patent publication 0382526 A2).

It is known that before nucleoside analogues can be incorporated into viral DNA, these analogues first undergo a phosphorylation step to form the triphosphorylated molecule (Jones, R. J. and Bischofbergern, N. (1995) Antiviral Res. 27:1). This is accomplished by the cell which subjects the analogue to three phosphorylations steps, the first step being rate limiting. Therefore, it is believed that, in many cases, a monophosphorylated nucleotide analogue will be incorporated with greater ease than the corresponding non-phosphorylated analogue.

Since their discovery in 1986, acyclic phosphonate nucleotide analogs have generated considerable attention as broad spectrum antiviral agents. The guanine analogues HPMPG and PMEG, the adenine analogue HPMPA, and the cytosine analogue HPMPC have been shown to exhibit good activity against human cytomegalovirus (HCMV) and herpes simplex virus (HSV). The adenine analogue PMEA has also demonstrated in vitro activity against retroviruses such as the human immunodeficiency virus (HIV), as well as DNA viruses such as HSV, and in vivo activity against murine cytomegalovirus (CMV).

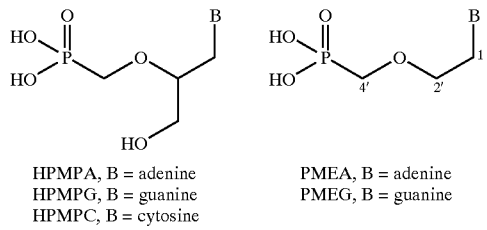

HPMPA, B = adenine
HPMPG, B = guanine
HPMPC, B = cytosine

PMEA, B = adenine
PMEG, B = guanine

Unfortunately, these compounds present problems due to their cytotoxicity, particularly, PMEG is very cytotoxic. Cyclic phosphonate nucleotides related to HPMPA have been synthesized but exhibited little or no antiviral activity (Collect. Chez. Chem. Commun. (1993) 58: 2159–2191).: These compounds have been reported to exhibit little or no activity against some DNA viruses and no activity against retroviruses and RNA viruses.

In order to facilitate the uptake of the phosphorylated nucleotide analogues and increase their bioavailability, several neutral monophosphorylated nucleotide prodrugs have been developed. These neutral nucleotides are more lipophilic due to the masking of the negative charge of the phosphate group with enzyme or pH labile neutral substitutes. This allows the prodrug to penetrate the cell membrane much more readily than their corresponding 5'-monophosphate dianion counterpart. Once inside the cell, the prodrug decomposes to generate the original monophosphorylated nucleotide analogue which can then be further phophorylated and incorporated into the viral DNA. To achieve this result several substituents have been developed for use in the preparation of monophosphorylated nucleotide prodrugs. Examples of these substituents include S-acyl-2-thioethyls (SATE) (J. Med. Chem. (1995) 38:3941–3950, Antiviral Chem. Chemother. (1998) 9(1):41–52.) such as methyl (SATE), isopropyl(SATE), t-butyl(SATE) and phenyl(SATE), or carboxyloxymethyl such as pivaloyloxymethyl (POM) (Antiviral Chem. Chemother (1994) 5:91–98) and di-S-[(2-hydroxyethyl)sulfidyl]-2-thioethyl. Additionally, substituents such as alkyl methyl carbonates, for example isopropyl methyl carbonate (POC), have also been used to form alkylmethyl carbamate prodrugs (Antiviral Chem. Chemother. (1997) 8: 557–564). Recently, an alternative approach has been developed by the synthesis of phenyl and benzylphosphotriesters analogues (Bioorg. Med. Chem. Lett. (1997) 7: 99–104) and phophostriesters analogues (WO98/17281) of nucleotides have been prepared exhibiting antiviral activity.

SUMMARY OF THE INVENTION

The present invention relates to novel nucleotide analogues having the general formula (I):

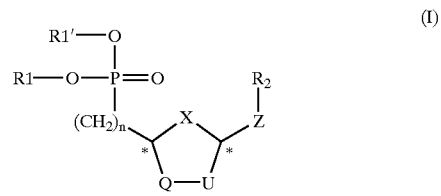

(I)

and pharmaceutically acceptable derivatives thereof, for example, pharmaceutically acceptable salts, esters, or salts of such esters, wherein n is 0 or 1;

X is O, S, $CH_2$, CH-halogen, CH—$N_3$, or C=$CH_2$;

Q and U are independently selected from S, O, $CF_2$, C=$CH_2$. $CH(R_a)$ or U and Q are both CH and Q and U are linked by a double bond;

$R_a$ is hydrogen, OH, CN, halogen, $N_3$, $NH_2$, SH, $C_{1-6}$ alkyl, $C_{1-6}$ alkoxy, $C_{2-6}$ alkenyl, $C_{2-6}$ alkynyl, $C(O)R_b$, $NHR_b$, or $SR_b$;

$R_b$ is hydrogen, OH, CN, halogen, $N_3$, $NH_2$, SH, $C_{1-6}$ alkyl, $C_{1-6}$ acyl, or $C(O)OR_c$;

$R_c$ is $C_{1-6}$ alkyl or $C_{1-6}$ acyl;

Z is $(CH_2)_m$ wherein m is 1;

R1 and R1' are independently selected from H, $C_{1-6}$ alkyl, $C_{2-6}$ alkenyl, $C_{6-10}$ aryl, $C_{7-11}$ arylmethyl, $C_{2-7}$ acyloxymethyl, $C_{3-8}$ alkoxycarbonyloxymethyl, $C_{7-11}$ aryloyloxymethyl, $C_{3-8}$ S-acyl-2-thioethyl, phosphate or diphosphate;

$R_2$ is a purine or pyrimidine base or a derivative thereof, provided that when $R_2$ is adenine, $R_a$ is CN, halogen, $N_3$, $NH_2$, SH, $C_{1-6}$ alkyl, $C_{2-6}$ alkenyl, $C_{2-6}$ alkynyl, $C(O)R_b$, $NHR_b$, $SR_b$ wherein $R_b$ is hydrogen, OH, CN, halogen, $N_3$, $NH_2$, SH, $C_{1-6}$ alkyl.

The present invention also includes methods and compositions for the treatment of viral infections in mammals. Particularly, methods and compositions for the treatment of infections by retroviruses and related viruses. Of special interest are methods and compositions for the treatment of acquired immunodeficiency syndrome (AIDS) and/or Hepatitis B virus infections in mammals.

The present inventions also includes compositions which contains mixtures of compounds of the present invention active against viral infections as well as combinations of compounds of the present invention active against viral infections and other therapeutic agents.

DETAILED DESCRIPTION OF THE INVENTION

The present invention relates to a novel nucleotide analogue having the general formula (I):

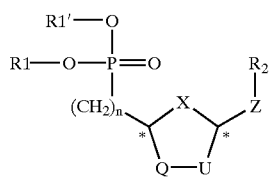

(I)

and pharmaceutically acceptable derivatives thereof, for example, pharmaceutically acceptable salts, esters, or salts of such esters, wherein n is 0 or 1;

X is O, S, $CH_2$, CH-halogen, CH—$N_3$, or C=$CH_2$;

Q and U are independently selected from S, O, $CF_2$, C=$CH_2$. $CH(R_a)$ or U and Q are both CH and Q and U are linked by a double bond;

$R_a$ is hydrogen, OH, CN, halogen, $N_3$, $NH_2$, SH, $C_{1-6}$ alkyl, $C_{1-6}$ alkoxy, $C_{2-6}$ alkenyl, $C_{2-6}$ alkynyl, $C(O)R_b$, $NHR_b$, or $SR_b$;

$R_b$ is hydrogen, OH, CN, halogen, $N_3$, $NH_2$, SH, $C_{1-6}$ alkyl, $C_{1-6}$ acyl, or $C(O)OR_c$;

$R_c$ is $C_{1-6}$ alkyl or $C_{1-6}$ acyl;

Z is $(CH_2)_m$ wherein m is 1;

R1 and R1' are independently selected from the group H, $C_{1-6}$ alkyl, $C_{2-6}$ alkenyl, $C_{6-10}$ aryl, $C_{7-11}$ arylmethyl, $C_{2-7}$ acyloxymethyl, $C_{3-8}$ alkoxycarbonyloxymethyl, $C_{7-11}$ aryloyloxymethyl, $C_{3-8}$ S-acyl-2-thioethyl, phosphate or diphosphate;

$R_2$ is a purine or pyrimidine base or derivative thereof, provided that when $R_2$ is adenine, $R_a$ is CN, halogen, $N_3$, $NH_2$, SH, $C_{1-6}$ alkyl, $C_{2-6}$ alkenyl, $C_{2-6}$ alkynyl, $C(O)R_b$, $NHR_b$, $SR_b$ wherein $R_b$ is hydrogen, OH, CN, halogen, $N_3$, $NH_2$, SH, $C_{1-6}$ alkyl.

The compounds of the present invention may be in the form of single enantiomers having a α-D, α-L, β-D, β-L, R or S configuration at each chiral center, or a mixture thereof, e.g., a racemic mixture.

The present invention additionally includes the use of compounds of formula (I) in the treatment of viral infections in mammals. Particularly, the invention includes the use of the nucleotides of formula (I) in the treatment of viral infections caused by the human immunodeficiency virus (HIV) and the hepatitis B virus (HBV) in mammals. The compounds of the present invention may be used alone or in combination with one or more therapeutic agents in the treatment of a viral infection.

Additionally, the invention includes the use of the nucleotides of this invention in the preparation of antiviral formulations or the preparation of a medicament for viral infections.

The invention relates to a novel class of phosphonate nucleotide analogues having the general formula (I) and pharmaceutically acceptable derivatives thereof. Members of this series of analogues possess anti-viral activity against retroviruses, such as HIV, and related viruses, such as HBV.

The term "alkyl", as used herein, unless otherwise specified, refers to a saturated straight, branched, or cyclic, primary, secondary, or tertiary hydrocarbon of $C_{1-30}$, particularly $C_{1-6}$, unsubstituted or optionally mono- or di-substituted by hydroxy, $N_3$, CN, SH, amino, halogen (F, Cl, Br, I), $C_{6-12}$ aryl, $C_{2-12}$ alkoxyalkyl or nitro. It specifically includes methyl, ethyl, cyclopropyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "acyl", as used hereinafter, refers to a radical derived from an aliphatic carboxylic acid, by removal of the —OH group of 1 to 30 carbon atoms, particularly 1 to 6 carbon atoms. Like the acid to which it is related, an aliphatic acyl radical may be substituted (by a hydroxy, $N_3$, CN, halogen (F, Cl, Br, I), $C_{6-12}$ aryl, $C_{1-6}$ alkyl, $C_{2-12}$ alkoxyalkyl or nitro) or unsubstituted, and whatever the structure of the rest of the molecule may be, the properties of the functional group remain essentially the same (e.g., acetyl, propionyl, isobutanoyl, pivaloyl, hexanoyl, butyryl, pentanoyl, 3-methylbutyryl, hydrogen succinate, mesylate, valeryl, caproic, caprylic, capric, lauric, myristic, palmitic, stearic, oleic, 3-chlorobenzoate, trifluoroacetyl, chloroacetyl, and cyclohexanoyl).

The terms "alkenyl" and "alkynyl" represent substituted (by $NH_2$, SH, $N_3$, CN, halogen, hydroxyl or $C_{6-20}$ aryl) or unsubstituted straight, branched or cyclic hydrocarbon chains having 2 to 30 carbon atoms and preferably from 2 to 6 carbon atoms and containing at least one unsaturated group (e.g. allyl, vinyl ).

The term "alkoxy" represents a substituted (by hydroxy, $N_3$, CN, SH, amino, halogen (F, Cl, Br, I), $C_{6-12}$ aryl, $C_{2-12}$ alkoxyalkyl or nitro) or unsubstituted alkyl group containing from 1 to 30 carbon atoms and preferably from 1 to 6 carbon atoms, wherein the alkyl group is covalently bonded through an oxygen atom (e.g., methoxy and ethoxy). The substituents include those listed above in the description of alkyl groups.

The term "aryl" represents a aromatic moiety which may be unsubstituted or substituted by hydroxy, $N_3$, CN, halogen (F, Cl, Br, I), SH, amino, trifluoromethyl, $C_{1-6}$ alkyl, $C_{1-5}$ alkoxy, $C_{6-12}$ aryl, $C_{1-6}$ alkyl, $C_{2-12}$ alkoxyalkyl or nitro, and containing at least one benzenoid-type ring. The group may contain from 6 to 14 carbon atoms (e.g., phenyl and naphthyl), particularly 6 to 10 carbon atoms.

The term "aryloxy" represents a substituted (as described above for aryl, e.g., by a halogen, trifluoromethyl or $C_{1-5}$ alkoxy) or unsubstituted aryl moiety, having 6 to 14 carbon atoms, covalently bonded through an oxygen atom (e.g., benzyloxy, phenoxy).

The term "arylalkyl" or "aralkyl" represents a substituent comprising an aryl moiety attached via an alkyl chain (e.g. benzyl, phenylethyl) wherein the sum total of carbon atoms for the aryl moiety and the alkyl chain is 7 to 21. The aryl portion or alkyl chain portion of the group are unsubstituted or optionally mono- or di-substituted with OH, SH, amino, or halogen. The aryl portion can also be substituted as described above for aryl, e.g., by $C_{1-6}$ alkyl.

The term "thiol" represents $C_{1-6}$ alkyl, $C_{6-15}$ aryl, $C_{7-21}$ aralkyl, $C_{2-6}$ alkenyl or $C_{2-6}$ alkynyl groups covalently bonded to an adjacent sulfur atom bearing a hydrogen.

The term "alkylthio" (e.g. thiomethy, thioethyl) refers to $C_{1-6}$ alkyl, unsubstituted or optionally mono- or di-substituted by hydroxy, halogen (F, Cl, Br, I), $C_{6-12}$ aryl, $C_{1-6}$ alkyl, $C_{2-12}$ alkoxyalkyl or nitro, covalently bonded to an adjacent sulfur atom.

The term "arylthio" (e.g. thiophenyl, thiobenzyl), refers to $C_{6-10}$ aryl groups, unsubstituted or optionally mono- or di-substituted by substituents as described above for aryl, e.g., hydroxy, halogen (F, Cl, Br, I), $C_{6-12}$ aryl, $C_{1-6}$ alkyl, $C_{2-12}$ alkoxyalkyl or nitro, covalently bonded to an adjacent sulfur atom.

The term "acyloxy" refers to an acyl group having a 1 to 30 carbon atom chain, particularly 1 to 6 carbon atoms, which is bonded through an oxygen atom and can be saturated or unsaturated, and straight or branched (e.g.: acetyloxy). The chain may be unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro.

The term "alkoxycarbonyl" refers to an alkoxy group having a 1 to 30 carbon atoms chain, particularly 1 to 6 carbon atoms, which can be saturated or unsaturated, straight or branched (e.g.: $CH_3O-CO-$) that is bonded through a carbonyl group. The chains may be unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro.

The term "alkoxyalkyl" represents a $C_{1-6}$ alkoxy group attached to an adjacent $C_{1-6}$ alkyl group (e.g., methoxymethyl, ethoxymethyl). They may be unsubstituted or optionally mono- or di-substituted by hydroxy, $N_3$, CN, SH, amino, halogen (F, Cl, Br, I), $C_{6-12}$ aryl, $C_{1-6}$ alkyl, $C_{1-6}$ alkoxy or nitro.

The term "heterocycle" represents a saturated or unsaturated mono- or polycyclic (e.g. bicyclic) ring incorporating 1 or more (e.g.:1–4) heteroatoms selected from N, O and S. It is understood that a heterocycle is optionally mono- or di-substituted with OH, SH, halogen, $CF_3$, oxo or $C_{1-6}$ alkyl. Examples of suitable monocyclic heterocycles include but are not limited to pyridine, piperidine, pyrazine, piperazine, triazine, pyrimidine, imidazole, thiazole, oxazole, furan, thiofuran, pyran and thiophene. Examples of suitable bicyclic heterocycles include but are not limited to indole, benzimidazole, quinoline, isoquinoline, purine, and carbazole.

The term "amino" represents $NH_2$ or an amino substituted by one or two $C_{1-6}$ alkyl, $C_{6-10}$ aryl, $C_{2-6}$ alkenyl, $C_{2-6}$ alkynyl, or $C_{7-12}$ aralkyl groups, which groups are unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro, wherein the carbon atoms are covalently bonded to an adjacent element through a nitrogen atom (e.g. pyrrolidine). They include primary, secondary and tertiary amines and quaternary ammonium salts.

It will be appreciated by those skilled in the art that the compounds of formula (I) contain at least two chiral centers (shown as * in formula (I)) and thus exist in the form of two pairs of optical isomers (i.e. enantiomers) and mixtures thereof including racemic mixtures. Thus the compounds of formula (I) may be either cis isomers, as represented by formula (IA), or trans isomers, as represented by formula (IB), or mixtures thereof. Each of the cis and trans isomers can exist as one of two enantiomers, R or S at each chiral center, or as mixtures thereof including racemic mixtures. Depending on the substitution of U or Q compounds of the present inventions may have a third and/or fourth chiral center. The position of the substituents in these chiral centers will have an effect on the antiviral characteristics of the compound object of the present invention. All such isomers and mixtures thereof including racemic mixtures are included within the scope of the invention.

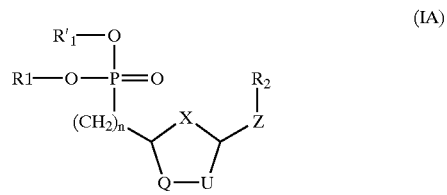

(IA)

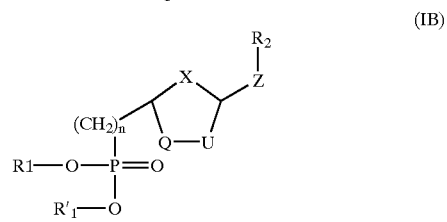

(IB)

By purine or pyrimidine base derivative is meant a naturally occurring purine or pyrimidine base which mimics such bases in that their structures (the kinds of atoms and their arrangement) are similar to the normal bases but may possess additional or lack certain of the functional properties of the normal bases. Derivatives of such bases or analogues include those obtained by replacement of a CH moiety by a nitrogen atom (for example, 5-azapyrimidines such as 5-azacytosine) or vice versa (for example 7-deazapurines, such as 7-deazadenine or 7-deazaguanine) or both (e.g. 7-deaza, 8-azapurines) or may have ring substituted by halogen, hydroxyl, azido, cyano, amino, substituted amino, thiol, $C_{1-6}$ alkyl and $C_{6-10}$ aryl.

By the term "pharmaceutically acceptable derivative" of a compound is meant any pharmaceutically acceptable salt, ester, or salt of such ester of a compound of formula (I), or any other compound which, upon administration to the recipient, is capable of providing (directly or indirectly) a compound of formula (I) or an antivirally active metabolite or residue thereof. It will be appreciated by those skilled in the art that the compounds of formula (I) may be modified to provide pharmaceutically acceptable derivatives thereof, at functional groups in the base moiety. Modifications at all such functional groups are included within the scope of the invention.

Conveniently, the group $R_2$ is selected from:

A) 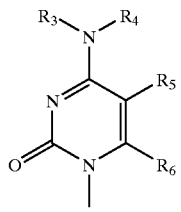

B) 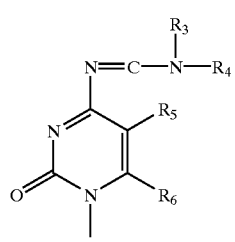

C) 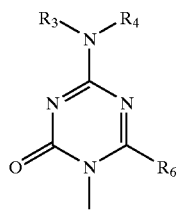

D) 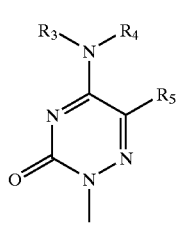

E) 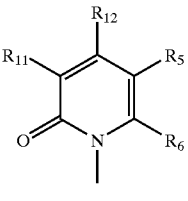

F) 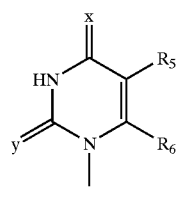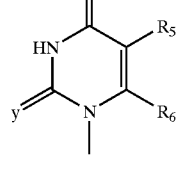

G) 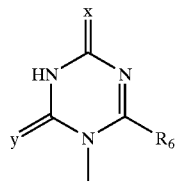

H) 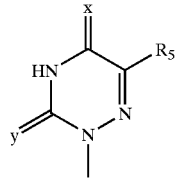

I) 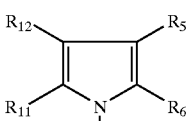

J) 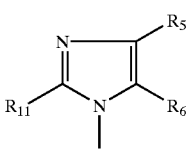

K) 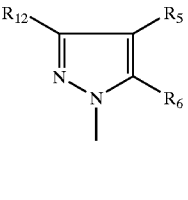

L)

wherein:
x is oxygen, NH or sulfur.
y is oxygen, NH or sulfur.
$R_3$ and $R_4$ are independently selected from hydrogen, hydroxyl, amino, $C_{1-6}$ alkyl, $C_{2-6}$ alkenyl, $C_{2-6}$ alkynyl, $C_{1-10}$ acyl, $C_{6-10}$ aryl, $C_{6-11}$ arylcarbonyl, $C_{2-7}$ alkoxycarbonyl, $C_{6-11}$ aryloxycarbonyl, $C_{2-7}$ alkylaminocarbonyl, or amino acids.
$R_3$ may be a saturated or unsaturated $C_{3-8}$ carbocyclic ring optionally substituted with COOH, C(O)NH$_2$, OH, SH, NH$_2$, NO$_2$, $C_{1-6}$ alkyl, $C_{2-6}$ alkenyl, $C_{2-6}$ alkynyl, halogen, C(O)R$_{13}$ wherein R$_{13}$ is a $C_{1-6}$ alkyl, $C_{2-6}$ alkenyl, $C_{2-6}$ alkynyl and C(O)OR$_{14}$ wherein R$_{14}$ is a $C_{1-6}$ alkyl, $C_{2-6}$ alkenyl, $C_{2-6}$ alkynyl; and $R_4$ is chosen from H, $C_{1-6}$ alkyl, $C_{2-6}$ alkenyl and $C_{2-6}$ alkynyl.
$R_3R_4$ can also be connected to the nitrogen atom to form a saturated or unsaturated $C_{3-8}$ heterocyclic ring optionally substituted with C(O)OH, C(O)NH$_2$, OH, SH, NH$_2$, NO$_2$, $C_{1-6}$ alkyl, $C_{2-6}$ alkenyl, $C_{2-6}$ alkynyl, halogen, C(O)R$_{13}$ wherein R$_{13}$ is a $C_{1-6}$ alkyl, $C_{2-6}$ alkenyl, $C_{2-6}$ alkynyl and $C(O)OR_{14}$ wherein $R_{14}$ is a $C_{1-6}$ alkyl, $C_{2-6}$ alkenyl, $C_{2-6}$ alkynyl.

$R_5$, $R_6$, $R_{11}$, and $R_{12}$ are each independently selected from hydrogen, halogen, hydroxyl, amino, cyano, carboxyl, carbamoyl, $C_{2-7}$ alkoxycarbonyl, hydroxymethyl, trifluoromethyl, $C_{6-10}$ arylthio which is unsubstituted or substituted by, e.g., halogen or azido, $C_{1-6}$ alkyl which is unsubstituted or substituted by, e.g., halogen or azido, $C_{2-6}$ alkenyl which is unsubstituted or substituted by, e.g., halogen or azido, $C_{2-6}$ alkynyl which is unsubstituted or substituted by, e.g., halogen or azido, $C_{1-6}$ acyloxy, thiocarboxy, thiocarbamoyl, carbamate, ureido, amidino, or $C_{6-10}$ aryloxy.

Alternatively, Group $R_2$ is selected from:

M)
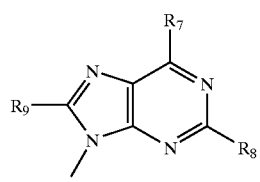

N)
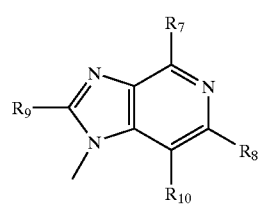

O)
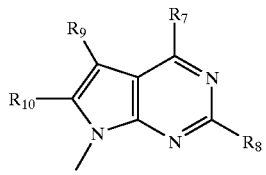

P)
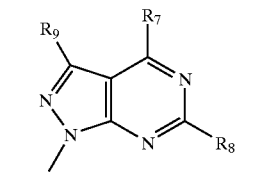

Q)
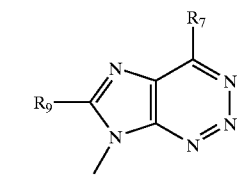

R)
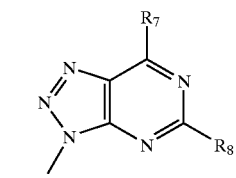

S)
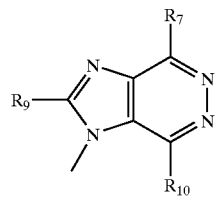

T)
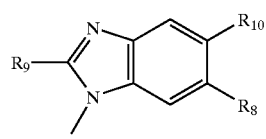

U)
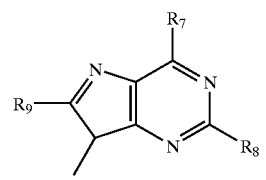

V)
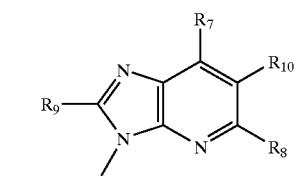

wherein:
$R_7$, $R_8$, $R_9$, and $R_{10}$ are each independently selected from the group is chosen from hydrogen, hydroxy, $C_{1-6}$ alkoxy, thiol, $C_{1-6}$ alkylthio, amino, amino substituted by, for example, a structure in accordance with formulas (II)-(IV), halogen, azido, cyano, carboxyl, $C_{2-7}$ alkoxycarbonyl, carbamoyl, $C_{1-6}$ alkyl, $C_{2-6}$ alkenyl, or $C_{2-6}$ alkynyl, $C_{1-6}$ acyloxy, $C_{6-10}$ aryl, $C_{6-10}$ aryloxy, $C_{1-6}$ thiocarboxy, thiocarbamoyl, carbamate, ureido, amidino, $C_{6-10}$ aryloyloxy or -$NR_{19}R_{20}$ wherein:
$R_{19}$ is H, a saturated or unsaturated $C_{3-6}$ carbocyclic ring optionally substituted with COOH, $C(O)NH_2$, OH, SH, $NH_2$, $NO_2$, $C_{1-6}$ alkyl, $C_{2-6}$ alkenyl, $C_{2-6}$ alkynyl, halogen, $C_{1-6}$ acyl, $C_{6-10}$ aryl, $C(O)R_{21}$ wherein $R_{21}$ is a $C_{1-6}$ alkyl, $C_{2-6}$ alkenyl, $C_{2-6}$ alkynyl or $COOR_{22}$ wherein $R_{22}$ is $C_{1-6}$ alkyl, $C_{2-6}$ alkenyl, or $C_{2-6}$ alkynyl; and $R_{20}$ is chosen from H, $C_{1-6}$ alkyl, $C_{2-6}$ alkenyl and $C_{2-6}$ alkynyl.

$R_{19}R_{20}$ can also be connected to the nitrogen atom to form a saturated or unsaturated $C_{3-6}$ heterocyclic ring optionally substituted with COOH, $C(O)NH_2$, OH, SH, $NH_2$, $NO_2$, $C_{1-6}$ alkyl, $C_{2-6}$ alkenyl, $C_{2-6}$ alkynyl, halogen, $C(O)R_{21}$ wherein $R_{21}$ is a $C_{1-6}$ alkyl, $C_{2-6}$ alkenyl, $C_{2-6}$ alkynyl or $COOR_{22}$ wherein $R_{22}$ is a $C_{1-6}$ alkyl, $C_{2-6}$ alkenyl or $C_{2-6}$ alkynyl.

In an alternative embodiment of the present invention $R_7$ is represented by H, F, I, Br, Cl, $NH_2$, OH or the formula (II)
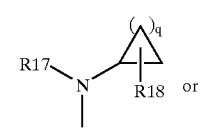

-continued

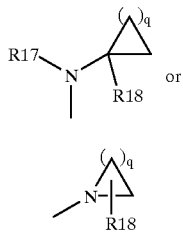 (III)

or

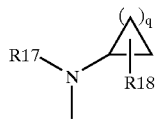 (IV)

wherein q is an integer selected from 1 to 4

R18 is selected from the group comprising H, COOH, C(O)NH$_2$, OH, SH, NH$_2$, NO$_2$, N$_3$, C$_{1-6}$ alkyl, C$_{2-6}$ alkenyl, C$_{2-6}$ alkynyl, halogen, C(O)Rd wherein Rd is a C$_{1-6}$ alkyl, C$_{2-6}$ alkenyl, C$_{2-6}$ alkynyl and C(O)ORe wherein Re is C$_{1-6}$ alkyl or C$_{2-6}$ alkenyl, C$_{2-6}$ alkynyl; and R17 is H or a C$_{1-6}$ alkyl, C$_{2-6}$ alkenyl, C$_{2-6}$ alkynyl.

In an alternative embodiment, q is 1 or 2, R17 is H or methyl, and R18 is H, C(O)OH, C(O)NH$_2$, C$_{1-6}$ alkyl, C$_{2-6}$ alkenyl, C$_{2-6}$ alkynyl and C(O)ORd wherein Rd is C$_{1-6}$ alkyl, C$_{2-6}$ alkenyl or C$_{2-6}$ alkynyl.

In an alternate embodiment of the present invention, q is 1, R17 is H and R18 is H, COOH, or C$_{1-6}$ alkyl.

In an additional embodiment of the present invention R18 is H, COOH, methyl or ethyl.

In an additional embodiment of the present invention R18 is methyl or ethyl.

In an additional embodiment of the present invention, R18 is COOH.

In an additional embodiment of the present invention R18 is H.

In an additional embodiment of the present invention, R17 is H or methyl and R18 is H.

In an additional embodiment of the present invention R18 and R17 are H.

In an alternate embodiment R$_8$, R$_9$, and R$_{10}$ are each independently chosen from hydrogen, hydroxy, amino, substituted amino, halogen, azido or methyl.

The compounds of the present invention include those wherein R$_7$ is Cl, hydroxyl, NH$_2$ or the formula

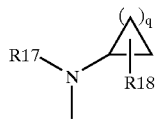

wherein q is an integer selected from 1 or 2;

R18 is selected from H or C(O)OH;

R$_8$, R$_9$, R$_{10}$ and R17 are hydrogen; and

R$_5$ is F, I, Cl, or CH$_3$.

In another embodiment of the present invention, R$_2$ is chosen from formulas:

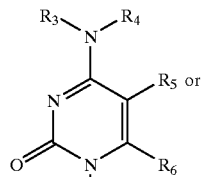 A)

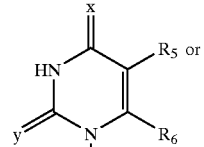 F)

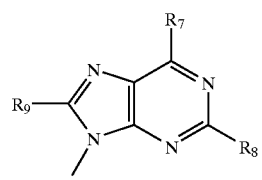 M)

Wherein

R$_3$, R$_4$, and R$_6$ are H;

R$_5$ is H, F, Cl, I, Br, hydroxyl or amino;

x and y are O or S;

R$_7$ is H, F, Cl, I, Br, hydroxyl, amino or the formula

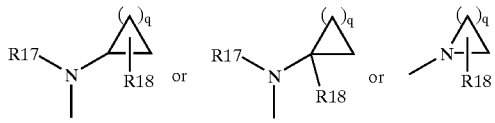

wherein:

q is an integer selected from 1 or 2;

R17 is H or methyl;

R18 is H, COOH, or C$_{1-6}$ alkyl;

and R$_8$ and R$_9$ are each independently chosen from hydrogen, hydroxyl, amino, substituted amino, halogen, azido or methyl.

Additionally the present invention includes compound wherein R$_2$ is selected from cytosine, adenine, guanine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine.

The purine or pyrimidine base R$_2$ is linked through the linker "Z" at any position on the base, but preferably at N9- for the purines, or N1- or N3-position for the pyrimidines.

In an alternate embodiment of the present invention compounds of formula (I) are in the cis configuration.

In an alternate embodiment of the present invention, compounds of formula (I) have both Z(R$_2$) and (CH$_2$)$_n$P(O)O$_2$R1R1' are both in either the R or S configuration.

In an alternate embodiment of the present invention, compounds of formula (I) have Z(R$_2$) and (CH$_2$)$_n$P(O)O$_2$R1R1' in the cis configuration. In an additional embodiment, compounds of formula (I) have Z(R$_2$), (CH$_2$)$_n$P(O)O$_2$R1R1' and R$_a$ in the cis configuration.

In an alternative embodiment of the present invention the following elements of the compounds of formula (I) are chosen:

X is O;

Q is CH$_2$;

U is chosen from: C=CH$_2$ or CH(R$_a$) wherein R$_a$ is hydrogen, OH, CN, halogen, N$_3$, NH$_2$, SH, C$_{1-6}$ alkyl which is unsubstituted or substituted by OH, F, I Cl, Br, NH$_2$ or SH, C$_{2-6}$ alkenyl which is unsubstituted or substituted by OH, F, I Cl, Br, NH$_2$ or SH, C$_{2-6}$ alkynyl which is unsubstituted or substituted by OH, F, I Cl, Br, NH$_2$ or SH, C(O) R$_b$, NHR$_b$ or SR$_b$ wherein R$_b$ is hydrogen, OH, CN, halogen, N$_3$, NH$_2$, SH, C$_{1-6}$ alkyl ,C$_{1-6}$ acyl, or C(O)OR$_C$ wherein R$_C$ is C$_{1-6}$ alkyl;

Z is (CH$_2$)$_m$ wherein m is 1;

R1 and R1' are independently selected from hydrogen, C$_{2-7}$ acyloxymethyl, C$_{3-8}$ alkoxycarbonyloxymethyl, phenyl, benzyl, C$_{3-8}$ S-acyl-2-thioethyl, phosphate or diphosphate;

R$_2$ is chosen from formulas (A), (B), (C), (D), (E), (F), (G), (H), (L) and (M), (N), (O), (P), (R), (S), (T) wherein R$_3$, R$_4$, R$_5$, R$_6$, R$_7$, R$_8$, R$_9$, R$_{10}$, R$_{11}$, and R$_{12}$ are defined herein above, provided that when R$_2$ is adenine, R$_a$ is CN, halogen, N$_3$, NH$_2$, SH, C$_{1-6}$ alkyl which is unsubstituted or substituted by OH, F, I Cl, Br, NH$_2$ or SH, C$_{1-6}$ alkenyl which is unsubstituted or substituted by OH, F, I Cl, Br, NH$_2$ or SH, C$_{2-6}$ alkynyl which is unsubstituted or substituted by OH, F, I Cl, Br, NH$_2$ or SH, C(O)R$_b$, NHR$_b$, SR$_b$ wherein R$_b$ is hydrogen, OH, CN, halogen, N$_3$, NH$_2$, SH, C$_{1-6}$ alkyl In an optional embodiment of the present invention, the compounds of formula (I) are in the cis configuration and X is O;

Q is either CH$_2$ or CH;

U is CH(R$_a$) wherein R$_a$ is chosen from hydrogen, OH, CN, F, Cl, I, Br, N$_3$, NH$_2$, SH, C$_{1-6}$ alkyl, C$_{2-6}$ alkenyl, C$_{2-6}$ alkynyl, C(O)R$_b$, NHR$_b$, SR$_b$ wherein R$_b$ is hydrogen, OH, CN, halogen, N$_3$, NH$_2$, SH, C$_{1-6}$ alkyl or Cl$_6$ acyl, C(O)OR$_C$ wherein R$_c$ is C$_{1-6}$ alkyl or C$_{1-6}$ acyl, or U is CH provided that Q is CH and Q and U are linked by a double bond;

Z is (CH$_2$)$_m$ wherein m is 1;

R1 and R1' are each independently chosen from hydrogen, phosphate or diphosphate; and R$_2$ is chosen from formulas:

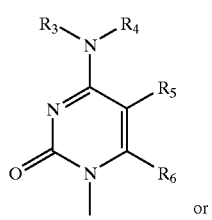

A)

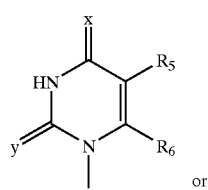

F)

-continued

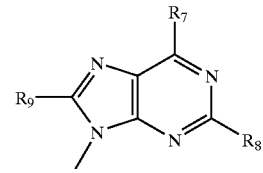

M)

Wherein
R$_3$, R$_4$, and R$_6$ are H;
R$_5$ is H, F, Cl, I, Br, hydroxyl or amino;
x and y are independently selected from O or S;
R$_7$ is H, F. Cl, I, Br, hydroxyl, amino or the formula

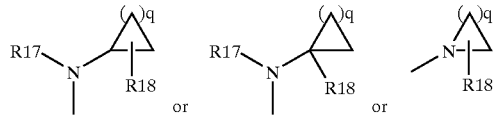

wherein:
q is an integer selected from 1 or 2;
R17 is H or methyl;
R18 is H, COOH, or C$_{1-6}$ alkyl;
and R$_8$ and R$_9$ are each independently chosen from hydrogen, hydroxyl, amino, substituted amino, halogen, azido or methyl.

In an alternative embodiment the compounds of formula (I) of the present invention are in the cis configuration and are chosen from those wherein X is O;

U is C=CH$_2$, CH—OH, CH—F, CH—Cl, CH—Br, CH—I or CH—N$_3$;

Q is CH$_2$;

Z is (CH$_2$)$_m$ wherein m is 1;

R1 and R1' are hydrogen, phosphate or diphosphate; and

R$_2$ is chosen from formulas:

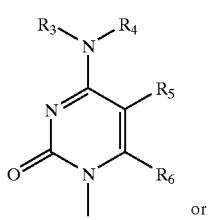

A)

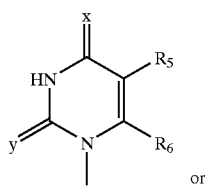

F)

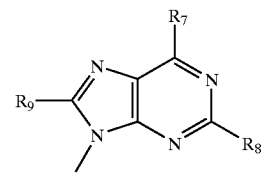

M)

Wherein
$R_3$, $R_4$, $R_6$ and $R_9$ are H;
$R_5$ is H, F, Cl, I, Br, hydroxyl, methyl or amino;
x and y are O or S;
$R_7$ is H, F, Cl, I, Br, hydroxyl, amino or the formula:

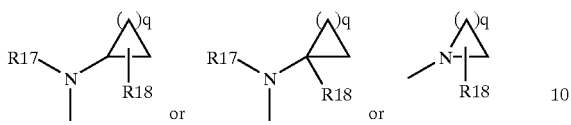

wherein:
q is an integer selected from 1 or 2;
R17 is H or methyl;
R18 is H, COOH, or $C_{1-6}$ alkyl;
and R8 is amino, provided that when $R_2$ is adenine, U is C=$CH_2$, CH—F, CH—Cl, CH—Br, CH—I, C—$NH_2$ or CH—$N_3$.

Alternatively, an embodiment of the present invention is represented by compounds of formula (I) wherein:
X is O;
Q is $CH_2$;
U is chosen from $CH_2$, C=$CH_2$, CH—OH, CH—F, CH—Cl, CH—Br, CH—I, C—$NH_2$ or CH—$N_3$;
Z is $(CH_2)_m$ wherein m is 1;
$R_1$ and R1' are hydrogen, phosphate or diphosphate;
$R_2$ is cytosine, adenine, guanine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine, provided that when $R_2$ is adenine, U is C=$CH_2$, CH—F, CH—Cl, CH—Br, CH—I, C—$NH_2$ or CH—$N_3$.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, p-toluenesulphonic, tartaric, acetic, citric, methanesulphonic, formic, benzoic, malonic, naphtalene-2-sulphonic and benzenesulphonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $N(R')_4^+$ (where R' is $C_{1-4}$ alkyl) salts.

References hereinafter to a compound according to the invention includes both the compound of formula (I) and its pharmaceutically acceptable derivatives.

Compounds of formula (I) include:

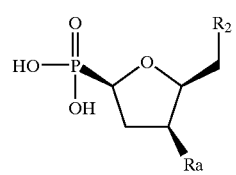 (i)

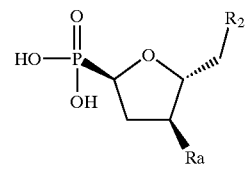 (ii)

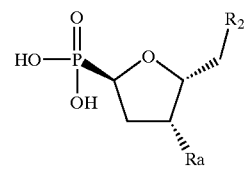 (iii)

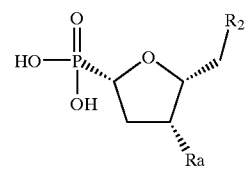 (iv)

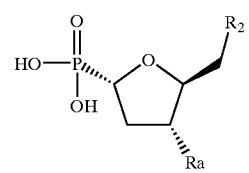 (v)

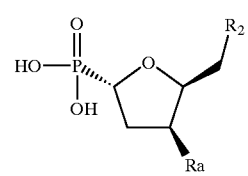 (vi)

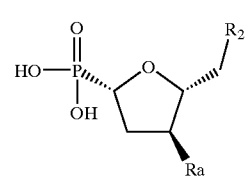 (vii)

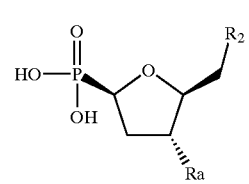 (viii)

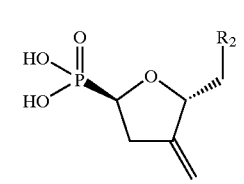 (ix)

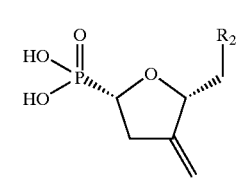 (x)

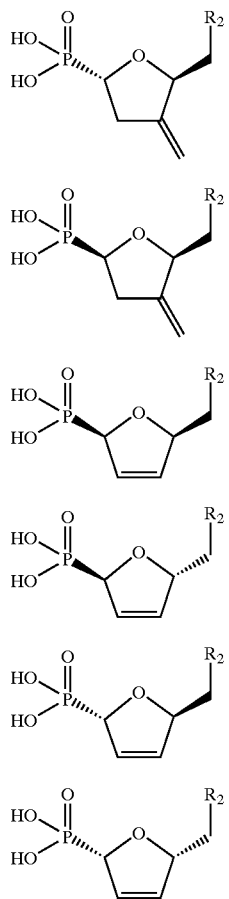

Wherein:
R₂ is cytosine, adenine, guanine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine; and $R_a$ is H, OH, CN, F, Cl, Br, I, NH₂ or N₃, provided that when R₂ is adenine, $R_a$ is CN, F, Cl, Br, I, N₃ or NH₂.

In an alternative embodiment of the present invention, compounds of formula (I) are selected for formulas (i), (iv), (vii), (viii), (x), (xii), (xiii), or (xvi), wherein R₂ is chosen from cytosine, adenine, guanine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine; and Ra is OH, F, Cl, Br, I or N₃, provided that when R₂ is adenine Ra is F, Cl, Br, I or N₃.

Specific compounds of formula (I) include:

(5R)-(2-amino-6-hydroxy-purin-9-ylmethyl)-(4S)-azido-tetrahydro-furan-(2S)-phosphonate.

(5R)-(2-amino-6-hydroxy-purin-9-ylmethyl)-(4R)-azido-tetrahydro-furan-(2S)-phosphonate.

(5R)-(2-amino-6-hydroxy-purin-9-ylmethyl)-(4S)-azido-tetrahydro-furan-(2R)-phosphonate.

(5R)-(2-amino-6-hydroxy-purin-9-ylmethyl)-(4R)-azido-tetrahydro-furan-(2R)-phosphonate.

(5R)-(2-amino-6-hydroxy-purin-9-ylmethyl)-(4R)-fluoro-tetrahydro-furan-(2S)-phosphonate.

(5R)-(2-amino-6-hydroxy-purin-9-ylmethyl)-(4R)-fluoro-tetrahydro-furan-(2R)-phosphonate.

(5R)-(2-amino-6-hydroxy-purin-9-ylmethyl)-(4S)-fluoro-tetrahydro-furan-(2S)-phosphonate.

(5R)-(2-amino-6-hydroxy-purin-9-ylmethyl)-(4S)-fluoro-tetrahydro-furan-(2R)-phosphonate.

(5R)-(2-ami no-6-hyd roxy-purin-9-ylmethyl)-(4S)-hyd roxy-tetrahyd ro-fu ran-(2S)-phosphonate (5R)-(2-amino-6-hydroxy-purin-9-ylmethyl)-(4R)-hydroxy-tetrahydro-furan-(2R)-phosphonate (5R)-(2-amino-6-hydroxy-purin-9-ylmethyl)-(4S)-hydroxy-tetrahydro-furan-(2R)-phosphonate (5R)-(2-amino-6-hydroxy-purin-9-ylmethyl)-(4R)-hydroxy-tetrahydro-furan-(2S)-phosphonate (5R)-(2-amino-6-hydroxy-purin-9-ylmethyl)-(4R)-iodo-tetrahydro-furan-(2S)-phosphonate.

(5R)-(2-amino-6-hydroxy-purin-9-ylmethyl)-(4R)-iodo-tetrahydro-furan-(2R)-phosphonate.

(5R)-(2-amino-6-hydroxy-purin-9-ylmethyl)-(4S)-iodo-tetrahydro-furan-(2S)-phosphonate.

(5R)-(2-amino-6-hydroxy-purin-9-ylmethyl)-(4S)-iodo-tetrahydro-furan-(2R)-phosphonate.

(5R)-(2-amino-6-hydroxy-purin-9-ylmethyl)-(4R)-chloro-tetrahydro-furan-(2S)-phosphonate.

(5R)-(2-amino-6-hydroxy-purin-9-ylmethyl)-(4R)-chloro-tetrahydro-furan-(2R)-phosphonate.

(5R)-(2-amino-6-hydroxy-purin-9-ylmethyl)-(4S)-chloro-tetrahydro-furan-(2S)-phosphonate.

(5R)-(2-amino-6-hydroxy-purin-9-ylmethyl)-(4S)-chloro-tetrahydro-furan-(2R)-phosphonate.

(5R)-(2-amino-6-hydroxy-purin-9-ylmethyl)-(4R)-bromo-tetrahydro-furan-(2S)-phosphonate.

(5R)-(2-amino-6-hydroxy-purin-9-ylmethyl)-(4R)-bromo-tetrahydro-furan-(2R)-phosphonate.

(5R)-(2-amino-6-hydroxy-purin-9-ylmethyl)-(4S)-bromo-tetrahydro-furan-(2S)-phosphonate.

(5R)-(2-amino-6-hydroxy-purin-9-ylmethyl)-(4S)-bromo-tetrahydro-furan-(2R)-phosphonate.

[(5R)-2(2-amino-6-hydroxy-purin-9-ylmethyl)4-methylene-tetrahydro-furan(2R)-yl]-phosphonic acid.

[(5S)-2(2-amino-6-hydroxy-purin-9-ylmethyl)-4-methylene-tetrahydro-furan(2S)-20 yl]-phosphonic acid.

[(5R)-2(2-amino-6-hydroxy-purin-9-ylmethyl)4-methylene-tetrahydro-furan(2S)-yl]-phosphonic acid.

[(5S)-2(2-amino-6-hydroxy-purin-9-ylmethyl)4-methylene-tetrahydro-furan(2R)-yl]-phosphonic acid.

[(5R)-2(2-amino-6-hydroxy-purin-9-ylmethyl)-2,5-dihydro-furan-(2R)-yl]-phosphonic acid;

[(5S)-2(2-amino-6-hydroxy-purin-9-ylmethyl)-2,5-dihydro-furan-(2S)-yl]-phosphonic acid;

[(5R)-2(2-amino-6-hydroxy-purin-9-ylmethyl)-2,5-dihydro-furan-(2S)-yl]-phosphonic acid;

[(5S)-2(2-amino-6-hydroxy-purin-9-ylmethyl)-2,5-dihydro-furan-(2R)-yl]-phosphonic acid;

(5R)-(2-amino-6-cyclopropylamino-purin-9-ylmethyl)-tetrahydro-furan-(2S)-phosphonate.

(5R)-(2-amino-6-cyclopropylamino-purin-9-ylmethyl)-tetrahydro-furan-(2R)-phosphonate.

(5S)-(2-amino-6-cyclopropylamino-purin-9-ylmethyl)-tetrahydro-furan-(2S)-phosphonate.
(5S)-(2-amino-6-cyclopropylamino-purin-9-ylmethyl)-tetrahydro-furan-(2R)-phosphonate.
(5R)-(2-amino-6-cyclopropylamino-purin-9-ylmethyl)-(4S)-azido-tetrahydro-furan-(2S)-phosphonate;
(5R)-(2-amino-6-cyclopropylamino-purin-9-ylmethyl)-(4R)-azido-tetrahydro-furan-(2S)-phosphonate;
(5R)-(2-amino-6-cyclopropylamino-purin-9-ylmethyl)-(4S)-azido-tetrahydro-furan-(2R)-phosphonate;
(5R)-(2-amino-6-cyclopropylamino-purin-9-ylmethyl)-(4R)-azido-tetrahydro-furan-(2R)-phosphonate;
(5R)-(2-amino-6-cyclopropylamino-purin-9-ylmethyl)-(4R)-fluoro-tetrahydro-furan-(2S)-phosphonate;
(5R)-(2-amino-6-cyclopropylamino-purin-9-ylmethyl)-(4R)-fluoro-tetrahydro-furan-(2R)-phosphonate;
(5R)-(2-amino-6-cyclopropylamino-purin-9-ylmethyl)-(4S)-fluoro-tetrahydro-furan-(2S)-phosphonate;
(5R)-(2-amino-6-cyclopropylamino-purin-9-ylmethyl)-(4S)-fluoro-tetrahydro-furan-(2R)-phosphonate;
(5R)-(2-amino-6-cyclopropylamino-purin-9-ylmethyl)-(4S)-hydroxy-tetrahydro-furan-(2S)-phosphonate;
(5R)-(2-amino-6-cyclopropylamino-purin-9-ylmethyl)-(4R)-hydroxy-tetrahydro-furan-(2R)-phosphonate;
(5R)-(2-amino-6-cyclopropylamino-purin-9-ylmethyl)-(4S)-hydroxy-tetrahydro-furan-(2R)-phosphonate;
(5R)-(2-amino-6-cyclopropylamino-purin-9-ylmethyl)-(4R)-hydroxy-tetrahydro-furan-(2S)-phosphonate;
(5R)-(2-amino-6-cyclopropylamino-purin-9-ylmethyl)-(4R)-iodo-tetrahydro-furan-(2S)-phosphonate;
(5R)-(2-amino-6-cyclopropylamino-purin-9-ylmethyl)-(4R)-iodo-tetrahydro-furan-(2R)-phosphonate;
(5R)-(2-amino-6-cyclopropylamino-purin-9-ylmethyl)-(4S)-iodo-tetrahydro-furan-(2S)-phosphonate;
(5R)-(2-amino-6-cyclopropylamino-purin-9-ylmethyl)-(4S)-iodo-tetrahydro-furan-(2R)-phosphonate;
(5R)-(2-amino-6-cyclopropylamino-purin-9-yl methyl)-(4R)-chloro-tetrahydro-furan-(2S)-phosphonate;
(5R)-(2-amino-6-cyclopropylamino-purin-9-ylmethyl)-(4R)-chloro-tetrahydro-furan-(2R)-phosphonate;
(5R)-(2-amino-6-cyclopropylamino-purin-9-yl methyl)-(4S)-chloro-tetrahydro-furan-(2S)-phosphonate;
(5R)-(2-amino-6-cyclopropylamino-purin-9-ylmethyl)-(4S)-chloro-tetrahydro-furan-(2R)-phosphonate;
(5R)-(2-amino-6-cyclopropylamino-purin-9-ylmethyl)-(4R)-bromo-tetrahydro-furan-(2S)-phosphonate;
(5R)-(2-amino-6-cyclopropylamino-purin-9-ylmethyl)-(4R)-bromo-tetrahydro-furan-(2R)-phosphonate;
(5R)-(2-amino-6-cyclopropylamino-purin-9-ylmethyl)-(4S)-bromo-tetrahydro-furan-(2S)-phosphonate;
(5R)-(2-amino-6-cyclopropylamino-purin-9-ylmethyl)-(4S)-bromo-tetrahydro-furan-(2R)-phosphonate;
[(5R)-2(2-amino-6-cyclopropylamino-purin-9-ylmethyl)-(4-methylene-tetrahydro-furan(2R)-yl]-phosphonic acid;
[(5S)-2(2-amino-6-cyclopropylamino-purin-9-ylmethyl)-4-methylene-tetrahydro-furan(2S)-yl]-phosphonic acid;
[(5R)-2(2-amino-6-cyclopropylamino-purin-9-ylmethyl) 4-methylene-tetrahydro-furan(2S)-yl]-phosphonic acid;
[(5S)-2(2-amino-6-cyclopropylamino-purin-9-ylmethyl)-4-methylene-tetrahydro-furan(2R)-yl]-phosphonic acid;
[(5R)-2(2-amino-6-cyclopropylamino-purin-9-ylmethyl)-2,5-dihydro-furan-(2R)-yl]-phosphonic acid;
[(5S)-2(2-amino-6-cyclopropylamino-purin-9-ylmethyl)-2,5-dihydro-furan-(2S)-yl]-phosphonic acid;
[(5R)-2(2-amino-6-cyclopropylamino-purin-9-ylmethyl)-2,5-dihydro-furan-(2S)-yl]-phosphonic acid;
[(5S)-2(2-amino-6-cyclopropylamino-purin-9-ylmethyl)-2,5-dihydro-furan-(2R)-yl]-phosphonic acid;

The compounds of formula (I) and of formulas i to xii, either as an isonomic mixture or as the individual enantiomer; and useful for the treatment of humans or mammalians to inhibit at least one of the following viruses: HCMV (Human Cytomegalovirus), HSV-1 or HSV-2 (Herpes Simplex 1 or 2), HIV (Human Immunodeficiency Virus), HTLV (Human T-lymphotropic virus), or HBV (Hepatitis B Virus). In a specific embodiment of the present invention compounds of formula (I) are active against HIV (Human Immunodeficiency Virus) and HBV (Hepatitis B Virus).

In a further aspect of the present invention, there is provided a method for the treatment of a viral infection in an infected host comprising the step of administering an antivirally effective dose of a compound of formula (I) as defined herein above or a pharmaceutically acceptable derivative thereof. In an alternative embodiment of the present invention the host is a mammal.

As will be appreciated by those skilled in the art, the compounds in accordance with the invention can be used for prophylaxis as well as the treatment of established infections of symptoms.

The compounds of the present invention may also be useful in the treatment of AIDS-related conditions such as AIDS-related complex (ARC), persistent generalized lymphadenopathy (PGL), AIDS-related neurological conditions (such as dementia), anti-HIV antibody-positive and HIV-positive conditions, Kaposi's sarcoma, thrombocytopenia purpura and opportunistic infections.

The compounds of the invention are also useful in the prevention or progression to clinical illness of individuals who are anti-HIV antibody or HIV-antigen positive and in prophylaxis following exposure to HIV.

The compounds of formula (I) or the pharmaceutically acceptable salts and esters thereof, may also be used for the prevention of viral contamination of biological fluids such as blood or semen in vitro.

The present invention also includes a commercial package containing one or more compounds of formula (I) or the pharmaceutically acceptable salts or esters thereof as an active agent with instructions of use as treatment against antiviral infections in mammals.

It will also be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferable about 3 to about 30 $\mu$M. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula (I) according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial, antifungal, and antiviral agents, immunomodulators or preservatives.

The compounds of the invention may also be used in combination with other therapeutic or prophylactic agents for example other antiinfective agents. In particular the compounds of the invention may be employed together with known antiviral, antimicrobial, or antifungal agents or immunomodulators. The invention thus provides, in a further aspect, a combination comprising a compound of formula (I) or) or a pharmaceutically acceptable derivative thereof together with another therapeutically active agent, in particular, an antiviral agent.

The therapeutically active agent to be used in combination with the compounds of the present invention may be selected from the group epivir, DAPD, FTC, AZT, d4T, nevirapine, DMP-226, nelfinavir, indinavir, delavirdine, MKC-442, 1592U89 (abacavir), 141W94, MK-639, saquinavir, ritonavir ,TIBO, HEPT, BHAP, α-APA, TSAO, calanolides, L-697,661, 2',3'-dideoxycytidine (ddC), 2',3'-dideoxyadenosine, 2',3'-dideoxyinosine (ddI), 3'-deoxythymidine, 2',3'-dideoxy-2',3'-didehydrothymidine, and 2',3'-dideoxy-2',3'-didehydrocytidine and ribavirin; acyclic nucleosides such as acyclovir, ganciclovir, interferons such as alpha-, beta-and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease such as L-735,524.

In accordance with a further aspect of the present invention, the further therapeutic agent or agents may be chosen from epivir, DAPD, FTC, AZT, nevirapine, DMP-226, nelfinavir, indinavir, delavirdine, MKC-442, abacavir, 141W94, MK-639, saquinavir, ritonavir, acyclovir, interferon alfa, L-735,524, d4T, ddC, and ddI.

The individual components of such combinations may be administered either sequentially or simultaneously in separate or combined pharmaceutical formulations.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

In another aspect method of treating a host infected with an HIV strain which includes administering an effective dose of a compound or the combinations of compounds of formula (I) capable of inhibiting viral replication.

When the compound of formula (I) or a pharmaceutically acceptable derivative thereof is used in combination with a second therapeutic agent active against the same virus, the dose of each compound may be either the same or differ from that when the compound is used alone. Appropriate doses will be readily appreciated by those skilled in the art.

The advantageous effects of the compounds of formula (I) and the second antiviral agents are observed over a wide ratio for example 1:250 to 250:1, alternatively 1:50 to 50: 1, particularly about 1 :10 to 10:1. Conveniently each compound will be employed in the combination in an amount at which it exhibits antiviral activity when used alone.

In an embodiment of the present invention the infected host is a mammal. Alternately, the infected host is human.

It is expected that the present combinations will be generally useful against viral infections or virus-associated tumours in humans, and the method of their use to inhibit viral infectivity or tumour growth in vitro or in vivo is also within the scope of the present invention.

Thus, there is provided, as a further aspect of the invention, a method for the treatment of a viral infection in a mammal, including man, comprising co-administration of an antiviral compound of formula (I) and a further antiviral report which inhibits HIV or HBV replication. Therapeutic methods comprising administration of a combination of a compound of formula (I) and more than one of the second antiviral agents, either together or in a plurality of paired combinations, is also within the scope of the invention.

It will be appreciated that the compound of formula (I) and the second antiviral agent may be administered either simultaneously, sequentially or in combination. If administration is sequential, the delay in administering the second of the active ingredients should not be such as to lose the benefit of the synergistic effect of the combination. Preferably administration will be simultaneous.

It will be appreciated by those skilled in the art that reference herein to treatment extends to prophylaxis as well as the treatment of established infections or symptoms.

It will be further appreciated that the amount of a combination of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 1 to about 750 mg/kg e.g. from about 10 to about 75-mg/kg of bodyweight per day, such as 3 to about 120 mg per kilogram body weight of the recipient per day, preferably in the range of 6 to 90 mg/kg/day, most preferably in the range of 15 to 60 mg/kg/day of each of the active ingredients of the combination.

The desired dose may conveniently be presented in a single dose or as divided doses administered at appropriate intervals, for example as two, three, four or more sub-doses per day.

The compounds of formula (I) may be prepared by the process outlined in Scheme 1, wherein X is an oxygen, Q and U are each independently $CH_2$, CHOH, CH-halogen, CH—$N_3$, or both Q and U are CH linked by a double bond. Derivatives of compounds of formula (I) may be prepared by following procedures outlined in the literature, e.g.:S-acyl-2-thioethyl (SATE) in J. Med. Chem. (1995) 38:3941–3950; carboxyloxymethyl such as pivaloyloxymethyl (POM) in Antiviral Chem. Chemother (1994) 5:91–98 or alkyl methyl carbonates, such as isopropyl methyl carbonate (POC) in Antiviral Chem. Chemother. (1997) 8: 557–564; phenyl or benzylphosphotriesters analogues in Bioorg. Med. Chem. Lett. (1997) 7: 99–104 or phosphotriesters analogues in WO98/17281.

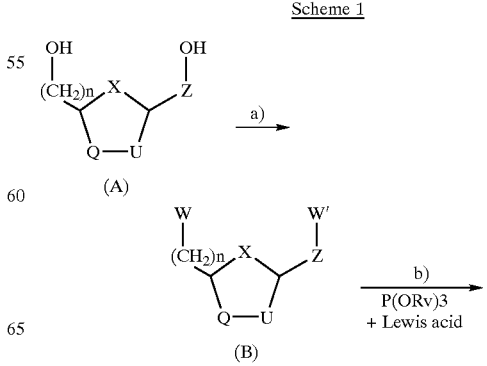

Scheme 1

-continued

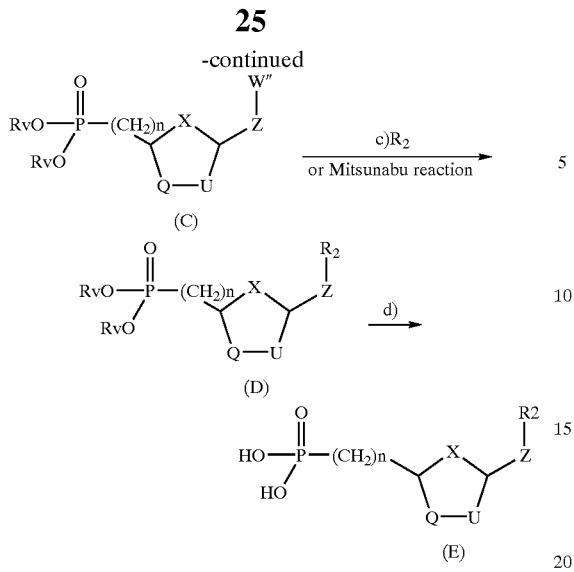

X, U and Q are as defined herein above.

W is a displaceable group (such as acetoxy, halogen, methoxy, methoxyethyloxy, tosyloxy, mesyloxy.)

W' is a hydroxy protecting group (such as silyloxy, acyloxy, aracyloxy, trityloxy).

W" is a displaceable group (such as hydroxy, mesyloxy, tosyloxy, halogen.).

Z is $(CH_2)m$, where m is 0 or an integer from 1–3 (preferably m=1)

n is 0 to 1 (preferably n=0)

$R_v$ is a hydroxy protecting group such as a $C_{1-6}$ alkyl or an $C_{6-10}$ aryl (preferably methyl, ethyl, isopropyl, phenyl or benzyl)

$R_2$ is as defined above, profoundly a purine or pyrimidine (preferably attaching at N-9 position for purine and N-1 or N-3 for pyrimidine).

The steps illustrated in scheme can be briefly described as follows:

a) Both hydroxy groups of compound (A) are sequentially converted to form compound (B) where W and W' are similar or different protecting groups as defined above;

b) The W functionality of compound (B) is then converted to a 2-dialkylphosphonate derivative (C) under Arbuzov conditions by treatment with trialkyl phosphite with or without of a Lewis acid such as $TiCl_4$ as a catalyst. At this stage, compound (C) may be optionally separated to its cis and trans isomers before further steps are carried out. W' is then converted to W" by deprotection to the hydroxy function. At this stage, the corresponding hydroxy derivative may be optionally used for the Mitsunobu coupling reaction with a purine or pyrimidine base or may be converted to a displaceable group as defined above.

c) W" is displaced by a purine or pyrimidine base to give compound (D).

d) Once made, ester (D) is converted to the corresponding phosphonate derivative (E).

EXAMPLE 1

Synthesis of (5R)-(2-Amino-6-hydroxy-purin-9-ylmethyl)-(4R)-azido-tetrahydro-furan-(2S)-phosphonate The synthesis is carried out following Scheme A1

SCHEME 1A

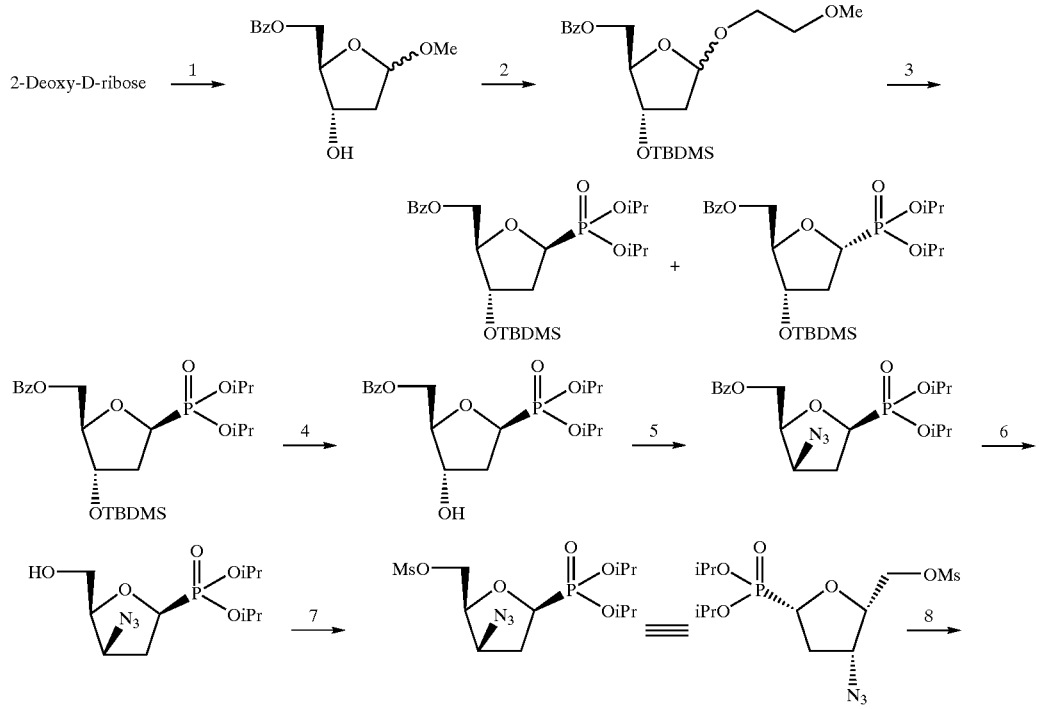

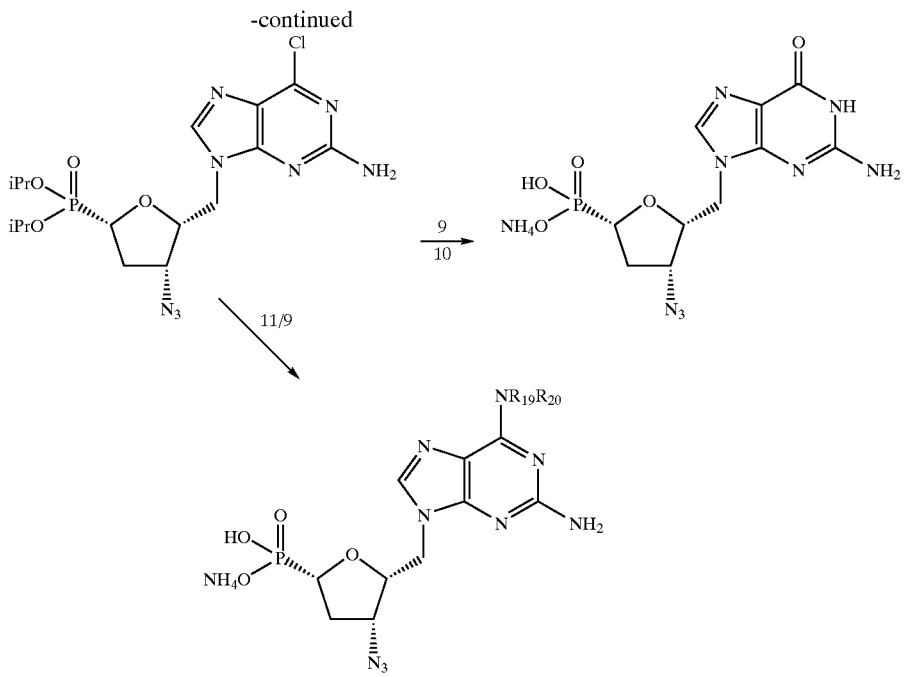

1) a)MeOH, H⁺; b) BzCl, pyridine, 0° C.; 2) a) 2-methoxyethanol, p-TSA, 90° C.; b) TBDMSCl, imidazole; 3) TiCl₄, triisopropylphosphite, −10° C.; 4) MEOH, aqu..HCl; 5) diphenylphosphoryl azide, PPh₃, DEAD, THF; 6) MEOH, K₂CO₃; 7) MsCl, Et₃N, CH₂Cl₂; 8) 2-amino-6-chloro-purine, Cs₂CO₃, DMF, 100° C.; 9) a) TMSBr, CH₂Cl₂; b) aqu. HCl, reflux, c) NH₄OH; 10) EtOH washing, 11) EtOH, NR₁₉R₂₀, 80° C.

1.1) Preparation of Benzoic Acid (3S)-Hydroxy-5-methoxy-tetrahydro-furan-(2R)-ylmethyl Ester.

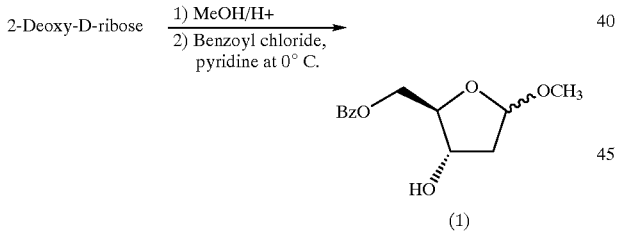

A solution of 2-deoxy-D-ribose (7.5 g, 55.9 mmol) in dry methanol (75 ml) was treated with methanolic hydrochloric acid prepared from acetyl chloride (0.4 ml) in methanol (4 ml). The mixture was stirred at room temperature for 0.5 hr. Pyridine (4 ml) was added and the mixture was evaporated to dryness. It was co-evaporated with toluene (2×50 ml) and pumped for 1 hr. The crude product was dissolved in CH₂Cl₂ (60 ml). Pyridine (7.5 ml) and DMAP (catalytic) were added. The mixture was cooled to 0° C. and benzoyl chloride (6.8 ml, 58.6 mmol) was added dropwise. After 1 hr and 20 min. water (10 ml) was added. The mixture was extracted with CH₂Cl₂. The extracts were washed with 1N HCl, 2.5% NaHCO₃ solution and saturated NaCl solution, dried and evaporated. Pure product was obtained by passing through a column of silica gel (eluent: hexane-EtOAc=7:3) (10 g, 70.9%).

NMR (δ, CDCl₃): 8.09, 8.03 (1H each, d, J=7.1 Hz), 7.58 (1H, t, J=6.7 Hz), 7.45 (2H, t, J=7.6 Hz), 5.11–5.16 (1H), 4.34–4.60, 4.10–4.27 (3H, 5 multiplets), 3.42, 3.33 (3H, two singlets), 2.26–2.35, 2.12–2.23 (2H, two multiplets).

1.2) Preparation of Benzoic Acid (3S)-(tert-Butyl-dimethyl-silanyloxy)-5-(2-methoxy-ethoxy)-tetrahydro-furan-(2R)-ylmethyl Ester

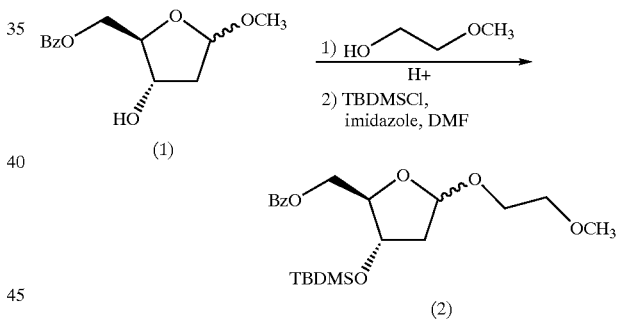

Benzoic acid (3S)-hydroxy-5-methoxy-tetrahydro-furan-(2R)-ylmethyl ester (10 g, 39.7 mmol) (1) was dissolved in methoxyethanol (60 ml). P-Toluenesulfonic acid (190 mg) was added and the mixture was held at 90° C. for 5.5 hrs. It was cooled. Saturated NaHCO₃ (5 ml) was added. Methoxyethanol was removed using toluene as co-solvent. The crude was extracted with ethyl acetate (150 ml), washed with water, saturated NaCl solution, dried and evaporated yielding 10 g of crude product. This was taken up in DMF (21 ml). TBDMSCl (6.9 g, 45.8 mmol) and imidazole (3.9 g, 57.3 mmol) were added. The reaction was complete at room temperature in an hour. Saturated NaHCO₃ (100 ml) was added and the mixture was stirred for 10 min, extracted with ether (3×200 ml), washed with saturated NaCl solution (100 ml), dried and evaporated. Pure product was obtained by passing through a column of silica gel (hexane-EtOAc=9 1) (yield 9.1 g, 56%).

HNMR (δ, CDCl₃): 8.05–8.10 (2H, pair of doublets), 7.58 (1H, t, J=7.3 Hz), 7.46 (2H, t, J=7.6 Hz), 5.17–5.24 (1H), 4.48 4.58, 4.31 4.37, 4.11–4.22, 3.88–3.94, 3.73–3.82, 3.51–3.65, 3.44–3.47 (8H, 7 multiplets), 3.33, 3.40 (3H, two singlets), 2.46–2.53, 2.31–2.36, 2.05–2.11, 1.94–2.00 (2H, four multiplets), 0.88 (9H, singlet), 0.07 (3H, s), 0.06, 0.05 (3H, two singlets).

1.3) Preparation of Benzoic Acid (3S)-(tert-Butyl-dimethyl-silanyloxy)-(5S)-(diisopropoxy-phosphoryl)-tetrahydro-furan-(2R)-ylmethyl Ester

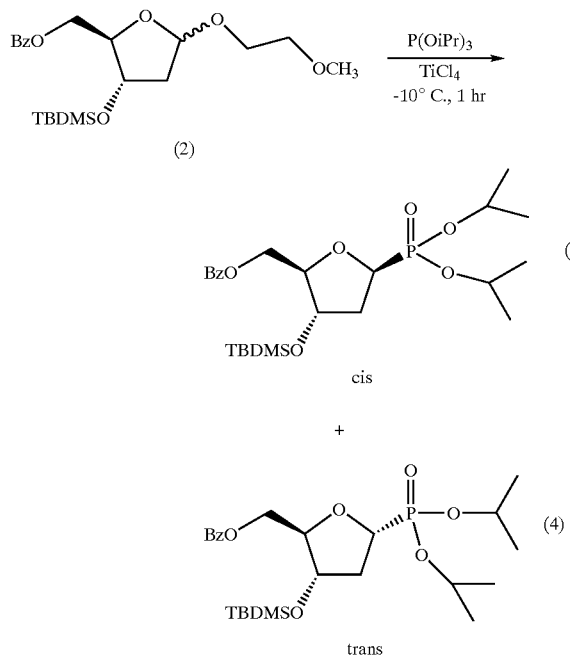

To a solution of benzoic acid (3S)-(tert-butyl-dimethyl-silanyloxy)-5-(2-methoxy-ethoxy)-tetrahydro-furan-(2R)-ylmethyl ester (9.1 g, 22.2 mmol) in $CH_2Cl_2$(200 ml) cooled to –10° C. C was added triisopropylphosphite (6.4 ml, 26 mmol) followed by dropwise addition of $TiCl_4$ (2.6 ml, 23.7 mmol) during 5 minutes. The mixture was stirred at –10° C. for 1 hr. and poured quickly in 100 ml saturated sodium bicarbonate. It was stirred for 0.5 hr and filtered through a bed of celite. Bed was washed with dichloromethane. Organic layer was separated. Aqueous part was extracted with dichloromethane (2×150 ml). The extracts were combined with the organic layer, dried and evaporated. The crude product was purified by column chromatography over silica gel (hexane-EtOAc mixtures as eluents) yielding 4.3 g of the cis product contaminated with bit of phosphite.

HNMR (δ, $CDCl_3$): 8.04 (2H, d, J=1.5, 7.2 Hz); 7.58 (1H, t, J=7.5 Hz), 7.45 (2H, t, J=7.5 Hz), 4.75–4.86 (2H, m), 4.54 (1H, dd, J=2.7, 12.0 Hz), 4.28–4.37 (2H, m), 4.23 (1H, dd, J=7.4, 10.5 Hz), 4.09–4.14 (1H, m), 2.46–2.54 (1H, m), 2.17–2.30 (1H, m), 1.36 and 1.35 (12H, d, J=5.9 Hz), 0.89 (9H, s), 0.08, 0.06 (3H each); $C^{13}$ NMR (ppm, $CDCl_3$): 166.2, 133.0, 129.9, 129.5, 128.3, 82.4 (d, J=4.7 Hz), 72.3 (d, J=175,3 Hz), 72.3 (d, J=8.7 Hz), 71.4 , 71.1 (d, J=7.0 Hz), 63.6, 36.1, 25.6, 24.14, 24.03, 24.0, 23.91, 23.89,23.83, 17.8 (extra signals due to coupling with phosphorus). $P^{31}$ NMR (ppm, $CDCl_3$): 21.06 (s).

1.4) Preparation of Benzoic Acid (5S)-(Diisopropoxy-phosphoryl)-(3S)-hydroxy-tetrahydro-furan-(2R)-ylmethyl Ester

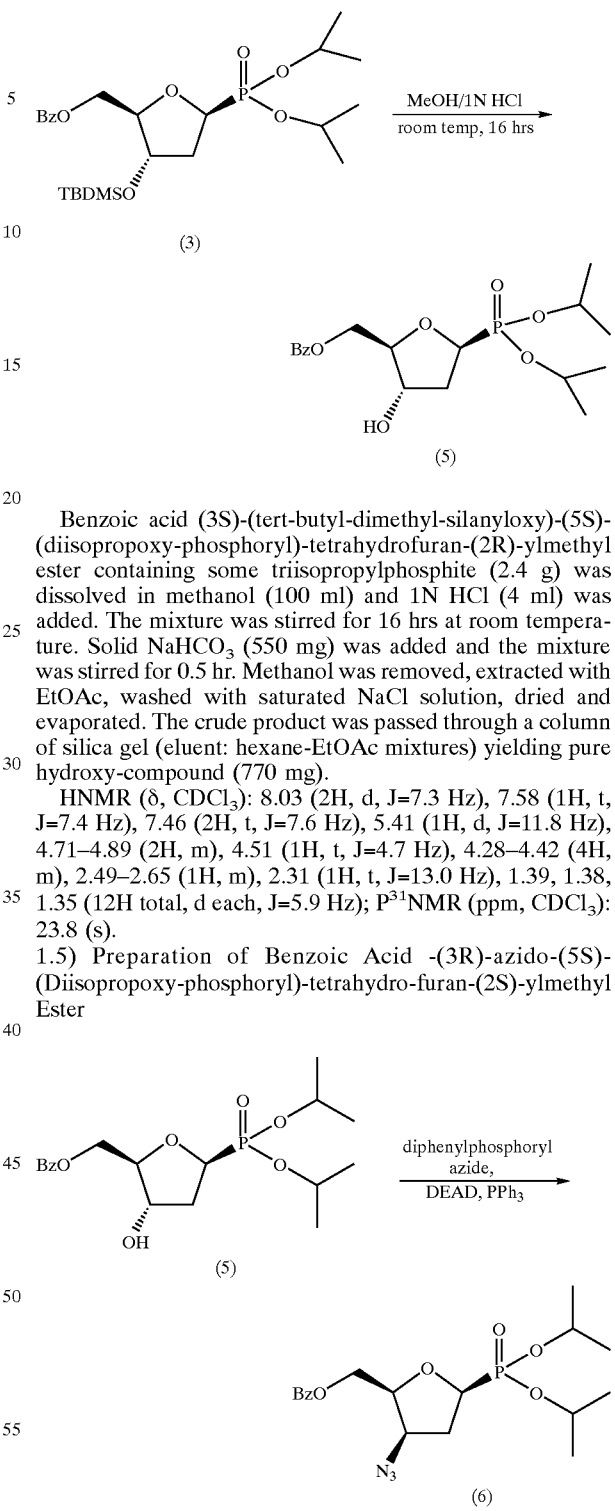

Benzoic acid (3S)-(tert-butyl-dimethyl-silanyloxy)-(5S)-(diisopropoxy-phosphoryl)-tetrahydrofuran-(2R)-ylmethyl ester containing some triisopropylphosphite (2.4 g) was dissolved in methanol (100 ml) and 1N HCl (4 ml) was added. The mixture was stirred for 16 hrs at room temperature. Solid $NaHCO_3$ (550 mg) was added and the mixture was stirred for 0.5 hr. Methanol was removed, extracted with EtOAc, washed with saturated NaCl solution, dried and evaporated. The crude product was passed through a column of silica gel (eluent: hexane-EtOAc mixtures) yielding pure hydroxy-compound (770 mg).

HNMR (δ, $CDCl_3$): 8.03 (2H, d, J=7.3 Hz), 7.58 (1H, t, J=7.4 Hz), 7.46 (2H, t, J=7.6 Hz), 5.41 (1H, d, J=11.8 Hz), 4.71–4.89 (2H, m), 4.51 (1H, t, J=4.7 Hz), 4.28–4.42 (4H, m), 2.49–2.65 (1H, m), 2.31 (1H, t, J=13.0 Hz), 1.39, 1.38, 1.35 (12H total, d each, J=5.9 Hz); $P^{31}$NMR (ppm, $CDCl_3$): 23.8 (s).

1.5) Preparation of Benzoic Acid -(3R)-azido-(5S)-(Diisopropoxy-phosphoryl)-tetrahydro-furan-(2S)-ylmethyl Ester To a mixture of benzoic acid (5S)-(diisopropoxy-phosphoryl)-(3S)-hydroxy-tetrahydro-furan-(2R)-ylmethyl ester (550 mg; 1.42 mmol),triphenylphosphine (436 mg; 1.66 mmol) and diethylazodicarboxylate (DEAD) (267 μl; 1.69 mmol) in THF (4.5 ml) was added diphenylphosphoryl azide (325 μl; 1.51 mmol) in THF (4.5 ml) during 5 min. The mixture was stirred for 22 hrs. at room temperature, evaporated down to dryness carefully without applying heat and pumped for a while. It was passed through a column of silica gel (3 and 5% acetone in CH₂Cl₂ as eluents) giving 550 mg of product containing some impurities due to the by-products from DEAD.

NMR (δ; CDCl₃): 8.03 (2H, d, J=7.2 Hz); 7.58 (1H, t, J=7.4 Hz); 7.45 (2H, t, J=7.7 Hz); 4.73–4.84 (2H, m); 4.34–4.58 (5H, 3 multiplets); 2.54–2.66 (1H, m); 2.41–2.49 (1H, m); 1.34, 1.33 (6H each, J=6.1 Hz).

1.6) Preparation of (4R)-Azido-(5S)-(hydroxymethyl-tetrahydro-furan-(2S)-yl)-phosphonic Acid Diisopropyl Ester

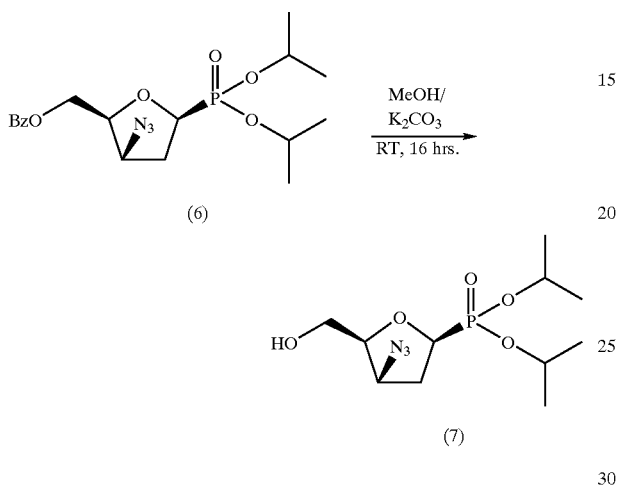

Benzoic acid (3R)-azido-(5S)-(diisopropoxy-phosphoryl)-tetrahydro-furan-(2S)-yl methyl ester (550 mg, containing some impurities) was dissolved in MeOH (12 ml) and K₂CO₃ (12 mg) was added. It was stirred for 16 hrs. at room temperature. The mixture was neutralized with acidic resin, filtered, evaporated and passed through a column of silica gel (CH₂Cl₂ and 2% methanol in CH₂Cl₂ as eluents) giving 320 mg of pure product (73% in two steps.)

NMR (δ; CDCl₃): 4.72–4.85 (2H, m); 4.30–4.34 (2H, m); 4.21 (1H, dd, J=5.6, 10.2 Hz); 3.76–3.88 (2H, m); 2.49–2.61 (1H, m); 2.36–2.44 (1H, m); 1.97 (1H, t, J=5.6 Hz); 1.33–1.36 (12H, m).

IR (thin film): 3385.9 cm⁻¹.

1.7) Preparation of Methanesulfonic Acid -(3R)-azido-(5S)-(Diisopropoxy-phosphoryl)-tetrahydro-furan-(2S)-ylmethyl Ester

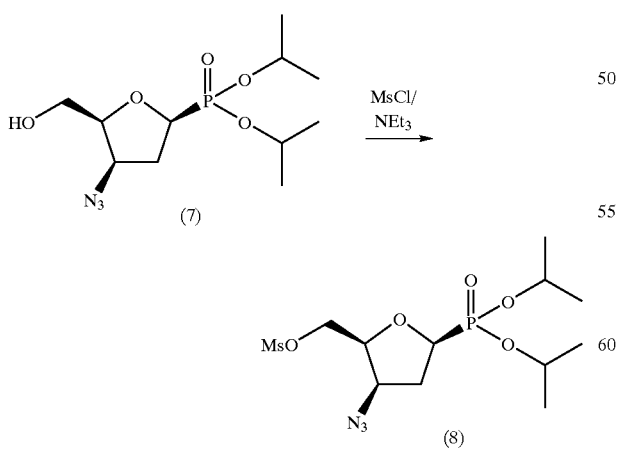

(4R)-Azido-(5S)-(hydroxymethyl-tetrahydro-furan-(2S)-yl)-phosphonic acid diisopropyl ester (300 mg, 0.98 mmol) was dissolved in CH₂Cl₂ (6 ml) and cooled to 0° C. Trielthylamine (210 μl, 1.51 mmol) and methane sulfonyl chloride (85 μl, 1.1 mmol) were added. The mixture was stirred at 0° C. for 0.5 hr. Saturated NaHCO₃ solution was added and stirred for 10 min. It was extracted with CH₂Cl₂ (200 ml), washed with 0.1 N HCl followed by washing with 2.5% NaHCO₃-sat. NaCl solution mixture, dried and evaporated. The crude product (350 mg) was pure enough for the next step.

NMR (δ; CDCl₃): 4.76–4.79 (2H, m); 4.34–4.40 (5H, m); 3.07 (3H, s); 2.40–2.59 (2H, 2m); 1.34 (12H, m).

1.8) Preparation of [(5R)-(2-Amino-6-chloro-purin-9-ylmethyl)-(4R)-azido-tetrahydro-furan-(2S)-yl]-phosphonic Acid Diisopropyl Ester

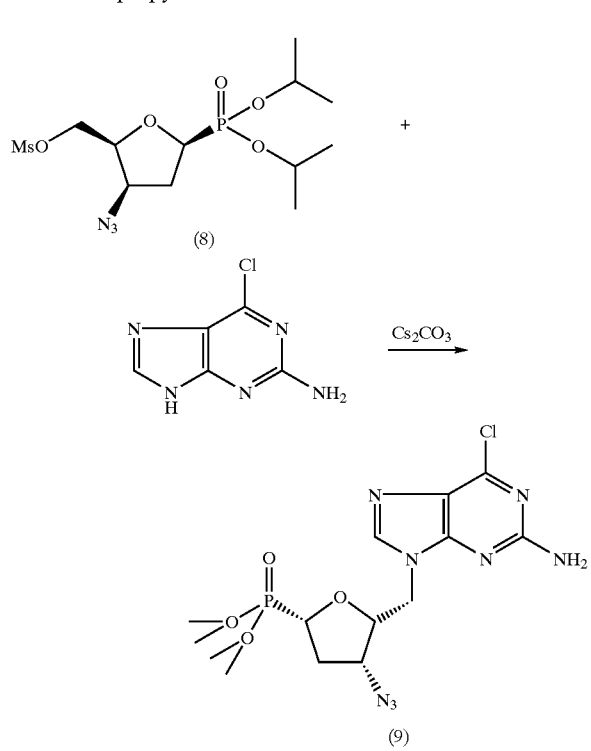

A mixture of cesium carbonate (208 mg, 0.64 mmol) and 2-amino-6-chloro-purine (112 mg, 0.66 mmol) in DMF (1 ml) was stirred at 100° C. for 0.5 hr. Methanesulfonic acid-(3R)-azido-(5S)-(diisopropoxy-phosphoryl)-tetrahydro-furan-(2S)-yl methyl ester (150 mg, 0.39 mmol) in DMF (3 ml) was added dropwise. The mixture was held at 100° C. for 10 hrs. It was cooled, filtered, evaporated and passed through columns of silica gel for purification (CH₂Cl₂, 2%-methanol and 4% methanol in CH₂Cl₂ as eluents) giving pure product (73 mg, 41%).

NMR (δ; CDCl₃): 7.86 (1H, s); 5.08 (2H, broad s); 4.61–4.75 (2H, m); 4.36–4.46 (3H, m); 4.28 (1H, ill-defined t, J=4.0 Hz); 4.21 (1H, dd, J=8.9, 15.2 Hz); 2.45–2.67 (2H, 2 multiplets); 1.32, 1.29, 1.28, 1.24 (3H each, doublets, J=6.2 Hz). Phosphorus NMR (ppm,CDCl₃): 20.35 (s). LCMS: 459.1 (M+1). C¹³ NMR (ppm, CDCl₃): 159.1, 153.7, 151.2, 142.7, 125.0, 79.8 (d, J=2.9 Hz), 72.5 (d, J=175.3 Hz), 72.0 (d, J=7.0 Hz), 71.2 (d, J=7.0 Hz), 62.2 (d, J=5.0Hz), 43.4, 33.6, 24.06, 24.03, 23.93, 23.80, 23.75 (some of these close).

1.9) Preparation of Ammonium;(5R)-(2-Amino-6-hydroxy-purin-9-ylmethyl)-(4R)-azido-tetrahydro-furan-(2S)-phosphonate

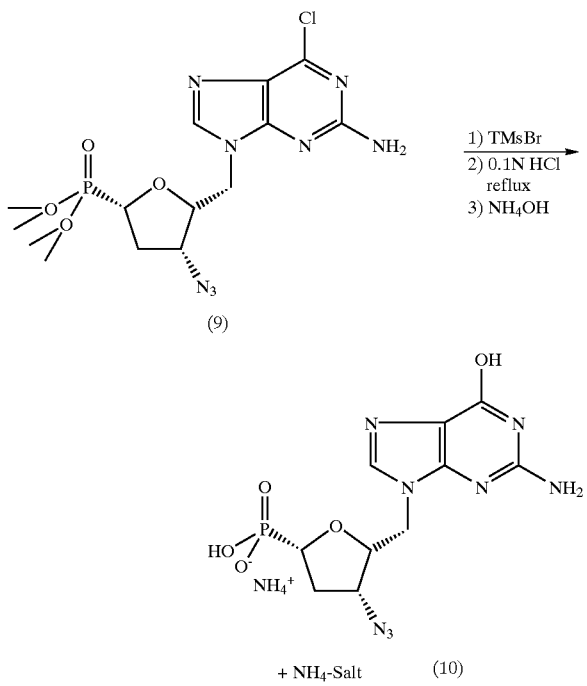

(9)

1) TMsBr
2) 0.1N HCl reflux
3) NH₄OH

(10) + NH₄-Salt

To a solution of [(5R)-(2-amino-6-chloro-purin-9-ylmethyl)-(4R)-azido-tetrahydro-furan-(2S)-yl]-phosphonic acid diisopropyl ester (38 mg, 0.083 mmol) in dichloromethane (2.5 ml) was added bromotrimethyl silane (118 μl, 0.89 mmol) and the mixture was stirred at room temperature for 16 hrs. The reaction mixture was evaporated down to dryness. Hydrochloric acid (0.1 N, 1.5 ml) was added and the mixture was refluxed for 16 hrs. At the end of this period, it was evaporated down to dryness and pumped for 2 hrs. It was 10 dissolved in water (10 ml) and adjusted to pH≈10 with ammonium hydroxide. The solution was extracted with dichloromethane (2×25 ml). The aqueous part was lyophilized giving 44 mg of solid product (slightly overweighed). It contained some NH₄-salt. It was purified by washing with EtOH (yield: 88%).

NMR (δ, $D_2O$): 7.78 (1H, s); 4.09–4.30 (5H, 2 multiplets); 2.28–2.37 (2H, m). Phosphorus NMR (ppm, $D_2O$): 16.56 (s); LC/MS: 357 (M-$NH_3$+1); HPLC: 98%.

EXAMPLE 2

Synthesis of (5R)-(2-Amino-6-hydroxy-purin-9-ylmethyl)-(4R)-fluoro-tetrahydro-furan-(2S)-phosphonate The synthesis is carried out following Scheme 1B:

SCHEME 1B

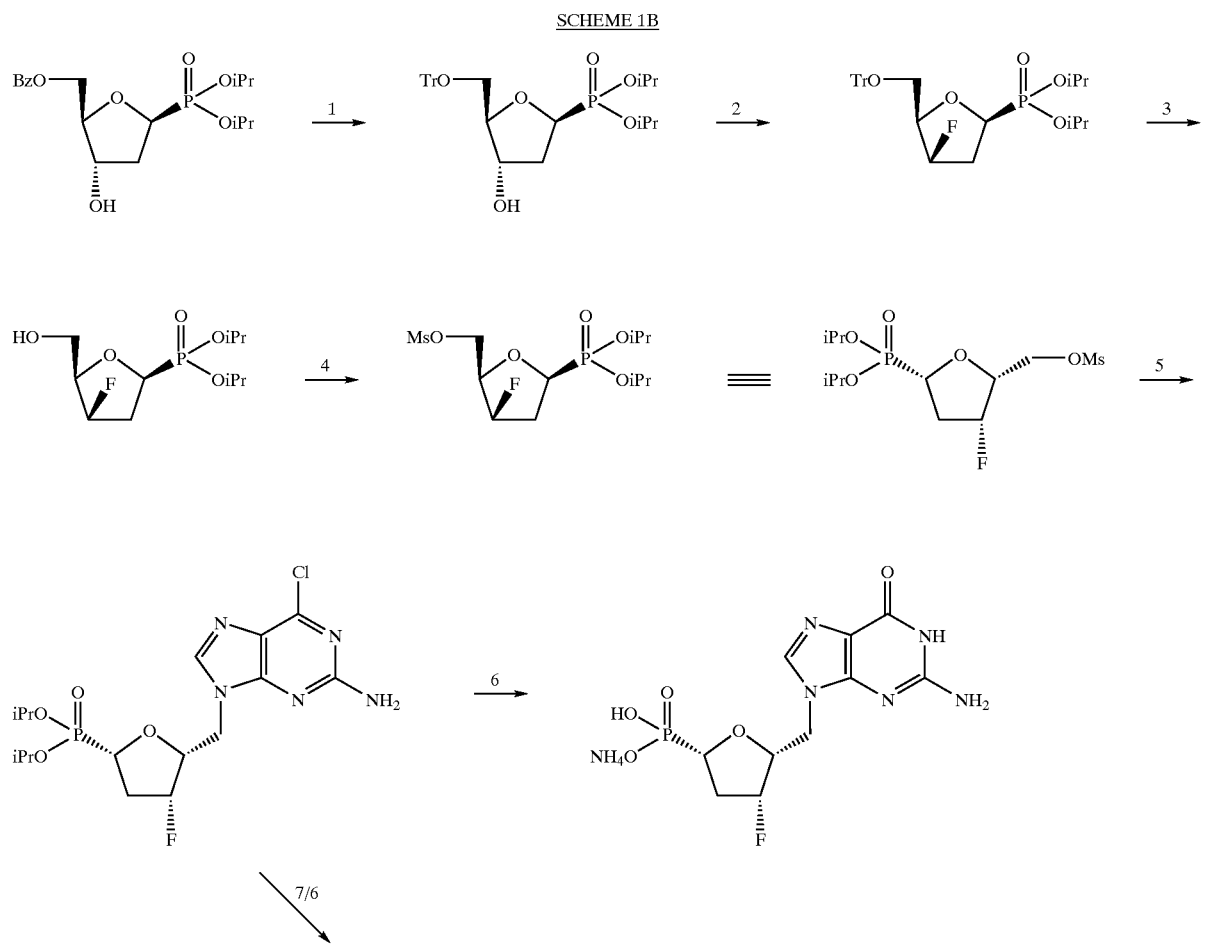

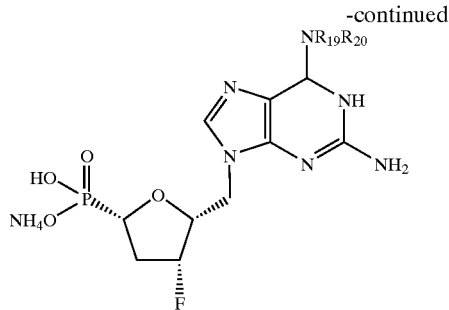

1) a) MEOH, K$_2$CO$_3$; b) Tr-Cl, pyridine ; 2) DAST, pyridine ; 3) aqu. 80% ACOH ; 4) Ms-Cl, Et$_3$N, CH$_2$Cl$_2$; 5) 2-amino-6-chloro-purine, CS$_2$CO$_3$, DMF, 100° C.; 6) a) TMSBr, CH$_2$Cl$_2$; b) aqu. HCl, reflux, c) NH$_4$OH, charcoal column, ethanol washing, 7). EtOH, NR$_{19}$R$_{20}$, 80° C.

2.1) Preparation of ((4S)-Hydroxy-(5R)-trityloxymethyl-tetrahydro-furan-(2S)-yl)-phosphonic Acid Diisopropyl Ester

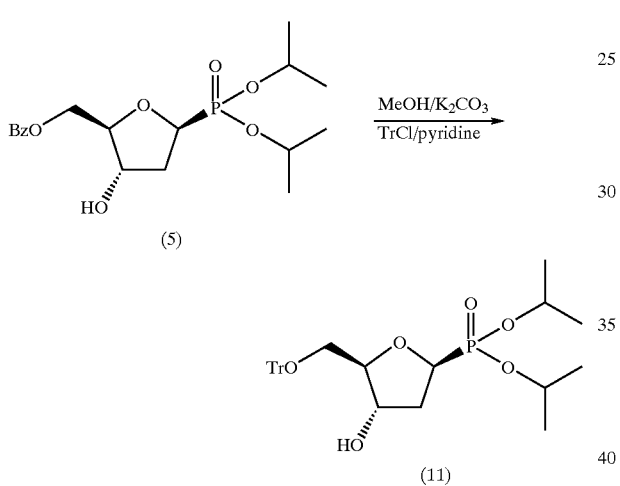

Benzoic acid (5S)-(diisopropoxy-phosphoryl)-(3S)-hydroxy-tetrahydro-furan-(2R)-yl methyl ester (120 mg, 0.31 mmol) (see Example 1.4) was treated with potassium carbonate (10 mg) in dry methanol (5 ml) for 16 hrs. The mixture was neutralized with acidic resin and filtered. The solvent was removed and pumped for 1 hr before going to the next step. The crude reaction mixture obtained above (80 mg) was dissolved in dichloromethane (2.5 ml) and cooled to 0° C. Pyridine (46 μl, 0.57 mmol) and DMAP (catalytic) were added followed by the addition of trityl chloride (92 mg, 0.33 mmol). The mixture was stirred at 0° C. for 1 hr and at room temperature for 25 minutes. Saturated NaHCO$_3$ solution was added, extracted with CH$_2$Cl$_2$, dried and evaporated. The crude was passed through a column of silica gel (hexane-EtOAc=70:30 and 60:40 as eluents) giving pure mono-trityl ether (65 mg, 40%).

HNMR (δ, CDCl$_3$): 7.12–7.45 (15H, aromatic protons), 5.18 (1H, d, J=11.7 Hz), 4.74–4.89 (2H, m), 4.42(1H, d, J=9.3 Hz), 4.25–4.33 (2H, m), 3.17 (1H, dd, J=4.7, 9.9 Hz), 3.11 (1H, dd, J=4.2, 9.9 Hz), 2.50–2.66 (1H, 2 multiplets), 2.24 (1H, t, J=13.2 Hz), 1.43, 1.40. 1.37, 1.36 (12H, 4 doublets, J=6.2 Hz); C$^{13}$ NMR (ppm, CDCl$_3$): 143.8, 128.6, 127.8, 127.0, 88.6, 86.6, 74.7 (d, J=168 Hz), 74.2, 72.7 (d, J=6.6 Hz), 71.2 (d, J=7.6 Hz), 64.6, 36.2, 24.30, 24.04, 24.00, 23.75, 23.70 (extra signals due to coupling with Phosphorus).

2.2) Preparation of ((4R)-Fluoro-(5R)-trityloxymethyl-tetrahydro-furan-(2S)-yl)-phosphonic Acid Diisopropyl Ester

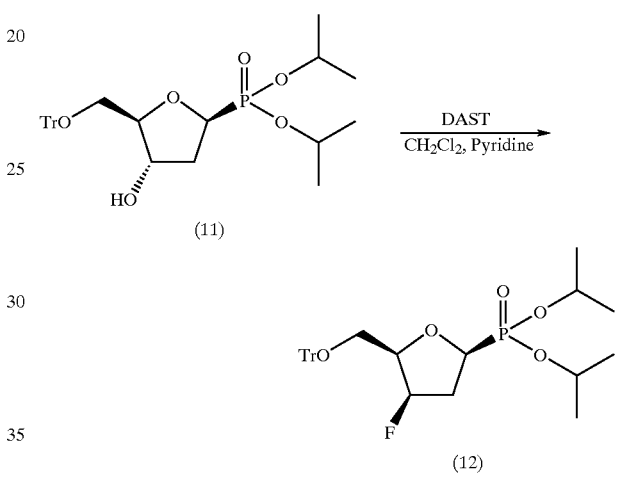

((4S)-Hydroxy-(5R)-trityloxymethyl-tetrahydro-furan-(2S)-yl)phosphonic acid diisopropyl ester (100 mg ; 0.19 mmol) was dissolved in CH$_2$Cl$_2$ (2 ml). DAST (diethylamino sulfur trifluoride) (50 μl; 0.38 mmol) was added slowly followed by the addition of pyridine (200 μl) after 10 minutes. The mixture was stirred at room temperature for 16 hrs. Saturated NaHCO$_3$ solution was added. After 5 minutes of stirring the mixture was extracted with CH$_2$Cl$_2$-saturated NaHCO$_3$-saturated NaCl mixture, dried and evaporated. The crude was purified via column chromatography giving pure fluoro derivative (31 mg, 31%).

HNMR (δ, CDCl$_3$): 7.22–7.47 (15H, aromatic protons), 5.29 (1H, d of an ill-defined triplet, J=52.7 Hz), 4.74–4.89 (2H, m), 4.23–4.36 (2H, m), 3.43 (1H, t, J=7.7 Hz), 3.29 (1H, dd, J=6.5. 9.2 Hz), 2.32–2.52 (2H, m), 1.37,1.35, 1.33 (12H, d each, J=5.8 Hz); C$^{13}$ NMR (ppm, CDCl$_3$): 143.74, 128.59, 127.65, 126.89, 92.84 (dd, J=6, 183.6 Hz), 86.63, 82.44 (dd, J=4.5, 18.1 Hz), 72.4 (d, J=169.6 Hz), 71.5, 70.84 (d, J=7 Hz), 60.86 (d, J=10.4 Hz), 34.78 (d, J=22 Hz), 24.15, 24.12, 23.98, 23.93, 23.88 (extra signals due to coupling with phosphorus). Fluorine NMR (ppm, CDCl$_3$): −197.8 (multiplet) unreferenced; P$^{31}$ NMR (ppm, CDCl$_3$): 21.56 (s).

2.3) Preparation of ((4R)-Fluoro-(5R)-hydroxymethyl-tetrahydro-furan-(2S)-yl)-phosphonic Acid Diisopropyl Ester

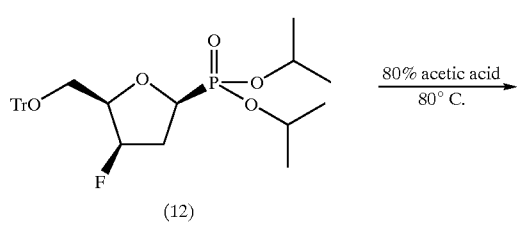

(12)

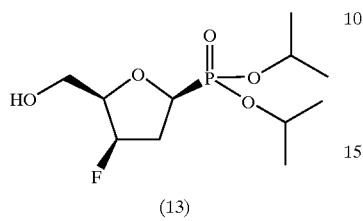

(13)

((4R)-Fluoro-(5R)-trityloxymethyl-tetrahydro-furan-(2S)-yl)-phosphonic acid diisopropyl ester (120 mg; 0.23 mmol) was treated with 80% acetic acid and held at 80° C. for 40 minutes. Acetic acid was removed using toluene as co-solvent and the crude reaction mixture was passed through a column of silica gel (10% methanol in dichloromethane as eluent) giving pure hydroxy product (50 mg 77%).

HNMR (δ, CDCl$_3$): 5.28 (1H, d of ill-defined triplet, J=54.0 Hz); 4.74–4.81 (2H, m); 4.37 (1H, dt, J=1.0, 7.9 Hz); 4.13–4.27 (1H, d of two complex signals, J=28.9 Hz); 3.84–3.89 (2H, m); 2.31–2.56 (3H, m), 1.32–1.36 (12H, m); P$^{31}$ NMR (ppm. CDCl$_3$):21.27 (singlet).

2.4) Preparation of Methanesulfonic Acid (5S)-(Diisopropoxy-phosphoryl)-(3R)-fluoro-tetrahydro-furan-(2R)-ylmethyl Ester

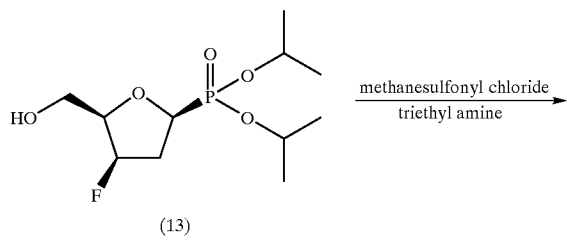

(13)

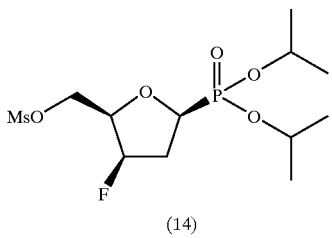

(14)

((4R)-Fluoro-(5R)-hydroxymethyl-tetrahydro-furan-(2S)-yl)-phosphonic acid diisopropyl ester (50 mg, 0.18 mmol) was dissolved in dichloromethane (2.5 ml) and cooled to 0° C. Triethylamine (45 μl, 0.32 mmol) and methanesulfonyl chloride (201 μl, 0.26 mmol) were added. After one hour saturated sodium bicarbonate solution was added. It was extracted with dichloromethane, washed with 0.1 N HCl and 2.5% NaHCO3 solution—saturated NaCl solution mixture, dried and evaporated giving almost pure mesylate (60 mg, 94%).

HNMR (δ, CDCl$_3$): 5.31 (1H, d with fine splitting, J=52.2 Hz), 4.74–4.84 (2H, m), 4.30–4.50 (4H, m), 3.07 (3H, s), 2.35–2.61 (2H, m), 1.34, 1.35, 1.36 (12H, d each, J=6.0 Hz). P$^{31}$ NMR (ppm; CDCl$_3$): 20.45 (singlet).

2.5) Preparation of [(5R)-(2-Amino-6-chloro-purin-9-ylmethyl)-(4R)-fluoro-tetrahydro-furan-(2S)-yl]-phosphonic Acid Diisopropyl Ester

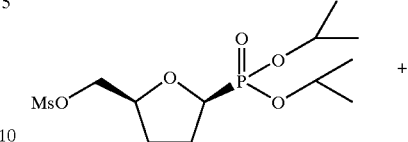

(14)

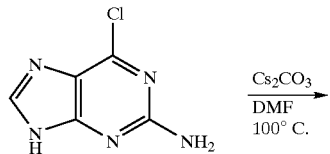

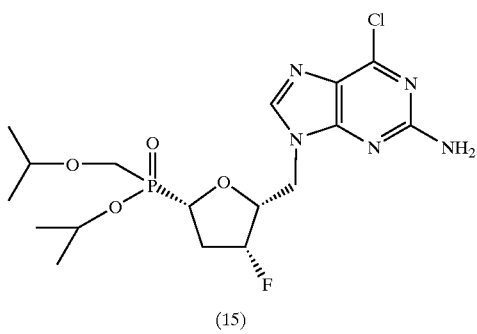

(15)

A mixture of 2-amino-6-chloropurine (45 mg, 0.27 mmol) and cesium carbonate (80 mg, 0.25 mmol) in DMF (0.5 ml) was stirred at 100° C. for 0.5 hr. Methanesulfonic acid (5S)-(diisopropoxy-phosphoryl)-(3R)-fluoro-tetrahydro-furan-(2R)-ylmethyl ester (60 mg, 0.17 mmol) in DMF (1 ml) was added dropwise during 5 minutes. The mixture was held at 100° C. for 7 hrs. It was cooled, filtered, evaporated and passed through a column of silica gel (2 and 5% methanol in CH$_2$Cl$_2$ as eluents) giving pure coupled product (23 mg, 32%).

HNMR (δ, CDCl$_3$): 7.84 (1 H, s), 5.16–5.31 (3H, one half of a doublet of a triplet under a big signal, J=50.4 Hz (for the doublet), 2.9 Hz (for the triplet)), 4.63–4.74 (2H, m), 4.42–4.52 (3H, m), 4.24–4.30 (1H, m), 2.37–2.59 (2H, m), 1.23, 1.28, 1.30 (12H, 3 doublets); C$^{13}$ NMR (ppm, CDCl$_3$): 159.1, 153.7, 151.2, 142.8, 125.0, 93.0 (dd, J=6, 184 Hz), 80.5 (dd, J=4.5, 18.0 Hz), 72.9 (d, J=176 Hz), 71.9 (d, J=7.1 Hz), 71.1 (d, J=7.1 Hz), 42.4 (d, J=13 Hz), 35.0 (d, J=21.6 Hz), 24.09, 24.06, 23.98, 23.94, 23.81, 23.76 (extra signals due to coupling with phosphorus); F$^{19}$ NMR (ppm, CDCl$_3$): −194.1 (multiplet); P$^{31}$ NMR (ppm, CDCl$_3$): 20.44 (singlet); LCMS 436.0.

2.6) Preparation of Ammonium; (5R)-(2-Amino-6-hydroxy-purin-9-ylmethyl)-(4R)-fluoro-tetrahydro-furan-(2S)-phosphonate

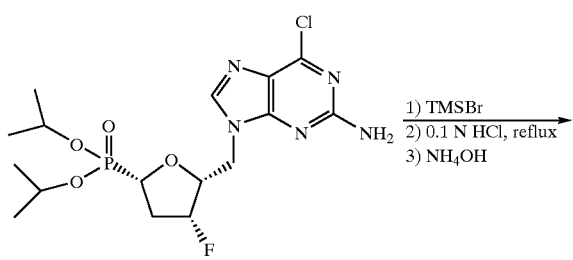

(15)

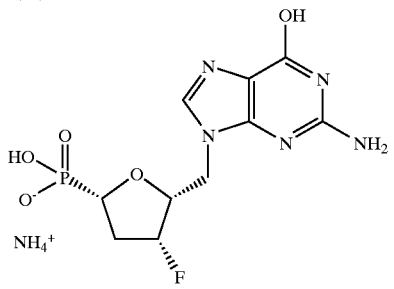

(16)

[(5R)-(2-Amino-6-chloro-purin-9-ylmethyl)-(4R)-fluoro-tetrahydro-furan-(2S)-yl]-phosphonic acid diisopropyl ester (23 mg, 0.05 mmol) was dissolved in $CH_2Cl_2$ (1.5 ml) and TMSBr (71 μl, 0.54 mmol) was added. The mixture was stirred at room temperature for 16 hrs. The reaction mixture was evaporated down to dryness and pumped for 1 hr. Hydrochloric acid (0.1 N, 1 ml) was added and the mixture was refluxed for 12 hrs. It was evaporated down to dryness and pumped for 2 hrs. The crude product was dissolved in $H_2O$ (10 ml) and the pH was brought to around 10 by adding $NH_4OH$. The solution was extracted with $CH_2Cl_2$ (2×10 ml) and the aqueous part was lyophilized giving 24 mg of solid. The solid was slightly overweighed because of the presence of ammonium salt. Attempts were made to remove the ammonium salts by passing it through a charcoal column, but were not successful. Finally ammonium salt was removed by washing with dry EtOH (2×1 ml) by stirring in a small vial. Solid thus obtained was dissolved in $H_2O$ and freeze-dried giving 14 mg of final product.

HNMR (δ, $D_2O$): 8.85 (1H, s), 5.39 (1H, d, J=53.5 Hz), 4.31–4.54 (4H, 3 complex signals), 2.41–2.53 (1H, m), 2.13–2.35 (1H, m); $F^{19}$ NMR (ppm, $D_2O$): −198.6 (m) (unreferenced); $P^{31}$ NMR (ppm, $D_2O$): 19.08 (s); LCMS: 334.1 (M-$NH_3$+1); HPLC: 95.9%.

EXAMPLE 3

Synthesis of (5R)-(2-Amino-6-hydroxy-purin-9-ylmethyl)-(4S)-fluoro-tetrahydro-furan-(2S)-phosphonate The synthesis is carried out following scheme 1C

SCHEME 1C

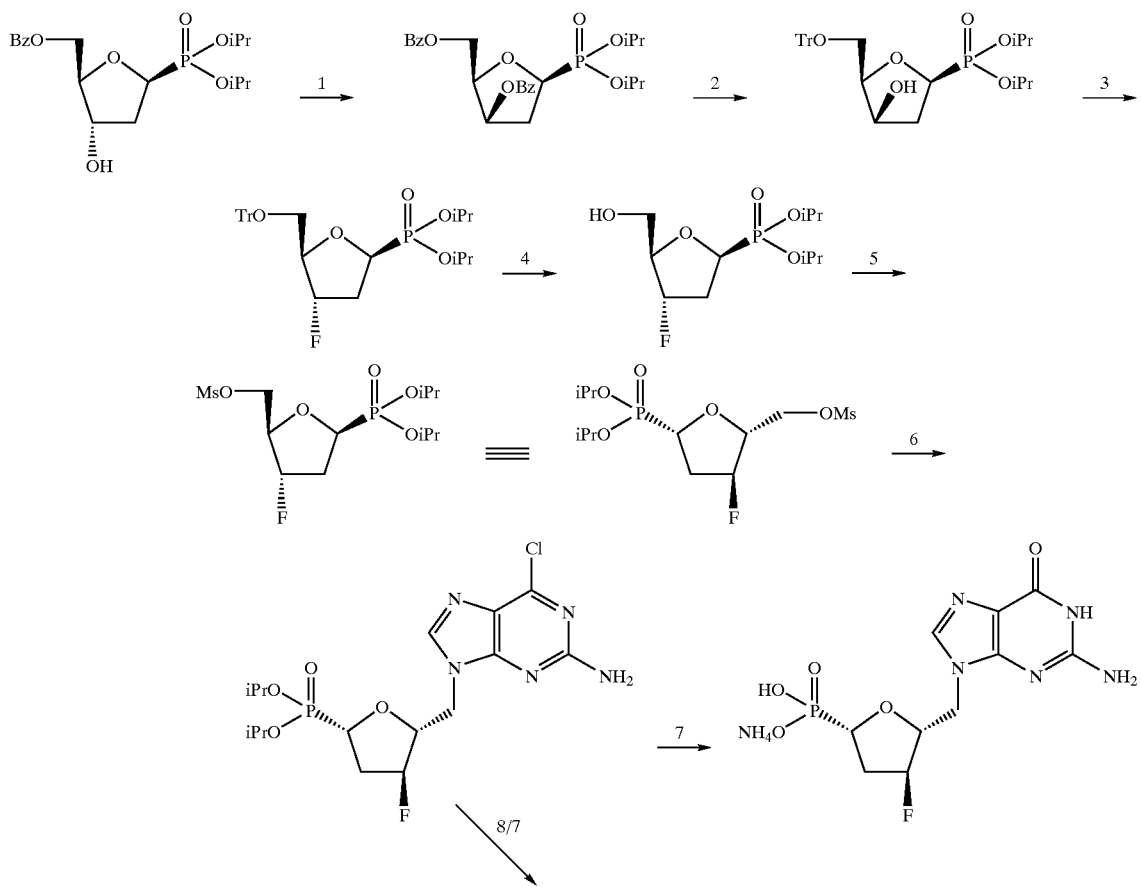

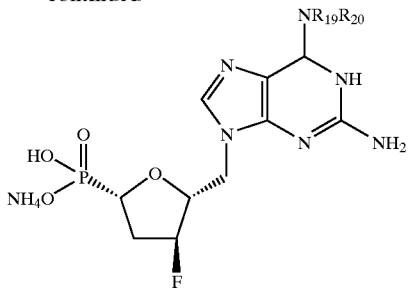

1) Benzoic acid, PPh$_3$, DEAD, ether; 2) a) MeOH, K$_2$CO$_3$; b) TrCl, pyridine; 3) DAST, pyridine; 4) aqu. 80% AcOH; 5) MsCl, Et$_3$N, CH$_2$Cl$_2$; 6) 2-amino-6-chloro-purine, CS$_2$CO$_3$, DMF, 100° C.; 7) a) TMSBr, CH$_2$Cl$_2$; b) aqu. HCl, reflux, c) NH$_4$OH, ethanol washing, 8) EtOH, NR$_{19}$R$_{20}$, 80° C.

3.1) Preparation of Benzoic Acid (5S)-(Diisopropoxy-phosphoryl)-(3R)-benzoyloxy-tetrahydro-furan-(2R)-ylmethyl Ester

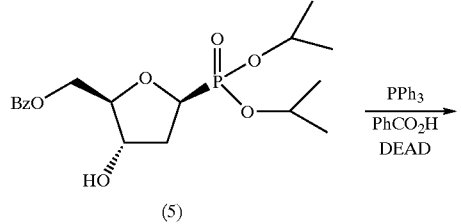

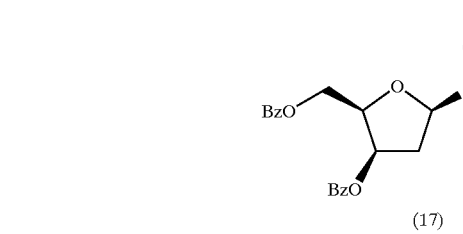

To a well-stirred mixture of benzoic acid (393 mg, 3.2 mmol) and DEAD (508 µl, 3.23 mmol) in ether (4 ml) was added dropwise a mixture of triphenyl phosphine (844 mg, 3.22 mmol) and benzoic acid (5S)-(diisopropoxy-phosphoryl)-(3S)-hydroxy-tetrahydro-furan-(2R)-ylmethyl ester (770 mg, 2.0 mmol) in ether (10 ml). The mixture was stirred at room temperature for 16 hrs.

Triphenylphosphine-oxide was separated by adding hexane-ether mixture (1:1). The liquid was taken out. The solid residue was further washed with hexane-ether mixture (1:1). The washings were combined with the liquid and evaporated. Dibenzoate was obtained by passing the crude product through a column of silica gel (CH$_2$Cl$_2$-acetone mixtures as eluents) (yield 1 g, the material contained bit of DEAD by-product).

H NMR (δ, CDCl$_3$): 8.03, 8.00 (4H, d each, J=7.2 Hz), 7.59, 7.55 (2H, t each, J=6.3 Hz), 7.45, 7.41 (4H, t each, J=7.4 Hz), 5.81 (1H, t, J=3.1 Hz), 4.74–4.89 (2H, m), 4.62–4.68 (2H, m), 4.55 (1H, dd, J=8.5, 14.3 Hz), 4.47 (1H, t, J=8.4 Hz), 2.64–2.76 (1H, m), 2.48 (1H, ddd, J=1.0,7.0, 14.6 Hz), 1.34, 1.35, 1.36 (12H, d each, J=5.8 Hz).

3.2) Preparation of ((4R)-Hydroxy-(5R)-trityloxymethyl-tetrahydro-furan-(2S)-yl)-phosphonic Acid Diisopropyl Ester

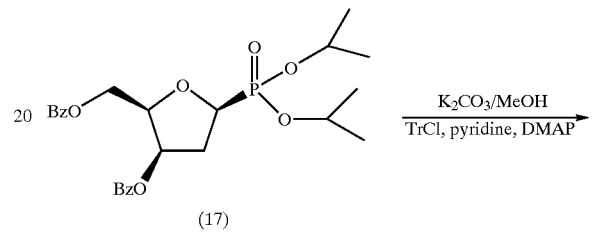

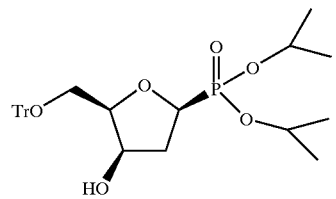

The benzoic acid (5S)-(diisopropoxy-phosphoryl)-(3R)-benzoyloxy-tetrahydro-furan-(2R)-yl methyl ester (1.0 g) was hydrolyzed with K$_2$CO$_3$ (25 mg) in methanol (50 ml) at room temperature (16 hrs). The mixture was neutralized with acidic resin. It was filtered and evaporated. Pure dihydroxy product was obtained by column chromatography of the crude product over silica gel (CH$_2$Cl$_2$-MeOH=98:2 as eluent) (450 mg).

The dihydroxy product obtained above (450 mg, 1.6 mmol) was dissolved in CH$_2$Cl$_2$ (20 ml) and cooled to 0° C. Pyridine (0.25 ml) and DMAP (catalytic) were added followed by trityl chloride (680 mg, 2.44 mmol). The reaction was slow at 0° C. It was stirred at room temperature for 1.5 hr. Saturated NaHCO$_3$ solution was added and it was extracted with CH$_2$Cl$_2$. The extracts were washed with 1N HCl (quickly) followed by 2.5% NaHCO$_3$-saturated NaCl mixture, dried and evaporated. Pure mono-trityl derivative was obtained by passing the crude material through a column of silica gel (CH$_2$Cl$_2$-acetone:9:1 as eluent) (yield= 675 mg, 65% from the mono-benzoate).

HNMR (δ, CDCl$_3$): 7.24–7.46 (15H, aromatic protons), 4.73–4.85 (2H, m), 4.57–4.58 (1H, broad signal), 4.42 (1H, ddd, J=2.4, 7.1, 9.7 Hz), 4.20–4.23 (1H, m), 3.47 (1H, dd, J=4.2, 9.8 Hz), 3.38 (1H, dd, J=6.5, 9.8 Hz), 2.69 (1H, d, J=3.3 Hz), 2.23–2.44 (2H, 2 multiplets), 1.37, 1.36, 1.33 (12H, d each, J=5.8 Hz).

3.3) Preparation of ((4S)-Fluoro-(5R)-trityloxymethyl-tetrahydro-furan-(2S)-yl)phosphonic Acid Diisopropyl Ester

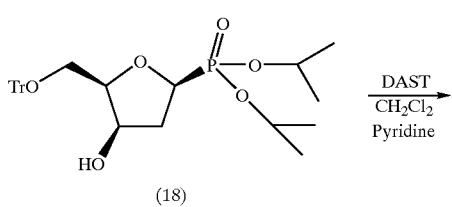

(18)

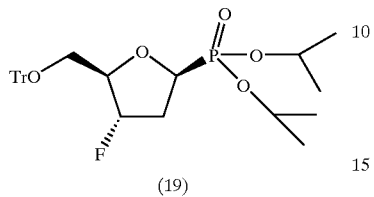

(19)

((4R)-Hydroxy-(5R)-trityloxymethyl-tetrahydro-furan-(2S)-yl)-phosphonic acid diisopropyl ester (575 mg, 1.09 mmol) was dissolved in CH$_2$Cl$_2$ (10 ml). DAST (287 μl, 2.18 mmol) was added. After 5 minutes the reaction mixture was treated with pyridine (0.871 ml, 10.9 mmol) and was stirred at room temperature for 16 hrs. Saturated NaHCO$_3$ solution was added slowly to the cooled mixture and stirred for 10 minutes. It was extracted with CH$_2$Cl$_2$ (2×100 ml), dried, evaporated and passed through two columns of silica gel to obtain pure fluoro-compound (153 mg, 27%)(CH$_2$Cl$_2$-acetone mixtures as eluents).

HNMR (δ, CDCl$_3$): 7.11–7.53 (15H, aromatic protons), 5.20 (1H, d of two complex signals, J=55.5 Hz), 4.80–4.88 (2H, m), 4.42–4.49 (2H, m), 3.31 (1H, dd, J=4.4, 10.1 Hz), 3.15 (1H, dd, J=3.6,10.1 Hz), 2.43–2.80 (2H, m), 1.39,1.38 (12H, d each, J=4.9 Hz). P$^{31}$ NMR (ppm, CDCl$_3$): 20.4 (s); F$^{91}$ NMR (ppm, CDCl$_3$): −179.9 (multiplet) (unreferenced).

3.4) Preparation of ((4S)-Fluoro-(5R)-hydroxymethyl-tetrahydro-furan-(2S)-yl)-phosphonic Acid Diisopropyl Ester

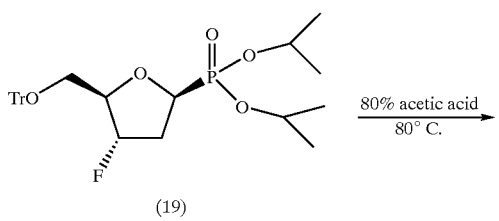

(19)

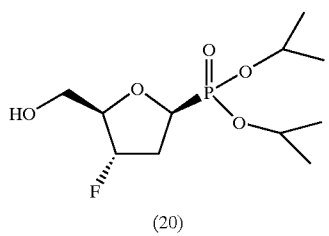

(20)

((4S)-Fluoro-(5R)-trityloxymethyl-tetrahydro-furan-(2S)-yl)-phosphonic acid diisopropyl ester (140 mg, 0.27 mmol) was treated with 80% acetic acid (5 ml) and held at 80° C. for 40 minutes. The mixture was evaporated down to dryness and purified by passing through a column of silica gel (CH$_2$Cl$_2$-methanol mixtures as eluents) (yield: 72 mg, 95%).

HNMR (δ, CDCl$_3$): 5.21 (1H, d of two complex signals, J=55.8 Hz), 4.71–4.80 (2H, m), 4.26–4.33 (2H, m), 3.63–3.73 (2H, m), 3.08 (1H, broad signal), 2.35–2.69 (2H, m), 1.34, 1.32, 1.31 (12H, d each, J=4.7 Hz); C$^{31}$ NMR (ppm, CDCl$_3$): 93.4 (dd, J=5.6, 181.5 Hz), 85.2 (dd, J=6.4, 24.1 Hz), 73.8 (d, J=176 Hz), 71.6 (d, J=7.0 Hz), 71.4 (d, J=7.1 Hz), 61.6 (d, J=7.2 Hz), 34.4 (d, J=22 Hz), 24.1, 23.9, 23.84, 23.80; F$^{19}$ NMR (ppm, CDCl$_3$): −184.5 (multiplet) (unreferenced); P$^{31}$ NMR (ppm, CDCl$_3$): 20.54 (singlet).

3.5) Preparation of Methanesulfonic Acid (5S)-(Diisopropoxy-phosphoryl)-(3S)-fluoro-tetrahydro-furan-(2R)-ylmethyl Ester

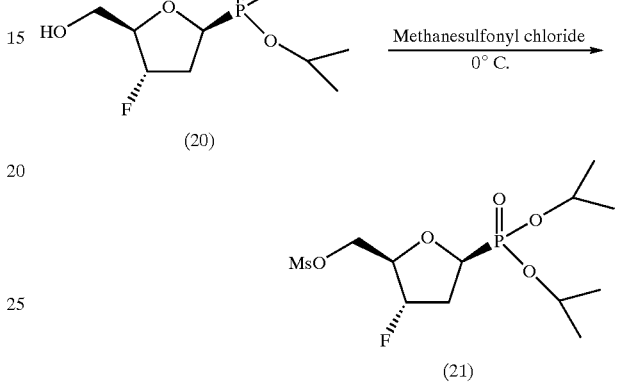

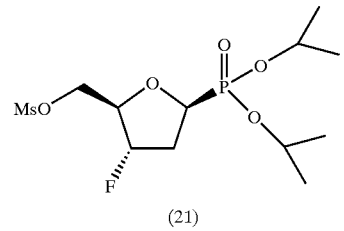

(21)

((4S)-Fluoro-(5R)-hydroxymethyl-tetrahydro-furan-(2S)-yl)-phosphonic acid diisopropyl ester (72 mg, 0.25 mmol) in CH$_2$Cl$_2$ (2.5 ml) was treated with triethyl amine (53 μl, 0.38 mmol) and methanesulfonyl chloride (24 μl, 0.31 mmol) at 0° C. After 0.5 hr saturated NaHCO$_3$ solution was added and the mixture was stirred for 5 minutes. It was extracted with CH$_2$Cl$_2$. The extract was washed with 0.1N HCl followed by 2.5% NaHCO$_3$ solution-NaCl solution mixture, dried and evaporated. The crude product (90 mg, 98%) was pure enough for the next step.

HNMR δ, CDCl$_3$): 5.20 (1H, d of two complex signals, J=55.2 Hz), 4.74–4.86 (2H, m), 4.50 (1H, ddd, J=3.7, 7.5, 19.6 Hz), 4.254.41 (3H, m), 3.06 (3H, s), 2.44–2.74 (2H, m), 1.36, 1.35 (12H, d each, J=5.2 Hz). P$^{31}$ NMR (ppm, CDCl$_3$): 19.6 (singlet).

3.6) Preparation of [(5R)-(2-Amino-6-chloro-purin-9-ylmethyl)-(4S)-fluoro-tetrahydro-furan-(2S)-yl]-phosphonic Acid Diisopropyl Ester

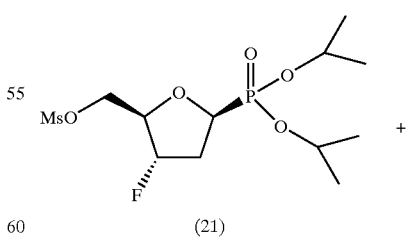

(21)

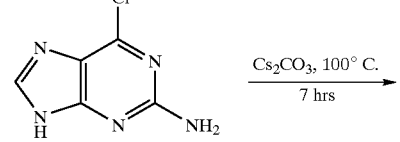

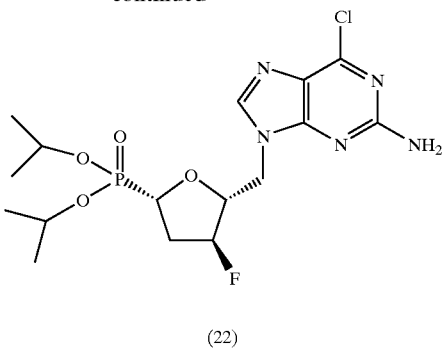

(22)

A mixture of 2-amino-6-chloro-purine (70 mg, 0.41 mmol) and cesium carbonate (130 mg, 0.40 mmol) in DMF (0.5 ml) was stirred at 100° C. for one hour. A solution of methanesulfonic acid (5S)-(diisopropoxy-phosphoryl)-(3S)-fluoro-tetrahydro-furan-(2R)-ylmethyl ester (90 mg, 0.25 mmol) in DMF (1.5 ml) was added dropwise during 5 minutes. The mixture was held at 100° C. for 7 hrs. It was cooled, filtered, evaporated and passed through a column of silica gel (CH$_2$Cl$_2$-methanol mixtures as eluents) giving 47 mg pf pure coupled product (yield: 43%).

HNMR ($\delta$, CDCl$_3$): 7.82 (1H, s), 5.30 (2H, broad signal), 4.97 (1H, d of a complex signal, J=55.0 Hz), 4.68–4.81 (2H, m), 4.56 (1H, dq, J=4.6, 18.2 Hz), 4.25–4.33 (2H, m), 4.21 (1H, t, J=8.0 Hz), 2.32–2.56 (2H, m), 1.32, 1.29 (12H, d each, J=6.1 Hz); C$^{13}$ NMR (ppm, CDCl$_3$): 159.3, 153.9, 151.3, 142.8, 124.5, 92.6 (dd, J=5.2, 186 Hz), 81.8 (dd, J=4.8, 26.5 Hz), 73.1 (dd, J=3.2, 174.1 Hz), 71.8 (d, J=7.2Hz), 71.4 (d, J=6.7 Hz), 43.5 (d, J=4.7 Hz), 33.3 (d, J=21.7 Hz), 24.09, 24.06, 24.03, 23.98, 23.95, 23.88, 23.83, 23.77 (few extra signals due to the coupling with Phosphorus); F$^{19}$ NMR (ppm, CDCl$_3$): −188.5 (multiplet) (unreferenced); P$^{31}$ NMR (ppm, CDCl$_3$): 19.5 (singlet). LCMS :436.1 (M+1).

3.7) Preparation of Ammonium; (5R)-(2-Amino-6-hydroxy-purin-9-ylmethyl)-(4S)-fluoro-tetrahydro-furan-(2S)-phosphonate

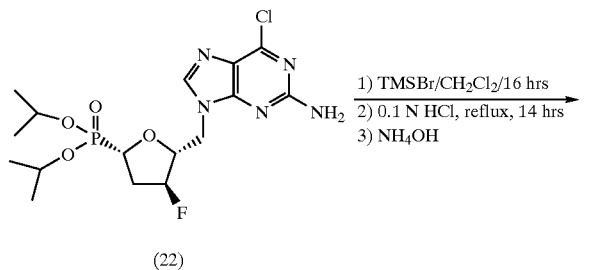

(22)

1) TMSBr/CH$_2$Cl$_2$/16 hrs
2) 0.1 N HCl, reflux, 14 hrs
3) NH$_4$OH (23)

To a solution of [(5R)-(2-amino-6-chloro-purin-9-ylmethyl)-(4S)-fluoro-tetrahydro-furan-(2S)-yl]-phosphonic acid diisopropyl ester (42 mg, 0.096 mmol) in CH$_2$Cl$_2$ (2.7 ml) was added bromotrimethyl silane (130 µl, 0.98 mmol). The mixture was stirred at room temperature for 16 hrs. It was evaporated to dryness and 0.1 N HCl (1.5 ml) was added. The mixture was refluxed for 14 hrs. The reaction mixture was evaporated to dryness and pumped for 2 hrs. It was dissolved in water (10 ml) and extracted with CH$_2$Cl$_2$ (50 ml). The aqueous part was brought to pH around 10 with ammonium hydroxide and extracted again with CH$_2$Cl$_2$ (2×50 ml). The aqueous part was lyophilized giving 48 mg of solid product. The solid was triturated with small volumes of dry ethanol (2×1 ml and 1×0.5 ml), dissolved in water (5 ml) and lyophilized yielding 33 mg of product (98%).

HNMR ($\delta$, D$_2$O): 7.75 (1H, s), 5.16 (dd, J=5.8, 53.2 Hz), 4.52 (1H, ill-defined dt, J=20.0 Hz), 4.04–4.17 (3H, m), 2.38–2.57 (1H, m), 2.15–2.33 (1H, m) P$^{31}$ NMR (ppm, D$_2$O): 16.44 (singlet); F$^{19}$ NMR (ppm, D$_2$O): −180.35 (multiplet) (unreferenced). LCMS: 334.2 (M-NH$_3$+1); HPLC: 99%

EXAMPLE 4

Synthesis of (5R)-(2-Amino-6-hydroxy-purin-9-ylmethyl)-(4S)-hydroxy-tetrahydro-furan-(2S)-phosphonate.

The synthesis is carried out following Scheme 1D:

SCHEME 1D

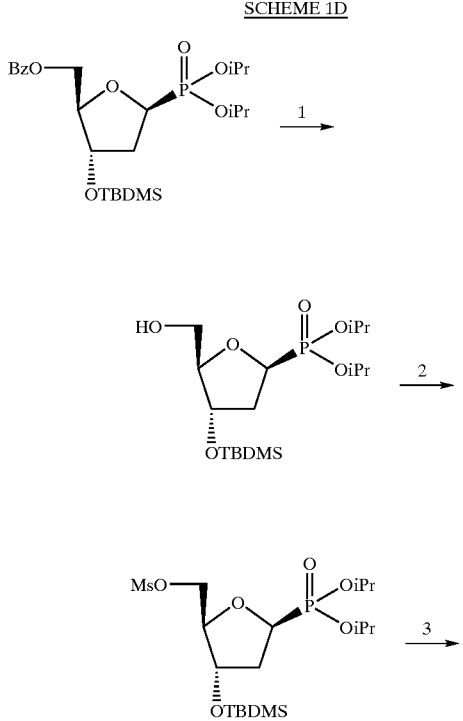

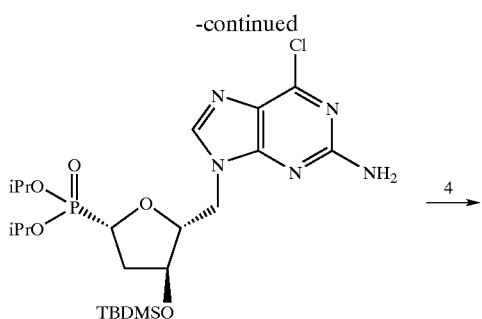

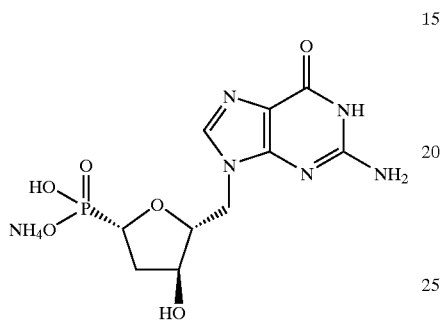

1) MeOH, aq.K₂CO₃; 2) MsCl, Et₃N, CH₂Cl₂; 3)2-amino-6-Cl-purine, Cs₂CO₃, DMF 100° C.; 4) a) TMSBr, CH₂Cl₂, b) aqu. HCl, reflux, c) Crystallization NH₄OH.

4.1) Preparation of (4S)- (tert-Butyl-dimethyl-silanyloxy -(5R)-(hydroxymethyl-tetrahydro-furan-(2S)-yl)-phosphonic Acid Diisopropyl Ester

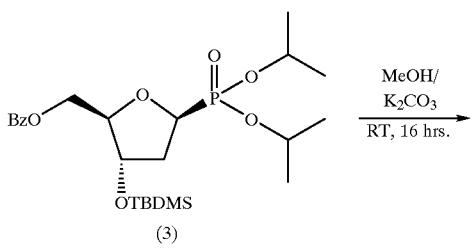

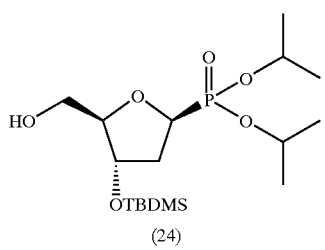

Benzoic acid (3S)-(tert-butyl-dimethyl-silanyloxy)-(5S)-(diisopropoxy-phosphoryl)-tetrahydro-furan-(2R)-ylmethyl ester (200 mg) was dissolved in MeOH (5 ml) and K₂CO₃ (5 mg) was added. It was stirred for 16 hrs. at room temperature. The mixture was neutralized with acidic resin, filtered, evaporated and dried under high vacuum for two hours. It gave 160 mg of desired product containing some benzoic acid methyl ester as impurity.

¹H-NMR (δ; CDCl₃): 4.76–4.85 (2H, m); 4.32–4.36 (1H, m); 4.16–4.20 (1H, m); 3.83–3.88 (1H, m); 3.77–3.81 (1H, m); 3.56–3.62 (1H, m); 2.39–2.47 (1H, m); 2.11–2.24 (1H, m); 1.73–1.76 (1H, m, D₂O exchangeable); 1.35–1.37 (12H, m); 0.89 (9H, s); 0.09 (6H, s). ³¹P-NMR (δ; CDCl₃): 21.35 (s).

4.2) Preparation of Methanesulfonic Acid (3S)-(tert-butyl-dimethyl-silanyloxy)-(5S)-(diisopropoxy-phosphoryl)-tetrahydro-furan-(2R)-ylmethyl Ester

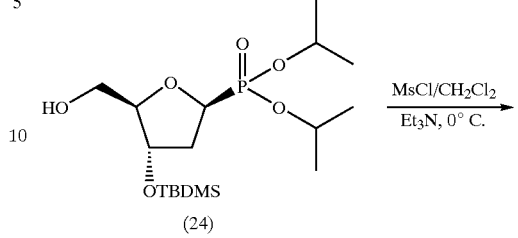

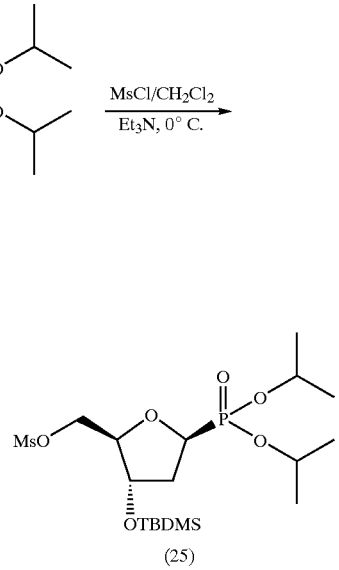

(4S)- (tert-butyl-dimethyl-silanyloxy)-(5R)-(hydroxymethyl-tetrahydro-furan-(2S)-yl)-phosphonic acid diisopropyl ester (166 mg) in CH₂Cl₂ (5 ml) was treated with triethyl amine (81 µl, 1.5 eq.) and methanesulfonyl chloride (36 µl, 1.2eq.) at 0° C. After 1 hr saturated NaHCO₃ solution was added and the mixture was stirred for 5 minutes. It was extracted with CH₂Cl₂. The extract was washed with 0.1N HCl followed by 2.5% NaHCO₃ solution-NaCl solution mixture, dried and evaporated. The crude product (170 mg) was pure enough for the next step.

¹H-NMR δ, CDCl₃): 4.69–4.80 (2H, m), 4.31–4.39 (1H, m), 4.06–4.28 (3H, m), 3.90–3.94 (1H, m); 3.01 (3H, s), 2.38–2.46 (1H, m), 2.08–2.21 (1H, m); 1.29, 1.32 (12H,m); 0.85 (9H, s); 0.05 (6H, s).

4.3) [(5R)-(2-Amino-6-chloro-purin-9-ylmethyl)-(4S)-(tert-butyl-dimethyl-silanyloxy)-tetrahydro-furan-(2S)-yl]-phosphonic Acid Diisopropyl Ester

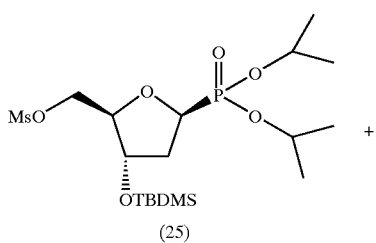

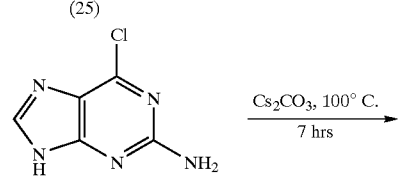

-continued

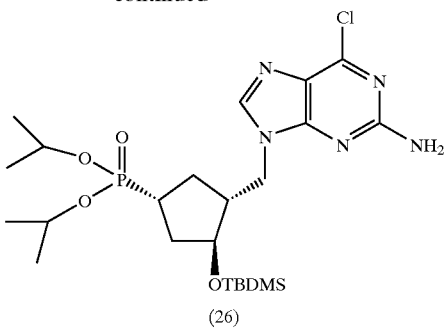

(26)

A mixture of 2-amino-6-chloro-purine (164 mg) and cesium carbonate (314 mg) in DMF (3 ml) was stirred at 100° C. for one hour. A solution of methanesulfonic acid (3S)-(tert-butyl-dimethyl-silanyloxy)-(5S)-(diisopropoxy-phosphoryl)-tetrahydro-furan-(2R)-ylmethyl ester (285 mg) in DMF (2 ml) was added dropwise during 10 minutes. The mixture was held at 100° C. for 5 hrs. It was cooled, filtered and washed with little DMF. The filtrate was evaporated under reduced pressure and the residue was dissolved in methylene chloride. The organic solution was washed with water, brine, dried over $MgSO_4$ and filtered. The filtrate was evaporated under reduced pressure to give a crude product (350 mg), which was purified on silica gel column using a gradient of 2–6% methanol in methylene chloride as eluent. It gave 150 mg of desired product.

$^1$H-NMR ($\delta$; $CDCl_3$): 7.92 (1H, s); 5.04 (2H, broad s, $D_2O$ exchangeable); 4.69–4.81 (2H, m); 4.24–4.32 (2H, m); 4.05–4.11 (2H,m); 3.84–3.90 (1H,m); 2.32–2.41 (1H, m); 2.10–2.23 (1H, m); 1.32–1.34 (12H, m), 0.91 (9H, s); 0.09 (6H, s). $^{31}$P-NMR (ppm,$CDCl_3$): 20.54 (s).

4.4) Preparation of Ammonium; (5R)-(2-Amino-6-hydroxy-purin-9-ylmethyl)-(4S)-hydroxy-tetrahydro-furan-(2S) phosphonate.

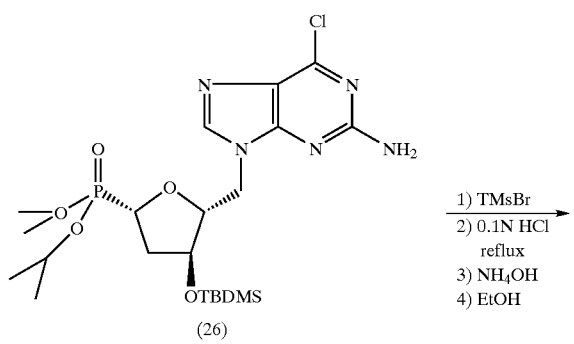

To a solution of [(5R)-(2-Amino-6-chloro-purin-9-ylmethyl)-(4S)-(tert-butyl-dimethyl-silanyloxy)-tetrahydro-furan-(2S)-yl]-phosphonic acid diisopropyl ester (484 mg) in dichloromethane (17 ml) was added bromotrimethyl silane (1.2 ml) and the mixture was stirred at room temperature for 16 hrs. The reaction mixture was evaporated to dryness and residue was dried on high vacuum for two hours. Hydrochloric acid (0.1 N, 14 ml) was added and the mixture was refluxed for 12 hrs. At the end of this period, the conversion to guanine derivative was completed by following UV spectra. The mixture was evaporated to dryness and pumped for 1 hr. The residue was dissolved in water (20 ml) and adjusted to pH≈10 with ammonium hydroxide. The solution was extracted with dichloromethane (2×30 ml). The aqueous phase was lyophilized giving 510 mg of solid product (slightly overweighed). It contained $NH_4Cl$ salt.

The solid product was re-dissolved in water (12 ml) and brought to pH between 2–2.3 by adding conc. HCl (few drops). Ethanol (25 ml) was added slowly and white solid precipitated. The mixture was placed in cold room for three hours. The solid was collected by filtration, washed with ethanol-water (2:1) and dissolved in 5% ammonium hydroxide (20 ml). The solution was lyophilized to give 244 mg of $NH_4Cl$ salt-free product (NMR in $d_6$-DMSO was indicative of the absence of $NH_4$-salt).

$[\alpha_D]$=+8.0 (c:0.3); $^1$H-NMR ($\delta$; $D_2O$): 7.75 (1H, s); 4.004.16 (5H, m); 2.20–2.30 (1H, m); 1.91–2.02 (1H, m). $^{13}$C-NMR ($\delta$; $D_2O$): 158.48 (s); 153.30(s); 151.32 (s); 140.15 (s); 115.16 (s); 82.85 (d, 5 Hz); 73.98 (d, 160 Hz); 72.49 (d, 6 Hz); 44.02 (s); 34.69(s). $^{31}$P-NMR ($\delta$; $D_2O$): 17.49 (s).

EXAMPLE 5

Ammonium; 5-(2-Amino-6yclopropylamino-purin-9-ylmethyl)-4-hydroxy-tetrahydro-furan-2-phosphonate

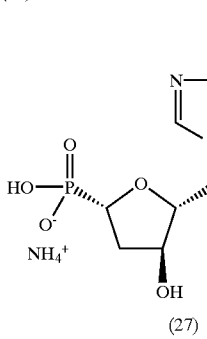

COMPOUND M

Procedure

To a solution of chloropurine (120 mg, 0.22 mmol) in ethanol (2 mL) at rt was added cyclopropylamine (0.15 mL, 2.2 mmol). The mixture was stirred overnight and the volatiles were removed under vacuo. The residue was the dissolved in dichloromethane (2 mL) and TMSBr (0.29 mL, 2.2 mmol) was added. After stirring at rt overnight, the reaction mixture was concentrated to dryness and methanol 92 mL0 was then added. The solution was again concentrated to dryness and the residue was dissolved in water. This solution was then washed with dichloromethane (2×), pentane (1×) and lyophilized. Purification by a charcoal chromatography eluting with 5–20% aqueous ammonia gave the desired compound as a white solid (52 mg, 61%)

$^{1}$H NMR (400 MHz, D$_2$O) δ: 0.62 (d, 2H, J=6.8 Hz), 0.84 (d, 2H, J=6.5 Hz), 1.9 (m, 1H), 2.3 (m, 1H), 2.75 (m, 1H), 4.1 (m, 5H), 7.78 (s, 1H). $^{31}$P NMR (162 MHz, D$_2$O) δ: 18.44.

EXAMPLE 6

Acetic Acid 6-(diisopropoxy-phosphoryl)-2,2-dimethyl-tetrahydro-furo[3,4-d][1,3]dioxol-4-ylmethyl Ester

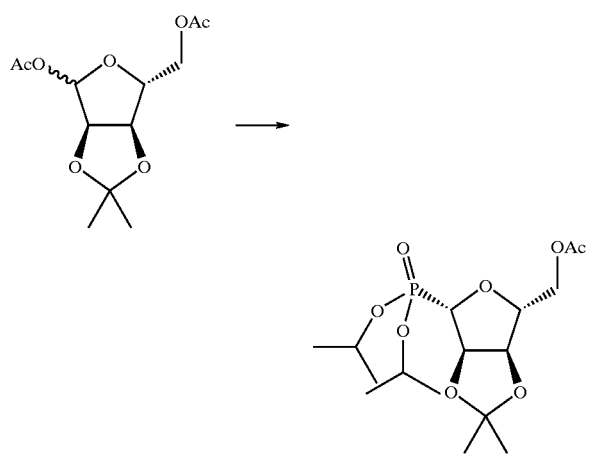

Procedure

To a solution of acetic acid 6-acetoxy-2,2-dimethyl-tetrahydro-furo[3,4-d][1,3]dioxol-4-ylmethyl ester (623 mg, 2.27 mmol) in dichloromethane (3 mL) was added iodotrimethylsilane (0.35 mL, 2.49 mmol) at −78° C. and the reaction mixture brought to RT. After confirming the disappearance of starting material by TLC, triisopropylphosphite (1.18 mL, 5.68 mmol) was added at −78° C. The reaction mixture was left to warm to RT and stirred overnight. The reaction was quenched with sodium bicarbonate, extracted with dichoromethane, the organic layers concentrated, dried and chromatographed. Elution with 50% ethylacetate/hexanes gave acetic acid 6-(diisopropoxy-phosphoryl)-2,2-dimethyl-tetrahydro-furo[3,4-d][1,3]dioxol-4-ylmethyl ester as a colorless syrup (467 mg, 54%).

$^{1}$H nmr (400 MHz, CDCl$_3$) δ: 1.37 (m, 15H (5Me)), 1.58 (s, 3H (Me)), 2.08 (s, 3H (OAc)), 4.10 (m, 2H), 4.21 (m, 1H), 4.42 (m, 1H), 4.68 (m, 1H), 4.85 (m, 2H (OCH)), 5.01 (m, 1H, H$_1$).

EXAMPLE 7

(6-Hydroxymethyl-2,2-dimethyl-tetrahydro-furo[3,4-d][1,3]dioxol4-yl)- phosphonic Acid Diisopropyl Ester

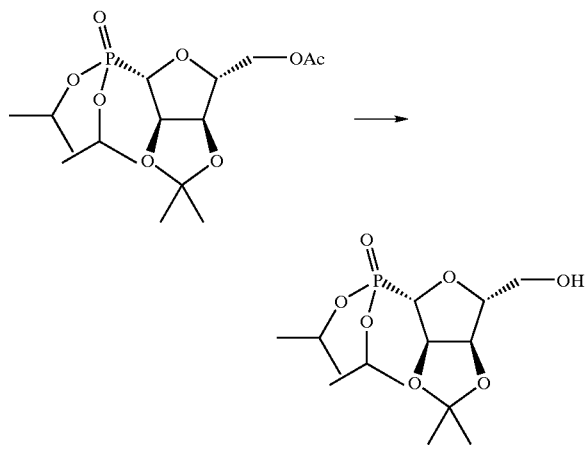

Procedure

Acetic acid 6-(diisopropoxy-phosphoryl)-2,2-dimethyl-tetrahydro-furo[3,4-d][1,3]dioxol-4-ylmethyl ester (467 mg, 1.22 mmol) in dry methanol (10 mL) and methanolic sodium methoxide (0.1M, 1 mL) was stirred at RT for 0.5 h. Dowex acidic resin was added until neutral pH was attained, the reaction mixture filtered and concentrated to give (6-Hydroxymethyl-2,2-dimethyl-tetrahydro-furo[3,4-d][1,3]dioxol-4-yl)-phosphonic acid diisopropyl ester as a colorless syrup (409 mg, 99%).

$^{1}$H nmr (400 MHz, CD$_3$OD) δ: 1.36 (m, 15H (5Me)), 1.52 (s, 3H (Me)), 3.62 (d, 2H), 4.15 (m, 1H), 4.35 (m, 1H), 4.80 (m, 3H), 4.99 (m, 1H).

EXAMPLE 8

[6-(2-Amino-6-chloro-purin-9-ylmethyl)-2,2-dimethyl-tetrahydro-furo[3,4-d][1,3]dioxol4-yl]-phosphonic Acid Diisopropyl Ester

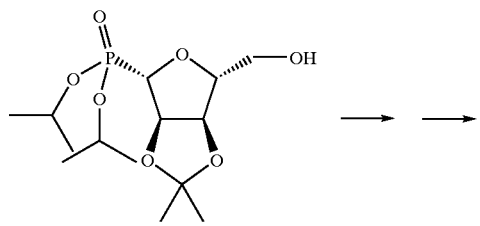

53
-continued

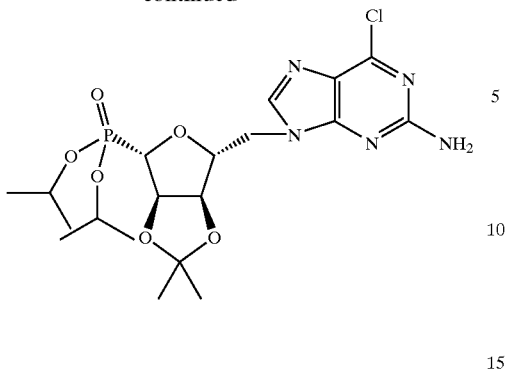

Procedure

To a solution of (6-Hydroxymethyl-2,2-dimethyl-tetrahydro-furo[3,4-d][1,3]dioxol-4-yl)-phosphonic acid diisopropyl ester (404 mg, 1.19 mmol) in dichloromethane (10 mL) and dry triethylamine (0.21 mL, 1.52 mmol) was added mesyl chloride dropwise at 0° C. and stirred for one hour. The reaction mixture was poured into saturated sodium bicarbonate and extracted with dichloromethane. The organic layers were combined, dried over sodium sulfate and concentrated to give the mesylate as a colorless syrup (515 mg). The mesylate (281 mg, 0.67 mmol) was dissolved in DMF (7 mL) and transferred via cannula to a solution of cesium carbonate (314 mg, 1.18 mmol) and 2-amino-6-chloropurine (301 mg, 1.18 mmol) in DMF (7 mL) which had been previously heated at 100° C. for 0.5 hour . After stirring at 100° C. for 4 hrs, the reaction mixture was then concentrated and chromatographed, eluting with 4% methanol/dichloromethane to give [6-(2-Amino-6-chloro-purin-9-ylmethyl)-2,2-dimethyl-tetrahydro-furo[3,4-d][1,3]dioxol-4-yl]-phosphonic acid diisopropyl ester (70 mg, 21%) as a white foam.

$^1$H nmr (400 MHz, CD$_3$OD) δ: 1.29 (d, 3H (Me)), 1.41(m, 15H (4Me)), 1.52 (s, 3H (Me)), 4.23 (d, 2H), 4.42 (dd, 1H), 4.61 (m, 1H), 4.72 (m, 3H), 5.06 (m, 1H), 8.10 (s, 1H (CH=N)).

EXAMPLE 9

Ammonium; 5-(2-Amino-6-oxo-1,6-dihydro-purin-9-ylmethyl)-3,4-dihydroxy-tetrahydro-furan-2-phosphonate

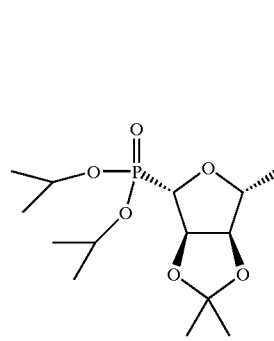

54
-continued

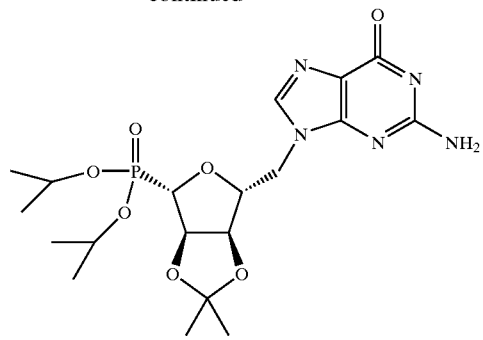

Procedure

To [6-(2-Amino-6-chloro-purin-9-ylmethyl)-2,2-dimethyl-tetrahydro-furo[3,4-d][1,3]dioxol-4-yl]-phosphonic acid diisopropyl ester (61 mg, 0.12 mmol) was added bromotrimethylsilane (0.32 mL, 2.49 mmol) and stirred at RT under nitrogen overnight. The reaction mixture was concentrated to give a bright yellow solid which was dissolved in 1N HCl/water (0.4 mL/2 mL) and refluxed overnight. Conversion to guanine was confirmed by uv spectroscopy. The reaction mixture was extracted 2× with dichloromethane and 1× with pentane. The aqueous layer was lyophilized, dissolved in a small amount of water, and passed through a short charcoal column eluting with 0.5% ammonium hydroxide/water. The fractions were combined and lyophilized to give Ammonium; 5-(2-amino-6-oxo-1,6-dihydro-purin-9-ylmethyl)-3,4-dihydroxy-tetrahydro-furan-2-phosphonate as a white fluffy solid (25 mg, 56%).

$^1$H nmr (400 MHz, D$_2$O) δ: 3.82 (m, 2H), 4.11 (m, 2H), 4.23 (m, 2H), 7.80 (s, 1H (CH=N)); $^{31}$P nmr (400 MHz, D$_2$O) δ: 13.7.

EXAMPLE 10

Ammonium; 5-(2-Amino-6-oxo-1,6-dihydro-purin-9-ylmethyl)-3,4-dihydroxy-tetrahydro-furan-2-phosphonate

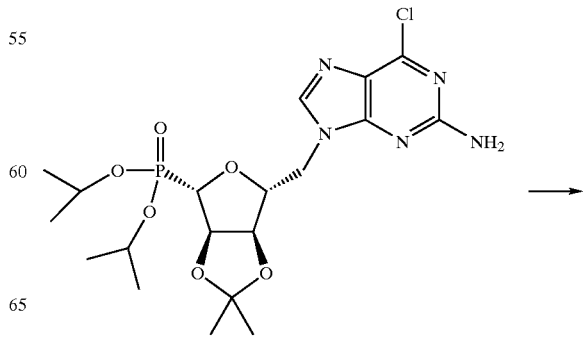

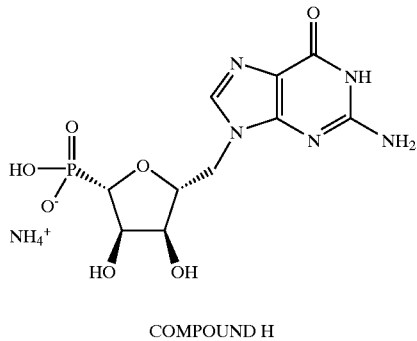

COMPOUND H

Procedure

To [6-(2-Amino-6-chloro-purin-9-ylmethyl)-2,2-dimethyl-tetrahydro-furo[3,4-][1,3]dioxol-4-yl]-phosphonic acid diisopropyl ester (61 mg, 0.12 mmol) was added bromotrimethylsilane (0.32 mL, 2.49 mmol) and stirred at RT under nitrogen overnight. The reaction mixture was concentrated to give a bright yellow solid which was dissolved in 1N HCl/water (0.4 mL/2 mL) and refluxed overnight. Conversion to guanine was confirmed by uv spectroscopy. The reaction mixture was extracted 2× with dichloromethane and 1× with pentane. The aqueous layer was lyopholized, dissolved in a small amount of water, and passed through a short charcoal column eluting with 0.5% ammonium hydroxide/water. The fractions were combined and lyopholized to give Ammonium; 5-(2-amino-6-oxo-1,6-dihydro-purin-9-ylmethyl)-3,4-dihydroxy-tetrahydro-furan-2-phosphonate as a white fluffy solid (25 mg, 56%).

$^1$H nmr,(400 MHz, D$_2$O) δ: 3.82 (m, 2H), 4.11 (m, 2H), 4.23 (m, 2H), 7.80 (s, 1H (CH=N)); $^{31}$P nmr (400 MHz, D$_2$O) δ: 13.7.

EXAMPLE 11

[5-(2-Amino-6-chloro-purin-7-ylmethyl)tetrahydro-furan-2-yl]-phosphonic Acid Diethyl Ester

[5-(2-Amino-6-chloro-purin-9-ylmethyl)tetrahydro-furan-2-yl]-phosphonic Acid Diethyl Ester

Procedure

A solution of (5-Bromomethyl-tetrahydro-furan-2-yl)-phosphonic acid diethyl ester (1.0, 3.32 mmol) in DMF (7mL) was transferred via cannula to a solution of cesium carbonate (1.31 g, 4.98 mmol) and 2-amino-6-chloropurine (845 mg, 4.98 mmol) in DMF (7 mL) which had been previously heated at 100° C. for 0.5 hour . The reaction mixture was stirred at 100° C. for 3 hrs. The reaction mixture was then concentrated and chromatographed, eluting with 8% methanol/dichloromethane to give [5-(2-Amino-6-chloro-purin-7-ylmethyl)-tetrahydro-furan-2-yl]-phosphonic acid diethyl ester (78 mg, 6%):

$^1$H nmr (400 MHz, CDCl$_3$) δ: 1.33 (t, J=7.0 Hz, 6H (2Me)), 1.56 (m, 1H), 2.0–2.2 (m, 3H), 4.15 (m, 6H), 4.31 (dd, J=3.2, 14.5 Hz,1H), 4.48 (m, 1H), 7.93 (s, 1H, CH=N); $^{31}$P nmr (400 MHz, CDCl$_3$) δ: 23.3. Further elution gave [5-(2-Amino-6-chloro-purin-9-ylmethyl)-tetrahydro-furan-2-yl]-phosphonic acid diethyl ester (425 mg, 34%) as white foam.

$^1$H nmr (400 MHz, CD$_3$OD) δ: 1.29 (m, 6H (2Me)), 1.76 (m, 1H), 2.1–2.4 (m, 3H), 4.05 (m, 3H), 4.30 (m, 1H), 4.43 (m, 2H), 4.62 (m,1H), 8.30 (s,1H, CH=N).

EXAMPLE 12

[5-(2-Amino-6-oxo-1,6-dihydro-purin-9-ylmethyl)-tetrahydro-furan-2-yl]-phosphonic Acid Diethyl Ester

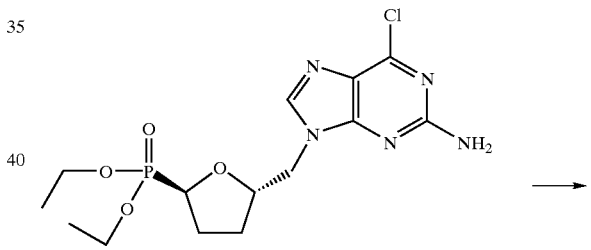

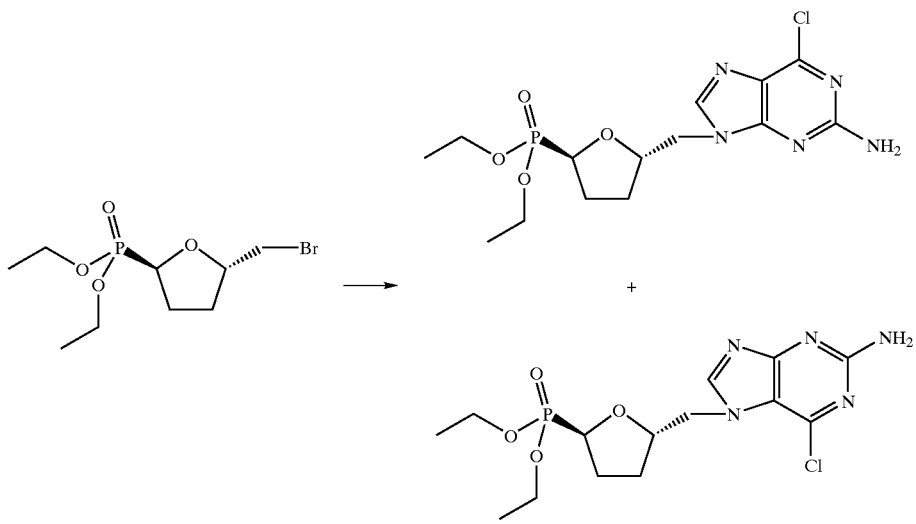

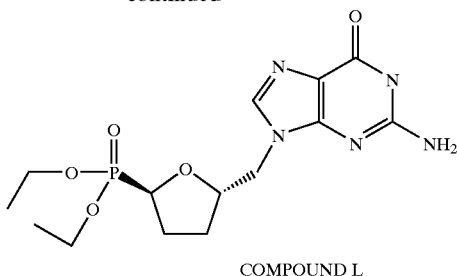

COMPOUND L

Procedure

To [5-(2-Amino-6-chloro-purin-9-ylmethyl)-tetrahydro-furan-2-yl]-phosphonic acid diethyl ester (100 mg, 0.25 mmol) in water (7 mL) and THF (5 mL) was added trimethylamine (1.6 mL, 6.4 mmol). The reaction mixture was stirred at RT under nitrogen overnight. Conversion to guanine was confirmed by UV spectroscopy. The THF was removed in vacuo and the reaction mixture lyophilized. The sample was chromatographed eluting with 10% methanol/dichloromethane to give [5-(2-Amino-6-oxo-1,6-dihydro-purin-9-ylmethyl)-tetrahydro-furan-2-yl]-phosphonic acid diethyl ester as a white powder (40 mg, 42%).

$^1$H nmr (400 MHz, DMSO) δ: 1.20 (m, 6H, 2Me), 1.62 (m, 1H), 2.02 (m, 3H), 4.00 (m, 6H, 2CH$_2$), 4.27 (m, 2H), 6.46 (s, 2H, NH$_2$), 7.62 (s, 1H, CH=N), 10.56 (s, 1H, NH).

EXAMPLE 13

Ammonium; 5-(2-Amino-6-oxo-1,6-dihydro-purin-7-ylmethyl)-tetrahydro-furan-2-phosphonate

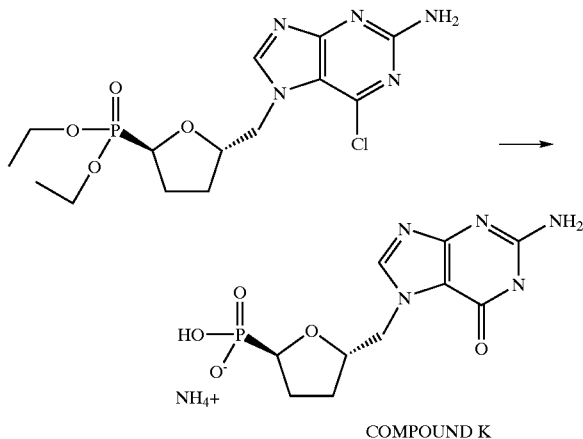

COMPOUND K

Procedure

To [5-(2-Amino-6-chloro-purin-7-ylmethyl)-tetrahydro-furan-2-yl]-phosphonic acid diethyl ester (78 mg, 0.20 mmol) was added bromotrimethylsilane (0.52 mL, 3.93 mmol) and stirred at RT under nitrogen overnight. The reaction mixture was concentrated to give a bright yellow solid which was dissolved in 1N HCl/water (0.4 mL/2 mL) and refluxed overnight. Conversion to guanine was confirmed by UV spectroscopy. The reaction mixture was extracted 2x with dichloromethane and 1x with pentane. The aqueous layer was lyophilized and dissolved in a small amount of water and passed through a short column of charcoal eluting with 1% ammonium hydroxide/water. The fractions were combined and lyophilized to give Ammonium; 5-(2-amino-6-oxo-1,6-dihydro-purin-7-ylmethyl)-tetrahydro-furan-2-phosphonate as a pale gray fluffy solid (30 mg, 45%).

$^1$H nmr (300 MHz, D$_2$O) δ: 1.52 (m, 1H), 1.98 (m, 3H), 3.88 (m, 1H), 4.11 (m, 3H), 7.86 (s, 1H, CH=N).

EXAMPLE 14

Ammonium; [5-(2-Amino-6-oxo-1,6-dihydro-purin-9-ylmethyl)-tetrahydro-furan-2-yl]-phosphonic Acid Monoethyl Ester

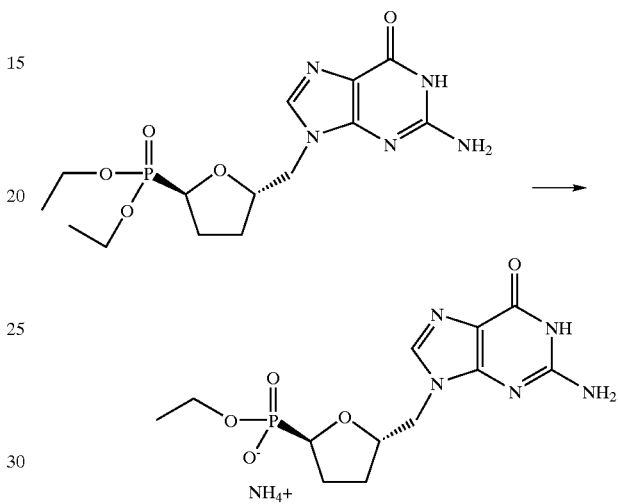

Procedure:

[5-(2-Amino-6-oxo-1,6-dihydro-purin-9-ylmethyl)tetrahydro-furan-2-yl]-phosphonic acid diethyl ester in 1M NaOH (0.3 mL) was heated at 100° C. in a screwcap vial overnight. The reaction mixture was diluted with water and passed through a small cake of acidic resin, and then washed with 0.5% ammonium hydroxide/water. The combined fractions were washed 2x with dichloromethane and 1x with pentane, and lyophilized to give Ammonium; [5-(2-Amino-6-oxo-1,6-dihydro-purin-9-ylmethyl)-tetrahydro-furan-2-yl]-phosphonic acid monoethyl ester as a white powder (3 mg, 40%).

$^1$H nmr (400 MHz, D$_2$O) δ: 1.09 (m, 3H, Me), 1.62 (m, 1H), 1.96 (m, 1H), 2.12 (m, 2H), 3.80 (m, 2H, CH$_2$), 4.00 (m, 1H), 4.17 (m, 1H), 4.25 (m, 1H), 4.37 (m, 1H), 8.67 (bs, 1H, CH=N).

EXAMPLE 15

Ammonium; 5-(2-Amino-6-cyclopropylamino-purin-9-ylmethyl)-tetrahydro-furan-2-phosphonate

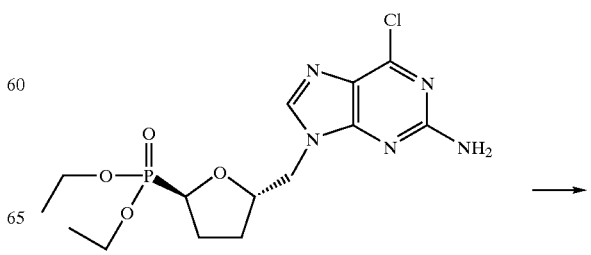

59
-continued

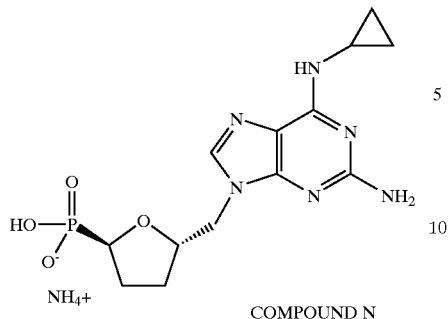

COMPOUND N

Procedure

To [5-(2-Amino-6-chloro-purin-9-ylmethyl)-tetrahydro-furan-2-yl]-phosphonic acid diethyl ester (85 mg, 0.21 mmol) in ethanol (2 mL) was added cyclopropylamine (0.18 mL, 2.18 mmol) and heated at 80° C. in a sealed glass tube overnight. The solvent was removed in vacuo and the residue chromatographed eluting with 10% methanol/dichloromethane. The purified material was placed in dichloromethane and to this was added bromotrimethylsilane (0.5 mL, 2.81 mmol) and stirred at RT overnight. The reaction mixture was concentrated and pushed through a short column of charcoal eluting with 0.5% ammonium hydroxide/water. The fractions were lyophilized to give Ammonium; 5-(2-amino-6-cyclopropylamino-purin-9-ylmethyl)-tetrahydro-furan-2-phosphonate as a pale gray powder (50 mg, 62%).

[1]H nmr (400 MHz, $D_2O$) δ: 0.72 (s, 2H ($CH_2CH_2$)),

EXAMPLE 16

[5-(2-Amino-8-chloro-6-oxo-1,6-dihydro-purin-9-ylmethyl)-tetrahydro-furan-2-yl]-phosphonic Acid Diphenyl Ester

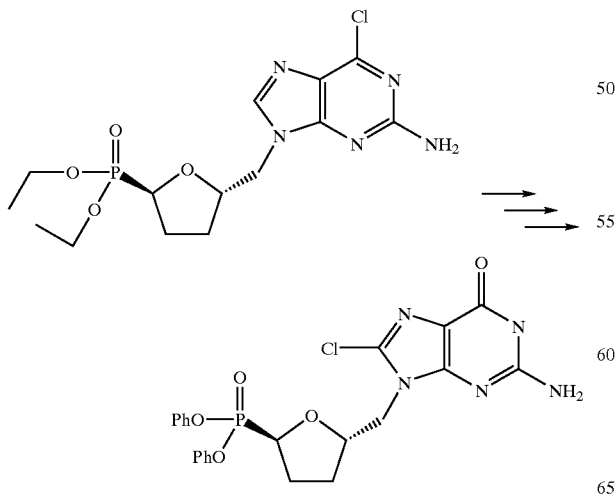

+

60
-continued

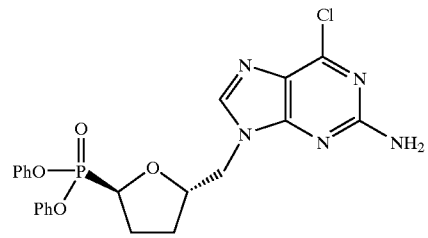

Procedure

To [5-(2-Amino-6-chloro-purin-9-yl methyl)-tetrahydrofuran-2-yl]-phosphonic acid diethyl ester (140 mg, 0.37 mmol) in dichloromethane (5 mL) was added bromotrimethylsilane (0.134 mL, 1.01 mmol) and stirred at RT for 4 hrs. The reaction mixture was concentrated, co-evaporated 2x with methanol, and dried well under vacuum. To the sugar was added thionyl chloride (8 mL), refluxed for 2 hours and then heated at 60° C. overnight. The reaction mixture was concentrated and dried under vacuum. It was then dissolved in dichloromethane (5 mL) and to it added phenyl alcohol (74 mg, 0.78 mmol), dry triethylamine (0.118 mL, 0.84 mmol) and N-methylimidazole (0.108 mL, 1.35 mmol). The reaction mixture was stirred at RT overnight. The reaction mixture was then concentrated, dissolved in chloroform and washed with saturated sodium bicarbonate, water and brine. The organic layer was dried over sodium sulfate, concentrated and chromatographed. Elution with 2% methanol/dichloromethane gave [5-(2-Amino-6-chloro-purin-9-ylmethyl)-tetrahyd ro-furan-2-yl]-phosphonic acid diphenyl ester (5 mg, 3%) and elution with 15–20% methanol/dichloromethane gave [5-(2-Amino-8-chloro-6-oxo-1,6-dihydro-purin-9-ylmethyl)-tetrahydro-furan-2-yl]-phosphonic acid diphenyl ester as a white solid (20 mg, 11%).

[1]H nmr (400 MHz, DMSO) δ: 1.83 (m, 1H), 2.20 (m, 2H), 2.41 (m, 1H), 4.08 (m, 2H), 4.43 (m, 1H), 4.67 (m, 1H), 6.61 (s, 2H, NH2), 7.04 (d, J=8.0 Hz, 2H (Ph)), 7.13 (d, J=8.2 Hz, 2H (Ph)), 7.21 (m, 2H (Ph)), 7.38 (m, 4H), 10.73 (s, 1H, NH);

[31]P nmr (400 MHz, DMSO) δ: 17.7; 13Cnmr (400 MHz, DMSO) δ: 27.2, 29.5, 46.6, 74.0, 78.9, 115.6 (CCl), 121.1 (3C), 125.9, 126.0,130.4,130.6, 132.7, 152.8, 154.6,156.3; ms (m/z): 502.1 (M+1).

EXAMPLE 17

Benzoic Acid 5-(Diisopropoxy-phosphoryl)-3-methoxy-tetrahydro-furan-2-ylmethyl Ester

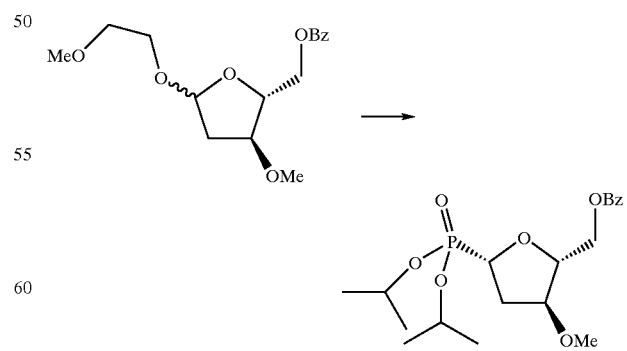

Procedure

To Benzoic acid 3-methoxy-5-(2-methoxy-ethoxy)-tetrahydrofuran-2-yl methyl ester (1.67 g, 5.36 mmol) in dichloromethane (50 mL) and triisopropylphosphite (1.45 mL, 5.89 mmol) was added titaniumtetrachloride (1 M in toluene, 5.9 mL) dropwise at 0° C. The reaction was stirred at 0° C. for 0.75 h and then RT for 3 h. The reaction was quenched with 1N HCl and extracted with dichoromethane, the organic layers dried, filtered through celite, concentrated and chromatographed. Elution with 50% ethylacetate/hexanes gave Benzoic acid 5-(diisopropoxy-phosphoryl)-3-methoxy-tetrahydro-furan-2-ylmethyl ester as a colorless syrup (970 mg, 45%).

$^1$H nmr (400 MHz, CDCl$_3$) δ: 1.34 (m, 12H (4Me)), 2.24 (m, 1H), 2.60 (m, 1H), 3.38 (s, 3H, Me), 3.97 (m, 1H), 4.27 (m, 2H), 4.47 (m, 2H), 4.80 (m, 2H (OCH)), 7.45 (m, 2H, Bz), 7.58 (m, 1H, Bz), 8.03 (m, 2H, Bz).

EXAMPLE 18

(5-Hydroxymethyl4-methoxy-tetrahydro-furan-2-yl)-phosphonic Acid Diisopropyl Ester

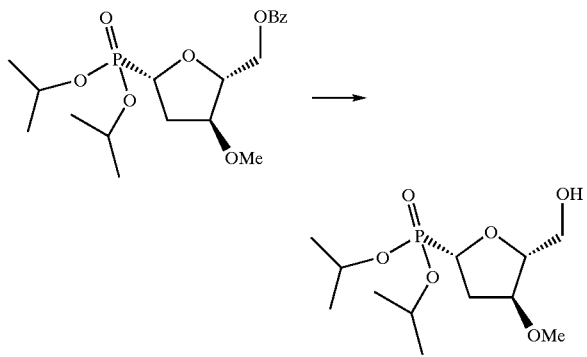

Procedure

To a solution of Benzoic acid 5-(diisopropoxy-phosphoryl)-3-methoxy-tetrahydro-furan-2-ylmethyl ester (266 mg, 0.66 mmol) in methanol (3 mL) was added potassium carbonate (45 mg, 0.33 mmol) and stirred for 5 hours at RT. Dowex acidic resin was added until neutral pH was attained, the reaction mixture filtered and concentrated to give (5-Hydroxymethyl-4-methoxy-tetrahydro-furan-2-yl)-phosphonic acid diisopropyl ester (168 mg, 85%).

$^1$H nmr (400 MHz, CDCl$_3$) δ: 1.38 (m, 12H (4Me)), 2.13 (m, 1H), 2.52 (m, 1H), 3.39 (s, 3H, Me), 3.63 (m, 1H), 3.82 (m, 1H), 3.97 (m, 2H), 4.20 (m, 1H), 4.79 (m, 2H (OCH)), 7.29 (s, 1H, CH=N).

EXAMPLE 19

[5-(2-Amino-6-chloro-purin-9-ylmethyl)4methoxy-tetrahydro-furan-2-yl]-phosphonic Acid Diisopropyl Ester

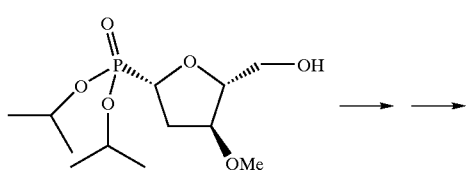

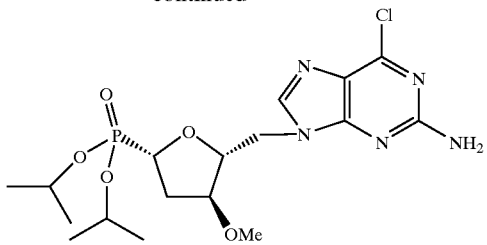

Procedure

To a solution of (5-Hydroxymethyl-4-methoxy-tetrahydro-furan-2-yl)-phosphonic acid diisopropyl ester (168 mg, 0.56 mmol) in dichloromethane (5 mL) and dry triethylamine (0.11 mL, 0.84 mmol) was added mesyl chloride (0.057 mL, 0.73 mmol) dropwise at 0° C. and left to stir for one hour. The reaction mixture was poured into saturated sodium bicarbonate and extracted with dichloromethane. The organic layers were combined, dried over sodium sulfate, and concentrated to give the mesylate as a colorless syrup (211 mg). The mesylate (211 mg, 0.56 mmol) was dissolved in DMF (7 mL) and transferred via cannula to a solution of cesium carbonate (372mg, 1.4mmol) and 2-amino-6-chloropurine (239 mg, 1.4 mmol) in DMF (7 mL) which had been previously heated at 100° C. for 0.5 hours. The reaction mixture was stirred at 100° C. for 4 hrs. The reaction mixture was then concentrated and chromatographed, eluting with 4% methanol/dichloromethane to give [5-(2-Amino-6-chloro-purin-9-ylmethyl)-4-methoxy-tetrahydro-furan-2-yl]-phosphonic acid diisopropyl ester (90 mg, 36%) as a white foam.

$^1$H nmr (400 MHz, CD$_3$OD) δ: 1.27 (m, 12H (3Me)), 2.09 (m, 1H), 2.63 (m, 1H), 3.37 (s, 3H, Me), 3.83 (m, 1H), 4.30 (m, 4H), 4.65 (m, 2H (OCH)), 8.04 (s,1H (CH=N)).

EXAMPLE 20

Ammonium; 5-(2-Amino-6-oxo-1,6-dihydro-purin-9-ylmethyl)-4-methoxy-tetrahydro-furan-2-phosphonate

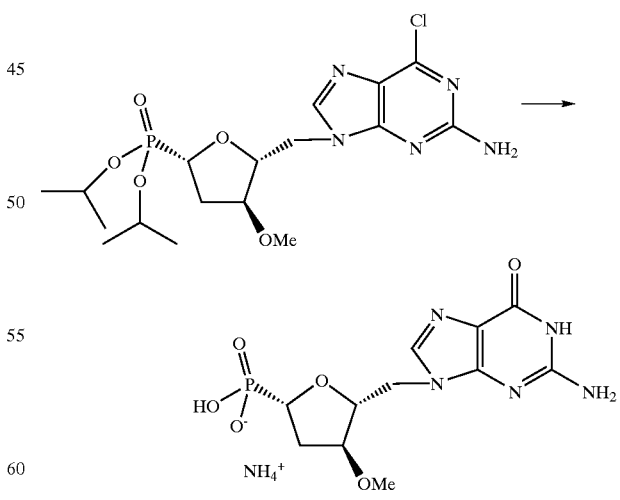

COMPOUND J

Procedure

To [5-(2-Amino-6-chloro-purin-9-ylmethyl)-4-methoxy-tetrahydro-furan-2-yl]-phosphonic acid diisopropyl ester (90 mg, 0.20 mmol) was added bromotrimethylsilane (0.53 mL, 4.01 mmol) and stirred at RT under nitrogen overnight. The reaction mixture was concentrated to give a bright yellow solid which was dissolved in 10% HCl/water (0.2 mL/3.4 mL) and refluxed overnight. Conversion to guanine was confirmed by UV spectroscopy. The reaction mixture was extracted 2× with dichloromethane and 1× with pentane. The aqueous layer was lyophilized and dissolved in a small amount of water and passed through a short column of charcoal, eluting with 0.5% ammonium hydroxide/water. The fractions were combined and lyophilized to give Ammonium; 5-(2-amino-6-oxo-1,6-dihydro-purin-9-ylmethyl)-4-methoxy-tetrahydro-furan-2-phosphonate as a white fluffy solid (69 mg, 95%).

$^1$H nmr (400 MHz, D2O) δ: 1.85 (m, 1H), 2.45 (m, 1H), 3.20 (s, 3H (Me)), 3.75 (q, J=6.2, 7.2 Hz, 1H), 3.89 (m, 1H), 4.10 (m, 1H), 4.17 (m, 2H), 7.79 (s, 1H, CH=N;

$^{31}$P nmr (400 MHz, D2O) δ: 16.3.

EXAMPLE 21

Antiviral Activity 21.1) Anti-HIV Activity.

Laboratory strains of HIV-1, were used to infect established cell lines by using a specific multiplicity of infection (MOI) of the virus for 1 hour at 37° C. prior to washing the cells and re-suspension in medium containing increasing concentrations of drug (or test compound). At 4 to 6 days post-infection, drug-treated and control wells are analyzed for an HIV-1 induced cytopathic effect and/or for the presence of viral reverse transcriptase (RT) or viral p24 antigen in the culture medium (Buckheit and Swanstrom (1991) AIDS Res. Human Retroviruses 7:295–302; Ojwang, et al (1994) J. Acquired Immune Deficiency Syndrome 7:560–570; Ojwang, J. O., et al (1995) Antimicrobial Agents and Chemotherapy. 39:2426–2435 and Rando et al (1995) J. Biol. Chem. 270:1754–1760).

TABLE 1

Inhibition of HIV-1 replication.

| Compound | EC$_{50}$ (µg/ml) | CCTD$_{50}$ (µg/ml) |
|---|---|---|
| (5R)-(2-amino-6-hydroxy-purin-9-ylmethyl)-(4R)-azido-tetrahydro-furan-(2S)-phosphonate Compound (10) | 5 | >10 |
| (5R)-(2-amino-6-hydroxy-purin-9-ylmethyl)-(4R)-fluoro-tetrahydro-furan-(2S)-phosphonate Compound (23) | >10 | >10 |
| (5R)-(2-amino-6-hydroxy-purin-9-ylmethyl)-(4S)-fluoro-tetrahydro-furan-(2S)-phosphonate; Compound (16) | 0.46 | >10 |

21.2) Anti-HBV Activity

The 2.2.15 cell line derived from HepG2 cells transfected with episomal HBV DNA (Sells et al (1987) Proc. Natl. Acad. Sci. USA 84:1005–1009 and (1988) J. Virol. 62:2836–2844) was used. The assay was performed basically as described by Ojwang et al. (1995) Antimicrobial Agents and Chemotherapy 39:2570–2573 ). The 2.2.15 cells are seeded (10$^5$ cells per well) in 300 ul of minimal essential medium supplemented with 10% fetal bovine serum, using 24-well plates pre-coated with 150 ul of 0.1 mg of collagen (rat tail) type I per ml reconstituted in 0.02 M acetic acid. The collagen treatment helped the cells 10 disperse evenly over the culture plate. Once the cells reach confluency (approximately 1 day), the culture medium is replaced every 2 days with medium containing various concentrations of the indicated test compound. In this experiment, the nucleosides 2',3'-dideoxy-3'-thiacytidine (3TC) or 2',3'-dideoxycytidine (ddC) are used as positive controls (Ojwang et al. (1995)). Twelve days postadministration of the test compounds, cells are harvested and DNA is prepared as described by Fennewald et al. ( (1995) Antiviral Res. 26:37–54.). At the same time, the culture medium is saved and analyzed for the presence of extracellular viral nucleic acids.

The integrated and episomal HBV DNAs are easily separated by using agarose gel electrophoresis which allows for the differential quantification of the two species of HBV DNA. For DNA blot hybridization analysis, 5 to 10 ug of HindIII-cleaved total intracellular DNA is used because this enzyme does not cleave the episomal HBV genome (Sambrook, J et al (1989) Molecular cloning: a laboratory manual. 2$^{nd}$ ed. Cold Spring Harbor Laboratory Press. Cold Spring Harbor, N.Y.). As a molecular probe, a subgenomic fragment of the HBV DNA is cloned into the pCRII TA cloning vector (Invitrogen) plasmid between the two EcoR1 sites. The subgenomic HBV DNA fragment is obtained by using the PCR technique to amplify a portion of the HBV genome (nucleotide positions 2134 to 143). Total DNA isolated from 2.2.15 cells is used as the PCR template with primer sets corresponding to nucleotide positions 2134 to 2151 (forward) and 143 to 126 (reverse). The resulting fragment is then inserted into pCRII TA. /The 1,200 -bp fragment of HBV DNA is cleaved out of the recombinant plasmid by using EcoR1, purified, and then radiolabeled with [a-$^{32}$P]dATP (New England Nuclear) and the Rediprime random primer labeling kit (Amersham) to a specific activity of 2×10$^9$ cpm/ug (Sambrook et al. (1989)). Pre-hybridization, 5 hybridization, and washing are carried out according to the Rapid-hyb kit (Amersham) instructions. Autoradiography of the filters is performed at −80C with X-ray film. In addition, the filters are also exposed to a photoimaging plate and quantitated, using a Fujix Bioimaging Analyzer System BAS 1000 (or similar) instrument.

TABLE 2

Inhibition of HBV replication

| Compound | EC$_{50}$ (µg/ml) | CC$_{50}$ (µg/ml) |
|---|---|---|
| (5R)-(2-amino-6-hydroxy-purin-9-ylmethyl)-(4R)-azido-tetrahydro-furan-(2S)-phosphonate Compound (10) | 0.295 | >300 |
| (5R)-(2-amino-6-hydroxy-purin-9-ylmethyl)-(4R)-fluoro-tetrahydro-furan-(2S)-phosphonate; Compound (16) | 11 | >300 |
| (5R)-(2-amino-6-hydroxy-purin-9-ylmethyl)-(4S)-fluoro-tetrahydro-furan-(2S)-phosphonate; Compound (23) | >30 | >300 |

We claim:

1. A nucleotide analogue according to formula (I):

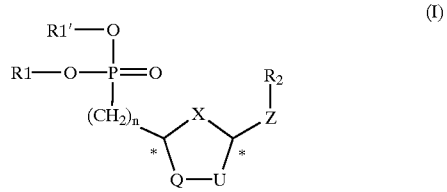

or a pharmaceutically acceptable salt, a pharmaceutically acceptable ester, or a pharmaceutically acceptable salt of an ester wherein:

n is 0;
X is O;
Q is $CH_2$;
U is $C=CH_2$ or $CH(R_a)$;
$R_a$ is OH, CN, halogen, $N_3$, or $NH_2$;
Z is $(CH2)_m$ wherein m is 1;
R1 and R1' are each independently selected from H, $C_{1-6}$ alkyl, phosphate or diphosphate; and
$R_2$ is

A)

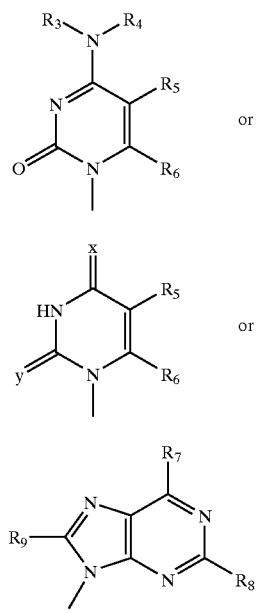

F)

M)

wherein
x is oxygen or sulfur;
y is oxygen or sulfur;
$R_3$ and $R_4$ are each independently selected from hydrogen, hydroxyl, amino, $C_{1-6}$ alkyl, $C_{2-6}$ alkenyl, $C_{2-6}$ alkynyl, $C_{1-10}$ acyl, or $C_{6-12}$ aryl;
$R_5$ and $R_6$ are each independently selected from hydrogen, F, Cl, Br, I, hydroxyl, methyl or amino;
$R_7$ is H, F, Cl, I, Br, hydroxyl, amino or the formulas

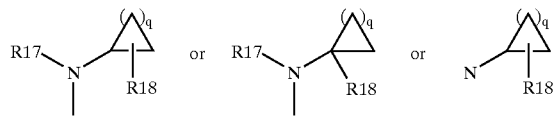

wherein:
q is an integer selected from 1 to 4;
R18 is selected from H, COOH, $C(O)NH_2$, OH, SH, $NH_2$, $NO_2$, or $C_{1-6}$ alkyl;
R17 is H or a $C_{1-6}$ alkyl; and
$R_8$ and $R_9$ are each independently chosen from hydrogen, hydroxyl, amino, substituted amino, halogen, azido or methyl;
provided that when $R_2$ is adenine $R_a$, if present, is CN, halogen, $N_3$, or $NH_2$.

2. A nucleotide analogue according to claim 1, wherein $Z(R_2)$ and $(CH_2)_nP(O)O_2R1R1'$ are in the cis configuration.

3. A nucleotide analogue according to claim 1, wherein $R_7$ is Cl, hydroxyl, $NH_2$ or the formula

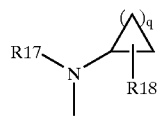

wherein
q is an integer selected from 1 or 2;
R18 is selected from H or COOH;
$R_8$, $R_9$, $R_{10}$ oand R17 are hydrogen; and
$R_5$ is F, I, Cl, or $CH_3$.

4. A nucleotide analogue according to claim 1, wherein $R_2$ is chosen from cytosine, adenine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine.

5. A cis nucleotide analogue according to formula (I):

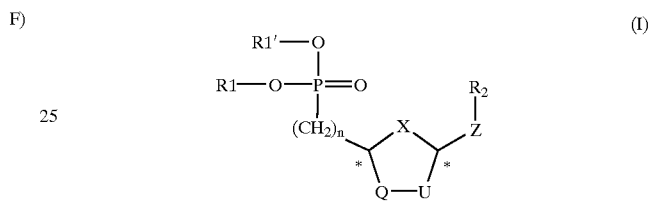

(I)

or a pharmaceutically acceptable salt, a pharmaceutically acceptable ester, or a pharmaceutically acceptable salt of an ester wherein:
n is 0 or 1;
X is O;
R1 and R1' are each independently selected from H, phosphate or diphosphate;
Q is $CH_2$;
U is $C=CH_2$;
Z is $(CH_2)_m$ wherein m is 1; and
$R_2$ is chosen from cytosine, adenine, guanine, uracil, thymine, 2-amino-6-chloropurine, 6-chloropurine, 2,6-diaminopurine, 2-amino-6-cyclopropylamino-purine; 2-amino-6-[1 -carboxylic acid-cyclopropylamino]-purine, 2-amino-6-cyclobutylamino-purine, 2-amino-6-azetidino-purine, 2-amino-6-cyclopentylamino-purine or 5-fluoropyrimidine.

6. A nucleotide analogue according to claim 1, wherein R1 and R1' are each independently selected from H, phosphate or diphosphate; Q is $CH_2$; U is $CH(R_a)$; $R_a$ is OH, CN, F, Cl, Br, I, $N_3$ or $NH_2$; and $R_2$ is chosen from cytosine, adenine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine, provided that when $R_2$ is adenine, $R_a$ is CN, F, Cl, Br, I, $N_3$ or $NH_2$.

7. A nucleotide analogue according to claim 6, wherein $R_a$ is in the α configuration with respect to Z.

8. A nucleotide analogue according to claim 6, wherein $R_a$ is in the β configuration with respect to Z.

9. A nucleotide analogue according to claim 6, wherein $R_a$ is in the R configuration.

10. A nucleotide analogue according to claim 6, wherein $R_a$ is in the S configuration.

11. A nucleotide analogue according to claim 6, wherein $ZR_2$ is in the R configuration.

12. A nucleotide analogue according to claim 6, wherein $ZR_2$ is in the S configuration.

13. A nucleotide analogue according to claim 6, wherein the configuration of the compound is cis.

14. A cis nucleotide analogue according to formula (I):

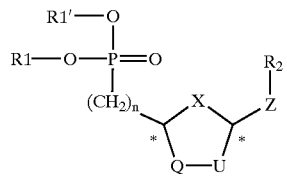

(I)

or a pharmaceutically acceptable salt, a pharmaceutically acceptable ester, or a pharmaceutically acceptable salt of an ester wherein:

n is 0 or 1;

X is O;

R1 and R1' are each independently selected from H, phosphate or diphosphate;

U and Q are both CH and are linked by a double bond;

$R_a$ is hydrogen, OH, CN, halogen, $N_3$, $NH_2$, SH, $C_{1-6}$ alkyl, $C_{1-6}$ alkoxy, $C_{2-6}$ alkenyl, $C_{2-6}$ alkynyl, $C(O)R_b$, $NHR_b$, or $SR_b$;

$R_b$ is hydrogen, OH, CN, halogen, $N_3$, $NH_2$, SH, $C_{1-6}$ alkyl or $C_{1-6}$ acyl, or $C(O)OR_c$;

$R_c$ is $C_{1-6}$ alkyl or $C_{1-6}$ acyl;

Z is $(CH_2)_m$ wherein m is 1; and $R_2$ is chosen from cytosine, adenine, guanine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine.

15. A nucleotide analogue chosen from:

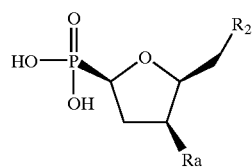

(i)

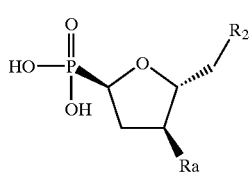

(ii)

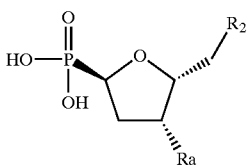

(iii)

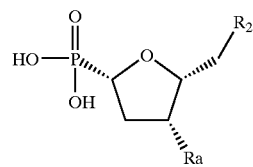

(iv)

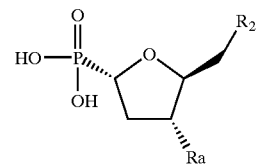

(v)

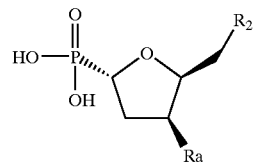

(vi)

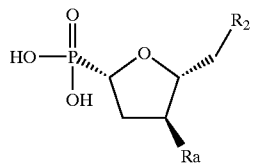

(vii)

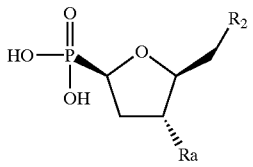

(viii)

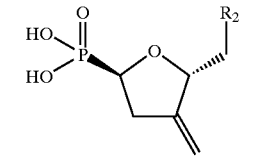

(ix)

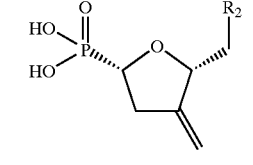

(x)

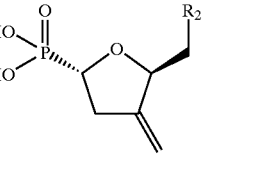

(xi)

or

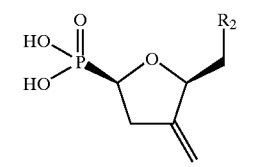

(xii)

wherein:

$R_2$ is cytosine, adenine, uracil, thymine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, 2-amino-6-cyclopentylamino-purine or 5-fluoropyrimidine and Ra is OH, F, Cl, Br, I or $N_3$.

16. A nucleotide analogues according to claim 15, wherein the compound is selected from formulas (i), (iv), (vii), (viii), (x) and (xii).

17. A pharmaceutical formulation comprising a pharmaceutically effective amount of a compound according to claim 1 and a pharmaceutically acceptable carrier.

18. A method of treating a mammal suffering from an HIV or HBV infection comprising administering to said mammal a therapeutically effective amount of a compound according to claim 1.

19. A method of treating an HIV infection in a mammal comprising administering to said mammal a pharmaceutical formulation according to claim 17.

20. A method according to claim 19, wherein said mammal is a human.

21. A method according to claim 19, wherein said administration is carried out at a dose of 0.1 to 750 mg/kg of bodyweight per day.

22. A method according to claim 19, wherein said compound of formula (I) is selected from
   (5R)-(2-amino-6-hydroxy-purin-9-ylmethyl)-(4R)-azido-tetrahydro-furan-(2S)-phosphonate and;
   (5R)-(2-amino-6-hydroxy-purin-9-ylmethyl)-(4S)-fluoro-tetrahydro-furan-(2S)-phosphonate.

23. A method of treating a hepatitis B virus infection in a mammal comprising administering to said mammal a pharmaceutical formulation according to claim 17.

24. A method according to claim 23, wherein said mammal is a human.

25. A method according to claim 23, wherein said compound of formula (I) is selected from
   (5R)-(2-amino-6-hydroxy-purin-9-ylmethyl)-(4R)-azido-tetrahydro-furan-(2S)-phosphonate and;
   (5R)-(2-amino-6-hydroxy-purin-9-ylmethyl)-(4R)-fluoro-tetrahydro-furan-(2S)-phosphonate.

26. A method according to claim 23, wherein said administration is carried out at a dose of 0.1 to 750 mg/kg of bodyweight per day.

27. A method according to claim 19, wherein said compound of formula (I) is selected from
   (5R)-(2-amino-6-hydroxy-purin-9-ylmethyl)-(4R)-azido-tetrahydro-furan-(2S)-phosphonate;
   (5R)-(2-amino-6-hydroxy-purin-9-ylmethyl)-(4S)-fluoro-tetrahydro-furan-(2S)-phosphonate and;
   (5R)-(2-amino-6-hydroxy-purin-9-ylmethyl)-(4R)-fluoro-tetrahydro-furan-(2S)-phosphonate.

28. A method according to claim 18, wherein
   $Z(R_2)$ and $P(O)O_2R1R1'$ are in the cis configuration;
   $R_a$ is OH, CN, halogen, $N_3$;
   R1 and R1' are independently selected from the group H, phosphate or diphosphate.

29. A method according to claim 28, wherein $R_2$ is adenine, 2-amino-6-chloropurine, 6-chloropurine, 2,6-diaminopurine, 2-amino-6-cyclopropylamino-purine; 2-amino-6-[1-carboxylic acid-cyclopropylamino]-purine, 2-amino-6-cyclobutylamino-purine, 2-amino-6-azetidino-purine, or 2-amino-6-cyclopentylamino-purine.

30. A method according to claim 29, wherein $R_a$ is in the R configuration and is OH, $N_3$, fluoro, chloro, bromo or iodo.

31. A method according to claim 29, wherein $R_a$ is in the S configuration and is OH, $N_3$, fluoro, chloro, bromo or iodo.

32. A method according to claim 28, wherein said mammal is a human.

33. A method according to claim 28, wherein said compound is administered at a dose of 0.1 to 750 mg/kg of bodyweight per day.

34. A method according to claim 28, wherein said compound of formula (I) is:
   (5R)-(2-amino-6-hydroxy-purin-9-ylmethyl)-(4R)-azido-tetrahydro-furan-(2S)-phosphonate or a pharmaceutically acceptable salt thereof;
   (5R)-(2-amino-6-hydroxy-purin-9-ylmethyl)-(4R)-fluoro-tetrahydro-furan-(2S)-phosphonate or a pharmaceutically acceptable salt thereof; or
   (5R)-(2-amino-6-hydroxy-purin-9-ylmethyl)-(4S)-fluoro-tetrahydro-furan-(2S)-phosphonate or a pharmaceutically acceptable salt thereof; wherein said compound is present in the form of a racemic mixture or single enantiomer.

35. A nucleotide analogue selected from the group:
   (5R)-(2-amino-6-hydroxy-purin-9-ylmethyl)-(4S)-azido-tetrahydro-furan-(2S)-phosphonate;
   (5R)-(2-amino-6-hydroxy-purin-9-yl methyl)-(4R)-azido-tetrahydro-furan-(2S)-phosphonate;
   (5R)-(2-amino-6-hydroxy-purin-9-ylmethyl)-(4S)-azido-tetrahydro-furan-(2R)-phosphonate;
   (5R)-(2-amino-6-hydroxy-purin-9-ylmethyl)-(4R)-azido-tetrahydro-furan-(2R)-phosphonate;
   (5R)-(2-amino-6-hydroxy-purin-9-ylmethyl)-(4R)-fluoro-tetrahydro-furan-(2S)-phosphonate;
   (5R)-(2-amino-6-hydroxy-purin-9-ylmethyl)-(4R)-fluoro-tetrahydro-furan-(2R)-phosphonate;
   (5R)-(2-amino-6-hydroxy-purin-9-ylmethyl)-(4S)-fluoro-tetrahydro-furan-(2S)-phosphonate;
   (5R)-(2-amino-6-hydroxy-purin-9-ylmethyl)-(4S)-fluoro-tetrahydro-furan(2R)-phosphonate;
   (5R)-(2-amino-6-hydroxy-purin-9-ylmethyl)-(4S)-hydroxy-tetrahydro-furan-(2S)-phosphonate;
   (5R)-(2-amino-6-hydroxy-purin-9-ylmethyl)-(4R)-hydroxy-tetrahydro-furan-(2R)-phosphonate;
   (5R)-(2-amino-6-hydroxy-purin-9-ylmethyl)-(4S)-hydroxy-tetrahydro-furan-(2R)-phosphonate;
   (5R)-(2-amino-6-hydroxy-purin-9-ylmethyl)-(4R)-hydroxy-tetrahydro-furan-(2S)-phosphonate;
   (5R)-(2-amino-6-hydroxy-purin-9-ylmethyl)-(4R)-iodo-tetrahydro-furan-(2S)-phosphonate;
   (5R)-(2-amino-6-hydroxy-purin-9-ylmethyl)-(4R)-iodo-tetrahydro-furan-(2R)-phosphonate;
   (5R)-(2-amino-6-hydroxy-purin-9-ylmethyl)-(4S)-iodo-tetrahydro-furan-(2S)-phosphonate;
   (5R)-(2-amino-6-hydroxy-purin-9-ylmethyl)-(4S)-iodo-tetrahydro-furan-(2R)-phosphonate;
   (5R)-(2-amino-6-hydroxy-purin-9-ylmethyl)-(4R)-chloro-tetrahydro-furan-(2S)-phosphonate;
   (5R)-(2-amino-6-hydroxy-purin-9-ylmethyl)-(4R)-chloro-tetrahydro-furan-(2R)-phosphonate;
   (5R)-(2-amino-6-hydroxy-purin-9-ylmethyl)-(4S)-chloro-tetrahydro-furan-(2S)-phosphonate;
   (5R)-(2-amino-6-hydroxy-purin-9-ylmethyl)-(4S)-chloro-tetrahydro-furan-(2R)-phosphonate;
   (5R)-(2amino-6-hydroxy-purin-9-ylmethyl)-(4R)-bromo-tetrahydro-furan-(2S)-phosphonate;
   (5R)-(2-amino-6-hydroxy-purin-9-ylmethyl)-(4R)-bromo-tetrahydro-furan-(2R)-phosphonate;
   (5R)-(2-amino-6-hydroxy-purin-9-ylmethyl)-(4S)-bromo-tetrahydro-furan-(2S)-phosphonate;

(5R)-(2-amino-6-hydroxy-purin-9-ylmethyl)-(4S)-
bromo-tetrahydro-furan-(2R)-phosphonate; and
pharmaceutically acceptable salts thereof.

36. A nucleotide analogue selected from the group:
[(5R)-2(2-amino-6-hydroxy-purin-9-ylmethyl)-4-
methylene-tetrahydro-furan(2R)-yl]-phosphonic acid;
[(5S)-2(2-amino-6-hydroxy-purin-9-ylmethyl)-4-
methylene-tetrahydro-furan(2S)-yl]-phosphonic acid;
[(5R) -2(2-amino-6-hydroxy-purin-9-ylmethyl)-4-
methylene-tetrahydro-furan(2S) -yl]-phosphonic acid;
and
[(5S)-2(2-amino-6-hydroxy-purin-9-ylmethyl)-4-
methylene-tetrahydro-furan(2R)-yl]-phosphonic acid;
and
pharmaceutically acceptable salts thereof.

37. A nucleotide analogue selected from the group:
(5R)-(2-amino-6-cyclopropylamino-purin-9-ylmethyl)-
(4S)-azido-tetrahydro-furan-(2S)-phosphonate;
(5R)-(2-amino-6-cyclopropylamino-purin-9-ylmethyl)-
(4R)-azido-tetrahydro-furan-(2S)-phosphonate;
(5R)-(2-amino-6-cyclopropylamino-purin-9-ylmethyl)-
(4S)-azido-tetrahydro-furan-(2R)-phosphonate;
(5R)-(2-amino-6-cyclopropylamino-purin-9-ylmethyl)-
(4R)-azido-tetrahydro-furan-(2R)-phosphonate;
(5R)-(2-amino-6-cyclopropylamino-purin-9-ylmethyl)-
(4R)-fluoro-tetrahydro-furan-(2S)-phosphonate;
(5R)-(2-amino-6-cyclopropylamino-purin-9-ylmethyl)-
(4R)-fluoro-tetrahydro-furan-(2R)-phosphonate;
(5R)-(2-amino-6-cyclopropylamino-purin-9-ylmethyl)-
(4S)-fluoro-tetrahydro-furan-(2S)-phosphonate;
(5R)-(2-amino-6-cyclopropylamino-purin-9-ylmethyl)-
(4S)-fluoro-tetrahydro-furan-(2R)-phosphonate;
(5R)-(2-amino-6-cyclopropylamino-purin-9-ylmethyl)-
(4S)-hydroxy-tetrahydro-furan-(2S)-phosphonate;
(5R)-(2-amino-6-cyclopropylamino-purin-9-ylmethyl)-
(4R)-hydroxy-tetrahydro-furan-(2R)-phosphonate;
(5R)-(2-amino-6-cyclopropylamino-purin-9-ylmethyl)-
(4S)-hydroxy-tetrahydro-furan-(2R)-phosphonate;
(5R)-(2-amino-6-cyclopropylamino-purin-9-ylmethyl)-
(4R)-hydroxy-tetrahydro-furan-(2S)-phosphonate;
(5R)-(2-amino-6-cyclopropylamino-purin-9-ylmethyl)-
(4R)-iodo-tetrahydro-furan-(2S)-phosphonate;
(5R)-(2-amino-6-cyclopropylamino-purin-9-ylmethyl)-
(4R)-iodo-tetrahydro-furan-(2R)-phosphonate;
(5R)-(2-amino-6-cyclopropylamino-purin-9-ylmethyl)-
(4S)-iodo-tetrahydro-furan-(2S)-phosphonate;
(5R)-(2-amino-6-cyclopropylamino-purin-9-ylmethyl)-
(4S)-iodo-tetrahydro-furan-(2R)-phosphonate;
(5R)-(2-amino-6-cyclopropylamino-purin-9-ylmethyl)-
(4R)-chloro-tetrahydro-furan-(2S)-phosphonate;
(5R)-(2-amino-6-cyclopropylamino-purin-9-ylmethyl)-
(4R)-chloro-tetrahydro-furan-(2R)-phosphonate;
(5R)-(2-amino-6-cyclopropylamino-purin-9-ylmethyl)-
(4S)-chloro-tetrahydro-furan-(2S)-phosphonate;
(5R)-(2-amino-6-cyclopropylamino-purin-9-ylmethyl)-
(4S)-chloro-tetrahydro-furan-(2R)-phosphonate;
(5R)-(2-amino-6-cyclopropylamino-purin-9-ylmethyl)-
(4R)-bromo-tetrahydro-furan-(2S)-phosphonate;
(5R)-(2-amino-6-cyclopropylamino-purin-9-ylmethyl)-
(4R)-bromo-tetrahydro-furan-(2R)-phosphonate;
(5R)-(2-amino-6-cyclopropylamino-purin-9-ylmethyl)-
(4S)-bromo-tetrahydro-furan-(2S)-phosphonate;
(5R)-(2-amino-6-cyclopropylamino-purin-9-ylmethyl)-
(4S)-bromo-tetrahydro-furan-(2R)-phosphonate; and
pharmaceutically acceptable salts thereof.

38. A nucleotide analogue selected from the group:
[(5R)-2(2-amino-6-cyclopropylamino-purin-9-ylmethyl)-
4-methylene-tetrahydro-furan(2R)-yl]-phosphonic
acid;
[(5S)-2(2-amino-6-cyclopropylamino-purin-9-ylmethyl)-
4-methylene-tetrahydro-furan(2S)-yl]-phosphonic
acid;
[(5R)-2(2-amino-6-cyclopropylamino-purin-9-ylmethyl)-
4-methylene-tetrahydro-furan(2S)-yl]-phosphonic
acid;
[(5)-2(2-amino-6-cyclopropylamino-purin-9-ylmethyl)-
4-methylene-tetrahydro-furan(2R)-yl]-phosphonic
acid; and
pharmaceutically acceptable salts thereof.

39. A method according to claim 18, wherein said compound is selected from the group:
(5R)-(2-amino-6-hydroxy-purin-9-ylmethyl)-(4S)-azido-
tetrahydro-furan-(2S)-phosphonate;
(5R)-(2-amino-6-hydroxy-purin-9-ylmethyl)-(4R)-azido-
tetrahydro-furan-(2S)-phosphonate;
(5R)-(2-amino-6-hydroxy-purin-9-ylmethyl)-(4S)-azido-
tetrahydro-furan-(2R)-phosphonate;
(5R)-(2-amino-6-hydroxy-purin-9-ylmethyl)-(4R)-azido-
tetrahydro-furan-(2R)-,phosphonate;
(5R)-(2-amino-6-hydroxy-purin-9-ylmethyl)-(4R)-
fluoro-tetrahydro-furan-(2S)-phosphonate;
(5R)-(2-amino-6-hydroxy-purin-9-ylmethyl)-(4R)-
fluoro-tetrahydro-furan-(2R)-phosphonate;
(5R)-(2-amino-6-hydroxy-purin-9-ylmethyl)-(4S)-fluoro-
tetrahydro-furan-(2S)-phosphonate;
(5R)-(2-amino-6-hydroxy-purin-9-ylmethyl)-(4S)-fluoro-
tetrahydro-furan-(2R)-phosphonate;
(5R)-(2-amino-6-hydroxy-purin-9-ylmethyl)-(4S)-
hydroxy-tetrahydro-furan-(2S)-phosphonate;
(5R)-(2-amino-6-hydroxy-purin-9-ylmethyl)-(4R)-
hydroxy-tetrahydro-furan-(2R)-phosphonate;
(5R)-(2-amino-6-hydroxy-purin-9-ylmethyl)-(4S)-
hydroxy-tetrahydro-furan-(2R)-phosphonate;
(5R)-(2-amino-6-hydroxy-purin-9-ylmethyl)-(4R)-
hydroxy-tetrahydro-furan-(2S)-phosphonate;
(5R)-(2-amino-6-hydroxy-purin-9-ylmethyl)-(4R)-iodo-
tetrahydro-furan-(2S)-phosphonate;
(5R)-(2-amino-6-hydroxy-purin-9-ylmethyl)-(4R)-iodo-
tetrahydro-furan-(2R)-phosphonate;
(5R)-(2-amino-6-hydroxy-purin-9-ylmethyl)-(4S)-iodo-
tetrahydro-furan-(2S)-phosphonate;
(5R)-(2-amino-6-hydroxy-purin-9-ylmethyl)-(4S)-iodo-
tetrahydro-furan-(2R)-phosphonate;
(5R)-(2-amino-6-hydroxy-purin-9-ylmethyl)-(4R)-
chloro-tetrahydro-furan-(2S)-phosphonate;
(5R)-(2-amino-6-hydroxy-purin-9-ylmethyl)-(4R)-
chloro-tetrahydro-furan-(2R)-phosphonate;
(5R)(2-amino6-hydroxy-purin-9-ylmethyl)-(4S)-chloro-
tetrahydro-furan-(2S)-phosphonate;
(5R)-(2-amino-6-hydroxy-purin-9-ylmethyl)-(4S)-
chloro-tetrahydro-furan-(2R)-phosphonate;
(5R)-(2-amino-6-hydroxy-purin-9-ylmethyl)-(4R)-
bromo-tetrahydro-furan-(2S)-phosphonate;
(5R)-(2-amino-6-hydroxy-purin-9-ylmethyl)-(4R)-
bromo-tetrahydro-furan-(2R)-phosphonate;

(5R)-(2-amino-6-hydroxy-purin-9-ylmethyl)-(4S)-bromo-tetrahydro-furan-(2S)-phosphonate;

(5R)-(2-amino-6-hydroxy-purin-9-ylmethyl)-(4S)-bromo-tetrahydro-furan2R)-phosphonate: and pharmaceutically acceptable salts thereof.

40. A method according to claim 18, wherein said compound is selected from the group:

[(5R)-2(2-amino-6-hydroxy-purin-9-ylmethyl)-4-methylene-tetrahydro-furan(2R)-yl]-phosphonic acid;

[(5S)-2(2-amino-6-hydroxy-purin-9-ylmethyl)-4-methylenetetrahydro-furan(2S)-yl]-phosphonic acid;

[(5R)-2(2-amino-6-hydroxy-purin-9-ylmethyl)-4-methylene-tetrahydro-furan(2)-yl]-phosphonic acid;

[(5S)-2(2-amino-6-hydroxy-purin-9-ylmethyl)-4-methylene-tetrahydro-furan(2R)-yl]-phosphonic acid; and pharmaceutically acceptable salts thereof.

41. A method according to claim 18, wherein said compound is selected from the group:

(5R)-(2-amino-6-cyclopropylamino-purin-9-ylmethyl)-(4S)-azido-tetrahydro-furan-(2S)-phosphonate;

(5R)-(2-amino-6-cyclopropylamino-purin-9-ylmethyl)-(4R)-azido-tetrahydro-furan-(2S)-phosphonate;

(5R)-(2-amino-6-cyclopropylamino-purin-9-ylmethyl)-(4S)-azido-tetrahydro-furan-(2R)-phosphonate;

(5R)-(2-amino-6-cyclopropylamino-purin-9-ylmethyl)-(4R)-azido-tetrahydro-furan-(2R)-phosphonate;

(5R)-(2-amino-6-cyclopropylamino-purin-9-ylmethyl)-(4R)-fluoro-tetrahydro-furan-(2S)-phosphonate;

(5R)-(2-amino-6-cyclopropylamino-purin-9-ylmethyl)-(4R)-fluoro-tetrahydro-furan-(2R)-phosphonate;

(5R)-(2-amino-6-cyclopropylamino-purin-9-ylmethyl)-(4S)-fluoro-tetrahydro-furan-(2S)-phosphonate;

(5R)-(2-amino-6-cyclopropylamino-purin-9-ylmethyl)-(4S)-fluoro-tetrahydro-furan-(2R)-phosphonate;

(5R)-(2-amino-6-cyclopropylamino-purin-9-ylmethyl)-(4S)-hydroxy-tetrahydro-furan-(2S)-phosphonate;

(5R)-(2-amino-6-cyclopropylamino-purin-9-ylmethyl)-(4R)-hydroxy-tetrahydro-furan-(2R)-phosphonate;

(5R)-(2-amino-6-cyclopropylamino-purin-9-ylmethyl)-(4S)-hydroxy-tetrahydro-furan-(2R)-phosphonate;

(5R)-(2-amino-6-cyclopropylamino-purin-9-ylmethyl)-(4R)-hydroxy-tetrahydro-furan-(2S)-phosphonate;

(5R)-(2-amino-6-cyclopropylamino-purin-9-ylmethyl)-(4R)-iodo-tetrahydro-furan-(2S)-phosphonate;

(5R)-(2-amino-6-cyclopropylamino-purin-9-ylmethyl)-(4R)-iodo-tetrahydro-furan-(2R)-phosphonate;

(5R)-(2-amino-6-cyclopropylamino-purin-9-ylmethyl)-(4S)-iodo-tetrahydro-furan-(2S)-phosphonate;

(5R)-(2-amino-6-cyclopropylamino-purin-9-ylmethyl)-(4S)-iodo-tetrahydro-furan-(2R)-phosphonate;

(5R)-(2-amino-6-cyclopropylamino-purin-9-ylmethyl)-(4R)-chloro-tetrahydro-furan-(2S)-phosphonate;

(5R)-(2-amino-6-cyclopropylamino-purin-9-ylmethyl)-(4R)-chloro-tetrahydro-furan-(2R)-phosphonate;

(5R)-(2-amino-6-cyclopropylamino-purin-9-ylmethyl)-(4S)-chloro-tetrahydro-furan-(2S)-phosphonate;

(5R)-(2-amino-6-cyclopropylamino-purin-9-ylmethyl)-(4S)-chloro-tetrahydro-furan-(2R)-phosphonate;

(5R)-(2-amino-6-cyclopropylamino-purin-9-ylmethyl)-(4R)-bromo-tetrahydro-furan-(2S)-phosphonate;

(5R)-(2-amino-6-cyclopropylamino-purin-9-ylmethyl)-(4R)-bromo-tetrahydro-furan-(2R)-phosphonate;

(5R)-(2-amino-6-cyclopropylamino-purin-9-ylmethyl)-(4S)-bromo-tetrahydro-furan-(2S)-phosphonate;

(5R)-(2-amino-6-cyclopropylamino-purin-9-ylmethyl)-(4S)-bromo-tetrahydro-furan-(2R)-phosphonate; and pharmaceutically acceptable salts thereof.

42. A method according to claim 18, wherein said compound is selected from the group:

[(5R)-2(2-amino-6-cyclopropylamino-purin-9-ylmethyl)-4-methylene-tetrahydro-furan(2R)-yl]-phosphonic acid;

[(5S)-2(2-amino-6-cyclopropylamino-purin-9-ylmethyl)-4-methylene-tetrahydro-furan(2S)-yl]-phosphonic acid;

[(5R)-2(2-amino-6-cyclopropylamino-purin-9-ylmethyl)-4-methylene-tetrahydro-furan(2S)-yl]-phosphonic acid;

[(5S)-2(2-amino-6-cyclopropylamino-purin-9-ylmethyl)-4-methylene-tetrahydro-furan(2R)-yl]-phosphonic acid; and pharmaceutically acceptable salts thereof.

43. A pharmaceutical formulation according to claim 17, wherein said compound is selected from the group:

(5R)-(2-amino-6-hydroxy-purin-9-ylmethyl)-4S)-azido-tetrahydro-furan-(2S)-phosphonate;

(5R)-(2-amino-6-hydroxy-purin-9-ylmethyl)-(4R)-azido-tetrahydro-furan-(2S)-phosphonate;

(5R)-(2-amino-6-hydroxy-purin-9-ylmethyl)-(4S)-azido-tetrahydro-furan-(2R)-phosphonate;

(5R)-(2-amino-6-hydroxy-purin-9-ylmethyl)-(4R)-azido-tetrahydro-furan-(2R)-phosphonate;

(5R)-(2-amino-6-hydroxy-purin-9-ylmethyl)-(4R)-fluoro-tetrahydro-furan-(2S)-phosphonate;

(5R)-(2-amino-6-hydroxy-purin-9-ylmethyl)-(4R)-fluoro-tetrahydro-furan-(2R)-phosphonate;

(5R)-(2-amino-6-hydroxy-purin-9-ylmethyl)-(4S)-fluoro-tetrahydro-furan-(2S)-phosphonate;

(5R)-(2-amino-6-hydroxy-purin-9-ylmethyl)-(4S)-fluoro-tetrahydro-furan-(2R)-phosphonate;

(5R)-(2-amino-6-hydroxy-purin-9-ylmethyl)-(4S)-hydroxy-tetrahydro-furan-(2S)-phosphonate;

(5R)-(2-amino-6-hydroxy-purin-9-ylmethyl)-(4R)-hydroxy-tetrahydro-furan-(2R)-phosphonate;

(5R)-(2-amino-6-hydroxy-purin-9-ylmethyl)-(4S)-hydroxy-tetrahydro-furan-(2R)-phosphonate;

(5R)-(2-amino-6-hydroxy-purin-9-ylmethyl)-(4R)-hydroxy-tetrahydro-furan-(2S)-phosphonate;

(5R)-(2-amino-6-hydroxy-purin-9-ylmethyl)-(4R)-iodo-tetrahydro-furan-(2S)-phosphonate;

(5R)-(2-amino-6-hydroxy-purin-9-ylmethyl)-(4R)-iodo-tetrahydro-furan-(2R)-phosphonate;

(5R)-(2-amino-6-hydroxy-purin-9-ylmethyl)-(4S)-iodo-tetrahydro-furan-(2S)-phosphonate;

(5R)-(2-amino-6-hydroxy-purin-9-ylmethyl)-(4S)-iodo-tetrahydro-furan-(2R)-phosphonate;

(5R)-(2-amino-6-hydroxy-purin-9-ylmethyl)-4R)-chloro-tetrahydro-furan-(2S)-phosphonate;

(5R)-(2-amino-6-hydroxy-purin-9-ylmethyl)-(4R)-chloro-tetrahydro-furan-(2R)-phosphonate;

(5R)-(2-amino-6-hydroxy-purin-9-ylmethyl)-(4S)-chloro-tetrahydro-furan-(2S)-phosphonate;

(5R)-(2-amino-6-hydroxy-purin-9-ylmethyl)-(4S)-chloro-tetrahydro-furan-(2R)-phosphonate;

(5R)-(2-amino-6-hydroxy-purin-9-ylmethyl)-(4R)-bromo-tetrahydro-furan-(2S)-phosphonate;

(5R)-(2-amino-6-hydroxy-purin-9-ylmethyl)-(4R)-bromo-tetrahydro-furan-(2R)-phosphonate;

(5R)-(2-amino-6-hydroxy-purin-9-ylmethyl)-(4S)-bromo-tetrahydro-furan-(2S)-phosphonate;

(5R)-(2-amino-6-hydroxy-purin-9-ylmethyl)-(4S)-bromo-tetrahydro-furan-(2R)-phosphonate; and pharmaceutically acceptable salts thereof.

44. A pharmaceutical formulation according to claim 17, wherein said compound is selected from the group:

[(5R)-2(2-amino-6-hydroxy-purin-9-ylmethyl)-4-methylene-tetrahydro-furan(2R)-yl]-phosphonic acid;

[(5S)-2(2-amino-6-hydroxy-purin-9-ylmethyl)-4-methylene-tetrahydro-furan(2S)-yl]-phosphonic acid;

[(5R)-2(2-amino-6-hydroxy-purin-9-ylmethyl)-4-methylene-tetrahydro-furan(2S)-yl]-phosphonic acid;

[(5S)-2(2-amino-6-hydroxy-purin-9-ylmethyl)4-methylene-tetrahydro-furan(2R)-yl]-phosphonic acid; and pharmaceutically acceptable salts thereof.

45. A pharmaceutical formulation according to claim 17, wherein said compound is selected from the group:

(5R)-(2-amino-6-cyclopropylamino-purin-9-ylmethyl)-(4S)-azido-tetrahydro-furan-(2S)-phosphonate;

(5R)-(2-amino-6-cyclopropylamino-purin-9-ylmethyl)-(4R)-azido-tetrahydro-furan-(2S)-phosphonate;

(5R)-(2-amino-6-cyclopropylamino-purin-9-ylmethyl)-(4S)-azido-tetrahydro-furan-(2R)-phosphonate;

(5R)-(2-amino-6-cyclopropylamino-purin-9-ylmethyl)-(4R)-azido-tetrahydro-furan-(2R)-Phosphonate;

(5R)-(2-amino-6-cyclopropylamino-purin-9-ylmethyl)-(4R)-fluoro-tetrahydro-furan-(2S)-phosphonate;

(5R)-(2-amino-6-cyclopropylamino-purin-9-ylmethyl)-(4R)-fluoro-tetrahydro-furan-(2R)-phosphonate;

(5R)-(2-amino-6-cyclopropylamino-purin-9-ylmethyl)-(4S)-fluoro-tetrahydro-furan-(2S)-phosphonate;

(5R)-(2-amino-6-cyclopropylamino-purin-9-ylmethyl)-(4S)-fluoro-tetrahydro-furan-(2R)-phosphonate;

(5R)-(2-amino-6-cyclopropylamino-purin-9-ylmethyl)-(4S)-hydroxy-tetrahydro-furan-(2S)-phosphonate;

(5R)-(2-amino-6-cyclopropylamino-purin-9-ylmethyl)-(4R)-hydroxy-tetrahydro-furan-(2R)-phosphonate;

(5R)-(2-amino-6-cyclopropylamino-purin-9-ylmethyl)-(4S)-hydroxy-tetrahydro-furan-(2R)-phosphonate;

(5R)-(2-amino-6-cyclopropylamino-purin-9-ylmethyl)-(4R)-hydroxy-tetrahydro-furan-(2S)-phosphonate;

(5R)-(2-amino-6-cyclopropylamino-purin-9-ylmethyl)-(4R)-iodo-tetrahydro-furan-(2S)-phosphonate;

(5R)-(2-amino-6-cyclopropylamino-purin-9-ylmethyl)-(4R)-iodo-tetrahydro-furan-(2R)-phosphonate;

(5R)-(2-amino-6-cyclopropylamino-purin-9-ylmethyl)-(4S)-iodo-tetrahydro-furan-(2S)-phosphonate;

(5R)-(2-amino-6-cyclopropylamino-purin-9-ylmethyl)-(4S)-iodo-tetrahydro-furan-(2R)-phosphonate;

(5R)-(2-amino-6-cyclopropylamino-purin-9-ylmethyl)-(4R)-chloro-tetrahydro-furan-(2S)-phosphonate;

(5R)-(2-amino-6-cyclopropylamino-purin-9-ylmethyl)-(4R)-chloro-tetrahydro-furan-(2R)-phosphonate;

(5R)-(2-amino-6-cyclopropylamino-purin-9-ylmethyl)-(4S)-chloro-tetrahydro-furan-(2S)-phosphonate;

(5R)-(2-amino-6-cyclopropylamino-purin-9-ylmethyl)-(4S)-chloro-tetrahydro-furan-(2R)-phosphonate;

(5R)-(2-amino-6-cyclopropylamino-purin-9-ylmethyl)-(4R)-bromo-tetrahydro-furan-(2S)-phosphonate;

(5R)-(2-amino-6-cyclopropylamino-purin-9-ylmethyl)-(4R)-bromo-tetrahydro-furan-(2R)-phosphonate;

(5R)-(2-amino-6-cyclopropylamino-purin-9-ylmethyl)-(4S)-bromo-tetrahydro-furan-(2S)-phosphonate;

(5R)-(2-amino-6-cyclopropylamino-purin-9-ylmethyl)-(4S)-bromo-tetrahydro-furan-(2R)-phosphonate; and pharmaceutically acceptable salts thereof.

46. A pharmaceutical formulation according to claim 17, wherein said compound is selected from the group:

[(5R)-2(2-amino-6-cyclopropylamino-purin-9-ylmethyl)-4-methylene-tetrahydro-furan(2R)-yl]-phosphonic acid;

[(5S)-2(2-amino-6-cyclopropylamino-purin-9-ylmethyl)-4-methylene-tetrahydro-furan(2S)-yl]-phosphonic acid;

[(5R)-2(2-amino-6-cyclopropylamino-purin-9-ylmethyl)-4-methylene-tetrahydro-furan(2S)-yl]-phosphonic acid;

[(5S)-2(2-amino-6-cyclopropylamino-purin-9-ylmethyl)-4-methylene-tetrahydro-furan(2R)-yl]-phosphonic acid; and pharmaceutically acceptable salts thereof.

47. A nucleotide analogue selected from the group:

[(5R)-2(2-amino-6-cyclopropylamino-purin-9-ylmethyl)-2,5-dihydro-furan-(2R)-yl]-phosphonic acid;

[(5S)-2(2-amino-6-cyclopropylamino-purin-9-ylmethyl)-2,5-dihydro-furan-(2S)-yl]-phosphonic acid;

[(5R)-2(2-amino-6-cyclopropylamino-purin-9-ylmethyl)-2,5-dihydro-furan-(2S)-yl]-phosphonic acid;

[(5S)-2(2-amino-6-cyclopropylamino-purin-9-ylmethyl)-2,5-dihydro-furan-(2R)-yl]-phosphonic acid; and pharmaceutically acceptable salts thereof.

48. A pharmaceutical formulation comprising a pharmaceutically effective amount of a compound according to claim 47 and a pharmaceutically acceptable carrier.

49. A method of treating an HIV infection in a mammal comprising administering to said mammal the pharmaceutical formulation according to claim 47.

* * * * *